US009572647B2

(12) United States Patent
Couse et al.

(10) Patent No.: US 9,572,647 B2
(45) Date of Patent: Feb. 21, 2017

(54) PAIRED THERMOMETER TEMPERATURE DETERMINATION

(71) Applicant: i4c Innovations Inc., Chantilly, VA (US)

(72) Inventors: John Michael Couse, Toronto (CA); Amanda Landis-Hanna, Fairfax, VA (US)

(73) Assignee: i4c Innovations Inc., Chantilly, VA (US)

(*) Notice: Subject to any disclaimer, the term of this patent is extended or adjusted under 35 U.S.C. 154(b) by 0 days.

(21) Appl. No.: 14/570,935

(22) Filed: Dec. 15, 2014

(65) Prior Publication Data

US 2015/0182322 A1 Jul. 2, 2015

Related U.S. Application Data

(60) Provisional application No. 61/922,417, filed on Dec. 31, 2013.

(51) Int. Cl.
*A61B 5/00* (2006.01)
*A61D 13/00* (2006.01)
*A01K 29/00* (2006.01)
*A61B 5/01* (2006.01)
*G01K 1/20* (2006.01)
*G01K 13/00* (2006.01)

(52) U.S. Cl.
CPC ............ *A61D 13/00* (2013.01); *A01K 29/005* (2013.01); *A61B 5/01* (2013.01); *A61B 5/6822* (2013.01); *G01K 1/20* (2013.01); *G01K 13/002* (2013.01); *A61B 2503/40* (2013.01)

(58) Field of Classification Search
CPC ......... A61B 5/01; A61B 5/015; A61B 5/0008; A61B 5/6804; A61D 13/00
USPC ....................................................... 600/549
See application file for complete search history.

(56) References Cited

U.S. PATENT DOCUMENTS 5,653,238 A * 8/1997 Pompei .................... G01J 5/02
374/E13.003
6,862,550 B1 3/2005 Cook
7,828,743 B2 11/2010 Fraden
8,452,382 B1 5/2013 Roth
(Continued)

FOREIGN PATENT DOCUMENTS

GB 1426569 A 3/1976
JP 2005102959 A 4/2005
(Continued)

OTHER PUBLICATIONS

Apr. 23, 2015 (PCT) International Search Report and Written Opinion—App. PCT/US2014/072743.
(Continued)

*Primary Examiner* — Max Hindenburg
(74) *Attorney, Agent, or Firm* — Banner & Witcoff, Ltd.

(57) ABSTRACT

A system and method for monitoring the health of an animal using multiple sensors is described. The wearable device may include one or more sensors whose resultant signal levels may be analyzed in the wearable device or uploaded to a data management server for additional analysis. In one example, paired thermometers are used to estimate a core temperature of the animal, with one of the thermometers facing inward toward the animal and the other thermometer facing away from the animal.

20 Claims, 32 Drawing Sheets

(56) References Cited

U.S. PATENT DOCUMENTS

| | | |
|---|---|---|
| 9,183,738 B1 * | 11/2015 | Allen, Sr. .............. G08C 17/02 |
| 2002/0026119 A1 | 2/2002 | Pompei |
| 2009/0105605 A1 | 4/2009 | Abreu |
| 2009/0187392 A1 | 7/2009 | Riskey et al. |
| 2012/0238901 A1 | 9/2012 | Augustine |
| 2014/0169400 A1 | 6/2014 | Baarman et al. |

FOREIGN PATENT DOCUMENTS

| | | |
|---|---|---|
| WO | 2005092177 A1 | 10/2005 |
| WO | 2008057883 A2 | 5/2008 |
| WO | 2012104658 A2 | 8/2012 |
| WO | 2013118121 A1 | 8/2013 |

OTHER PUBLICATIONS

Oct. 13, 2016 (AU) First Examination Report—App. 2014373849.
Sep. 15, 2016 (NZ) First Examination Report—App. 721658.
Sep. 8, 2016 (NZ) First Examination Report—App. 721702.

\* cited by examiner

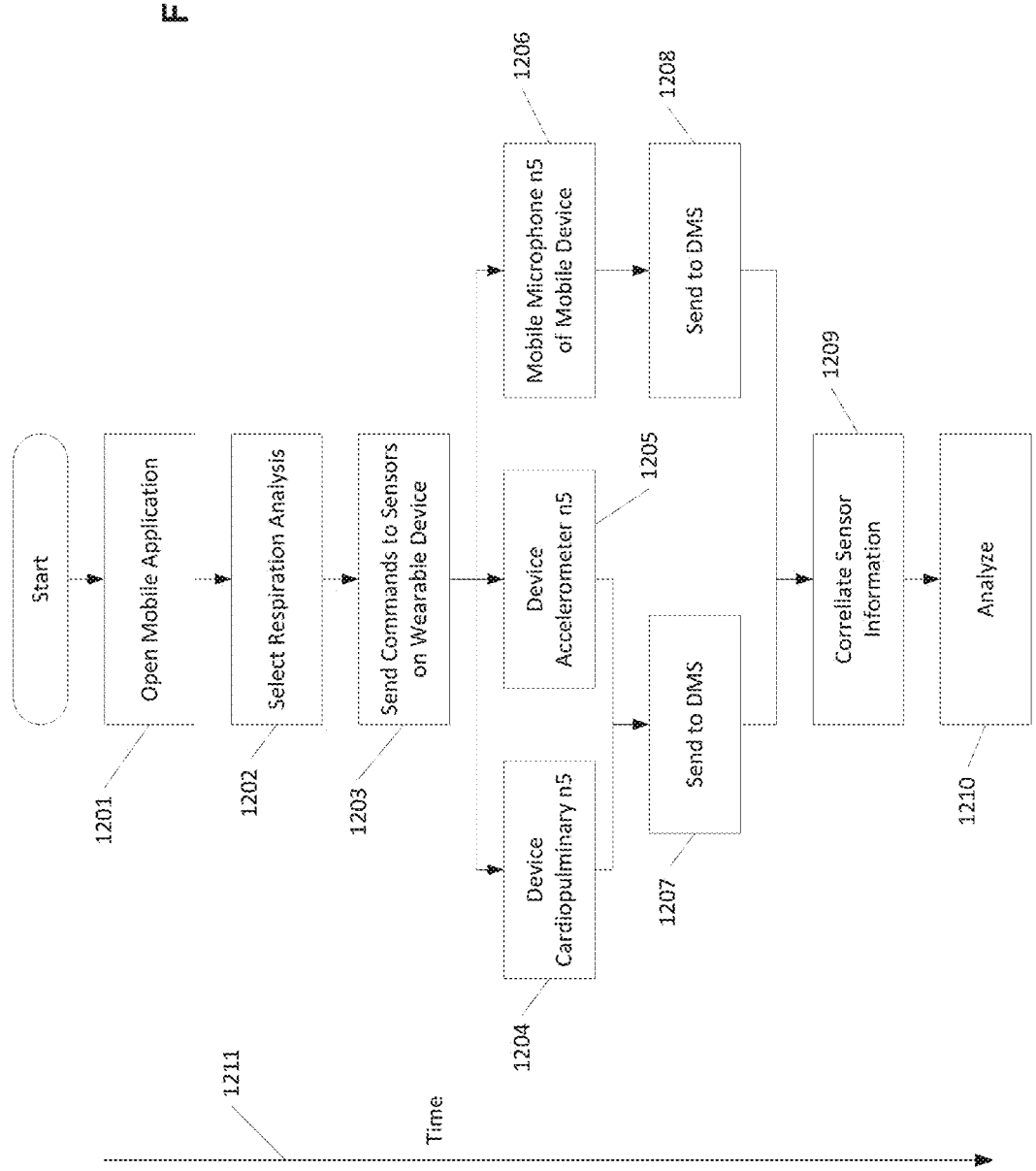

| Sensor number | Sensor Type | Location | Primary Purpose | Category | Master/Slave | Secondary Purpose |
|---|---|---|---|---|---|---|
| N1 | Light meter/Spectrometer (visible, IR, and/or UV) | Wearable | Light levels/Spectrum-specific light levels | Ambient Conditions | S | Indoor/outdoor indicator |
| N2 | Peak sound | Wearable | Sound levels | Ambient Conditions | S | Bark detection/impact event |
| N3 | Accelerometer | Wearable | General activity | Animal Physiology | M | Master to control UWB and other sensors |
| N4 | GPS | Wearable | Location based services | Location | S | Signal strength, location of visible sensors |
| N5 | Cardiopulmonary | Wearable | Heart Rate and Respiration | Animal Physiology | S | Stroke volume/blood pressure change |
| N6 | Ambient Temperature | Wearable | Ambient Temperature | Ambient Conditions | M | Core temperature adjustment |
| N7 | Core Temperature | Wearable | Core Temperature | Animal Physiology | M | - |
| N8 | Wi-Fi Signal | Wearable | Communications | Communications | S | Presence & Proximity |
| N9 | Bluetooth Signal | Wearable | Communications | Communications | S | Presence & Proximity |
| N10 | RF Signal | Wearable | Presence & Proximity | Location | M | - |
| N11 | GSM Signal | Wearable | Communications | Communications | S | Presence & Proximity |
| N12 | Battery Temp | Wearable | Overheating alerts | Physical device status | M | Reference point for core temperature determination |
| N13 | Battery Strength | Wearable | Power considerations/operation modifications | Physical device status | M | Modify sensor profiles based on level |
| N14 | High resolution microphone | Wearable/Separate | High definition sound capture | Animal Physiology | M | Audio file |
| N15 | Relative Humidity | Wearable | Humidity level | Ambient Conditions | S | Temperature adjustment |
| N16 | Time of Day | Wearable | Time stamp | Time normalizaiton | M | Windowing |

Sensor Profiles

| | | Profile 0 | | | |
| | | Owner - Normal Monitoring | | | |
| Sensor number | Sensor Type | Low Threshold | High Threshold | Frequency | Granularity |
|---|---|---|---|---|---|
| N1 | Light meter/Spectrometer (visible, IR, and/or UV) | 0lx | 20,000 lux | Every 30 minutes | Low |
| N2 | Peak sound | N/A | 120 dB | Interrupt-based | Low |
| N3 | Accelerometer | 0 | 1G | Always on | Low |
| N4 | GPS | N/A | Speed over 30 mph | On demand | Low |
| N5 | Cardiopulmonary | HR < 60<br>Resp <10 | HR > 140<br>Resp > 34 | Scheduled nightly | Low |
| N6 | Ambient Temperature | <-5C | >40 C | Every 30 minutes | Low |
| N7 | Core Temperature | < 37.5 C | >40 C | Scheduled nightly | Low |
| N8 | Wi-Fi Signal | < 20% signal | N/A | Standby | N/A |
| N9 | Bluetooth Signal | < 20% signal | N/A | Standby | N/A |
| N10 | RF Signal | < 20% signal | N/A | 1 minute intervals | N/A |
| N11 | GSM Signal | < 20% signal | N/A | Standby | N/A |
| N12 | Battery Temp | < 5 C | >40 C | On demand | N/A |
| N13 | Battery Strength | < 15 % | N/A | Hourly | N/A |
| N14 | High resolution microphone | N/A | N/A | Off | N/A |
| N15 | Relative Humidity | < 30% | >90% | Every 30 minutes | Low |
| N16 | Time of Day | N/A | N/A | Synchronized w/network time | N/A |

Figure 16A

Sensor Profiles 1600

| Sensor number 1601 | Sensor Type 1602 | Profile 1 ||||
|---|---|---|---|---|---|
| | | Owner - Enhanced Monitoring ||||
| | | Low Threshold 1605B | High Threshold 1606B | Frequency 1607B | Granularity 1608B |
| N1 | Light meter/Spectrometer (visible, IR, and/or UV) | 100 lux | 10,000 lux | Every 60 seconds | High |
| N2 | Peak sound | N/A | 90 dB | Every 60 seconds | High |
| N3 | Accelerometer | 0 | 10G | Always on | High |
| N4 | GPS | 0 | Speed over 25 mph | Every 60 seconds | High |
| N5 | Cardiopulmonary | HR < 80<br>Resp < 15 | HR > 100<br>Resp > 30 | Hourly | High |
| N6 | Ambient Temperature | < 5.0 C | > 30 C | Every 10 minutes | High |
| N7 | Core Temperature | < 38 C | > 39.2 C | Hourly | High |
| N8 | Wi-Fi Signal | < 40% Signal | N/A | Every 60 seconds | N/A |
| N9 | Bluetooth Signal | < 40% Signal | N/A | Every 60 seconds | N/A |
| N10 | RF Signal | < 40% Signal | N/A | Every 10 seconds | N/A |
| N11 | GSM Signal | < 40% Signal | N/A | Every 60 seconds | N/A |
| N12 | Battery Temp | < 10 C | > 30 C | Always on | N/A |
| N13 | Battery Strength | < 25% | N/A | Always on | N/A |
| N14 | High re-solution microphone | 0 | 85 dB | On Demand | High |
| N15 | Relative Humidity | < 40% | > 80% | Every 60 seconds | High |
| N16 | Time of Day | N/A | N/A | Synchronized w/network time | N/A |

Figure 16B

Sensor Profiles

| Sensor number | Sensor Type | Profile 2 Vet - Normal Monitoring | | | |
|---|---|---|---|---|---|
| | | Low Threshold | High Threshold | Frequency | Granularity |
| N1 | Light meter/Spectrometer (visible, IR, and/or UV) | N/A | N/A | N/A | N/A |
| N2 | Peak sound | N/A | N/A | N/A | N/A |
| N3 | Accelerometer | 0 | 5G | Always on | Low |
| N4 | GPS | N/A | N/A | N/A | N/A |
| N5 | Cardiopulmonary | HR < 60 Resp <10 | HR > 140 Resp > 34 | Hourly | High |
| N6 | Ambient Temperature | < 16C | > 24 C | Hourly | Low |
| N7 | Core Temperature | < 37.5 C | > 39.7 | Hourly | Low |
| N8 | Wi-Fi Signal | N/A | N/A | N/A | N/A |
| N9 | Bluetooth Signal | N/A | N/A | N/A | N/A |
| N10 | RF Signal | N/A | N/A | N/A | N/A |
| N11 | GSM Signal | N/A | N/A | N/A | N/A |
| N12 | Battery Temp | N/A | N/A | N/A | N/A |
| N13 | Battery Strength | N/A | N/A | N/A | N/A |
| N14 | High resolution microphone | N/A | N/A | N/A | N/A |
| N15 | Relative Humidity | N/A | N/A | N/A | N/A |
| N16 | Time of Day | N/A | N/A | Synchronized w/ network time | N/A |

Figure 16C

Sensor Profiles

| Sensor number | Sensor Type | Profile 3 Vet - Enhanced Monitoring ||||
|---|---|---|---|---|---|
| | | Low Threshold | High Threshold | Frequency | Granularity |
| N1 | Light meter/Spectrometer (visible, IR, and/or UV) | N/A | N/A | N/A | N/A |
| N2 | Peak sound | N/A | N/A | N/A | N/A |
| N3 | Accelerometer | 0 | 4 G | Always on | High |
| N4 | GPS | N/A | N/A | N/A | N/A |
| N5 | Cardiopulmonary | HR < 80 Resp <15 | HR > 110 Resp > 30 | Every 10 minutes | High |
| N6 | Ambient Temperature | < 20 C | > 22 C | Every 10 minutes | High |
| N7 | Core Temperature | < 38 C | > 39.2 C | Every minute | High |
| N8 | Wi-Fi Signal | N/A | N/A | N/A | N/A |
| N9 | Bluetooth Signal | N/A | N/A | N/A | N/A |
| N10 | RF Signal | N/A | N/A | N/A | N/A |
| N11 | GSM Signal | N/A | N/A | N/A | N/A |
| N12 | Battery Temp | N/A | N/A | N/A | N/A |
| N13 | Battery Strength | N/A | N/A | N/A | N/A |
| N14 | High resolution microphone | N/A | N/A | N/A | N/A |
| N15 | Relative Humidity | N/A | N/A | N/A | N/A |
| N16 | Time of Day | N/A | N/A | N/A | N/A |

Figure 16D

Sensor Profiles 1600

1601 1602

| Sensor number | Sensor Type | Profile 4 Vet - Symptom Monitoring 1 1603E | | | |
|---|---|---|---|---|---|
| | | Low Threshold | High Threshold | Frequency | Granularity 1604E |
| N1 | Light meter/Spectrometer (visible, IR, and/or UV) | N/A | N/A | N/A | N/A |
| N2 | Peak sound | N/A | N/A | Always on | High |
| N3 | Accelerometer | 0 | 3 G | Ever hour | High |
| N4 | GPS | N/A | Speed over 10 mph | Every 10 minutes | High |
| N5 | Cardiopulmonary | HR < 80 Resp < 10 | HR > 110 Resp > 30 | | |
| N6 | Ambient Temperature | < 16 C | > 24 C | Hourly | Low |
| N7 | Core Temperature | < 38 C | > 39.2 C | Every 10 minutes | High |
| N8 | Wi-Fi Signal | N/A | N/A | N/A | N/A |
| N9 | Bluetooth Signal | N/A | N/A | N/A | N/A |
| N10 | RF Signal | N/A | N/A | N/A | N/A |
| N11 | GSM Signal | N/A | N/A | N/A | N/A |
| N12 | Battery Temp | N/A | N/A | N/A | N/A |
| N13 | Battery Strength | N/A | N/A | N/A | N/A |
| N14 | High resolution microphone | 0 | 85 db | On demand | High |
| N15 | Relative Humidity | N/A | N/A | N/A | N/A |
| N16 | Time of Day | N/A | N/A | Synchronized w/ network time | N/A |

Sensor Profiles 1500

1601 Sensor number | 1602 Sensor Type | 1605F Low Threshold | 1606F High Threshold | 1607F Frequency | 1604F Granularity Profile 5 — Vet - Symptom Monitoring 2 (1603F)

| Sensor number | Sensor Type | Low Threshold | High Threshold | Frequency | Granularity |
|---|---|---|---|---|---|
| N1 | Light meter/Spectrometer (visible, IR, and/or UV) | N/A | N/A | N/A | N/A |
| N2 | Peak sound | N/A | N/A | N/A | N/A |
| N3 | Accelerometer | 0 | 3 G | Always on | Low |
| N4 | GPS | N/A | Speed over 10 mph | Every 10 minutes | High |
| N5 | Cardiopulmonary | HR < 60 Resp < 10 | HR > 100 Resp > 30 | Every minute | High |
| N6 | Ambient Temperature | < 20 C | > 22 C | Every 10 minutes | N/A |
| N7 | Core Temperature | < 38 C | > 39.2 | Every Minute | High |
| N8 | Wi-Fi Signal | N/A | N/A | N/A | N/A |
| N9 | Bluetooth Signal | N/A | N/A | N/A | N/A |
| N10 | RF Signal | N/A | N/A | N/A | N/A |
| N11 | GSM Signal | N/A | N/A | N/A | N/A |
| N12 | Battery Temp | N/A | N/A | N/A | N/A |
| N13 | Battery Strength | N/A | N/A | N/A | N/A |
| N14 | High resolution microphone | 0 | 70 db | On demand | High |
| N15 | Relative Humidity | N/A | N/A | N/A | N/A |
| N16 | Time of Day | N/A | N/A | Synchronized w/network time | N/A |

Sensor Profiles 1600

| Sensor number 1601 | Sensor Type 1602 | Profile 6 — Enhanced Sensitivity 1603G | | | |
|---|---|---|---|---|---|
| | | Low Threshold 1605G | High Threshold 1606G | Frequency 1607G | Granularity 1608G 1604G |
| N1 | Light meter/Spectrometer (visible, IR, and/or UV) | N/A | N/A | N/A | N/A |
| N2 | Peak sound | N/A | N/A | N/A | N/A |
| N3 | Accelerometer | 0 | 3.6 | Always on | High |
| N4 | GPS | N/A | N/A | N/A | High |
| N5 | Cardiopulmonary | HR < 50 Resp < 40 | HR > 90 Resp > 25 | Continuous | High |
| N6 | Ambient Temperature | N/A | N/A | N/A | N/A |
| N7 | Core Temperature | < 38 C | > 39.2 C | Continuous | High |
| N8 | Wi-Fi Signal | N/A | N/A | N/A | N/A |
| N9 | Bluetooth Signal | N/A | N/A | N/A | N/A |
| N10 | RF Signal | N/A | N/A | N/A | N/A |
| N11 | GSM Signal | N/A | N/A | N/A | N/A |
| N12 | Battery Temp | N/A | N/A | N/A | N/A |
| N13 | Battery Strength | N/A | N/A | N/A | N/A |
| N14 | High resolution microphone | 0 | 50 dB | On Demand | High |
| N15 | Relative Humidity | N/A | N/A | N/A | N/A |
| N16 | Time of Day | N/A | N/A | Synchronized w/ network time | N/A |

Figure 16G

Sensor Profiles — 1701

| Sensor number | Sensor Type | Breed Adjustment 1703 |
|---|---|---|
| N1 | Light meter/Spectrometer (visible, IR, and/or UV) | |
| N2 | Peak sound | X |
| N3 | Accelerometer | X |
| N4 | GPS | X |
| N5 | Cardiopulmonary | X |
| N6 | Ambient Temperature | X |
| N7 | Core Temperature | X |
| N8 | Wi-Fi Signal | |
| N9 | Bluetooth Signal | |
| N10 | RF Signal | |
| N11 | GSM Signal | |
| N12 | Battery Temp | |
| N13 | Battery Strength | |
| N14 | High resolution microphone | X |
| N15 | Relative Humidity | X |
| N16 | Time of Day | |

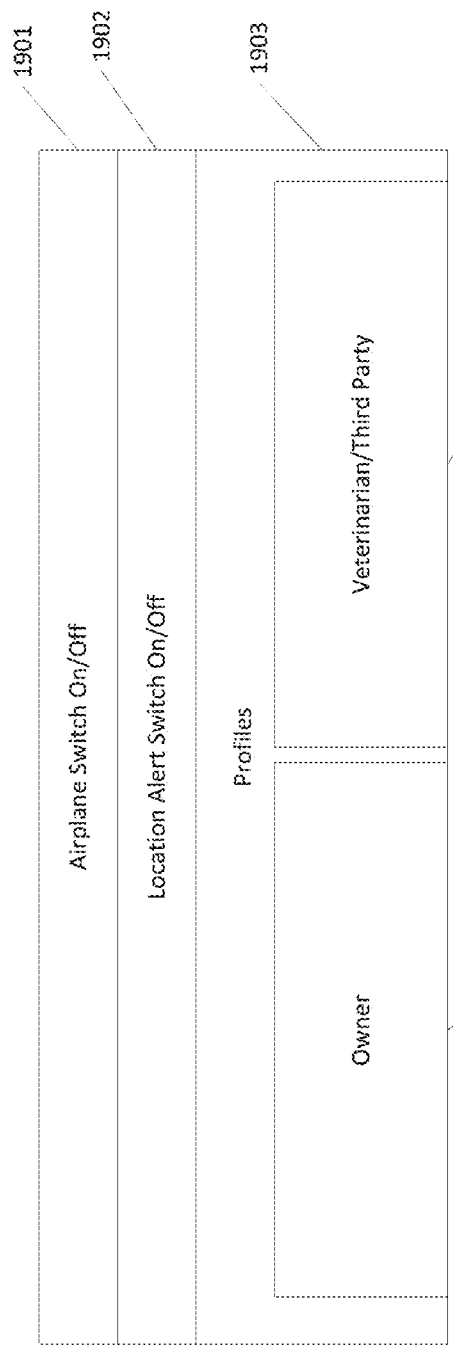
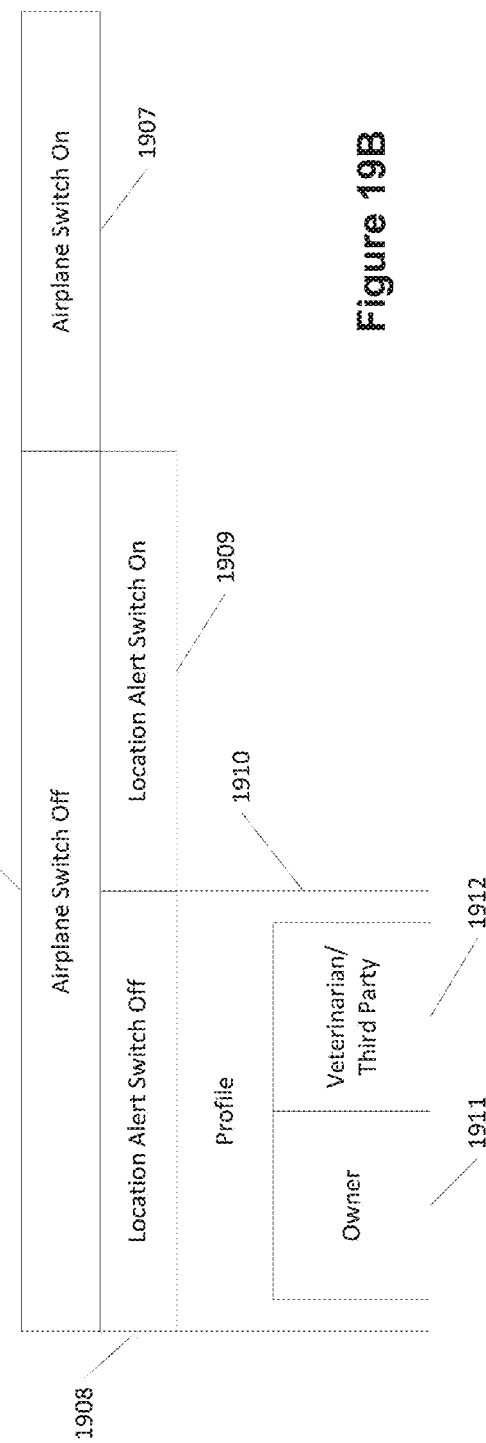
Figure 19A
Figure 19B

PAIRED THERMOMETER TEMPERATURE DETERMINATION

CROSS-REFERENCE TO RELATED APPLICATIONS

This application claims priority to U.S. provisional application Ser. No. 61/922,417 filed on Dec. 31, 2013, whose contents are expressly incorporated herein by reference.

FIELD OF THE DISCLOSURE

Aspects of the invention relate generally to animal safety, wellness, and health monitoring. More particularly, some aspects of the invention relate to a viewing and system management system that monitors a pet's health and wellness.

BACKGROUND

Animals are far more stoic than humans and often do not complain or demonstrate pain even while they are making adjustments to accommodate their distress. Through market research, pet owners have made it quite clear that they do not need to be told that their pet is sick, but rather they need to know when their pet is getting sick and what preventative steps they should take in response. For example, if an owner knew her pet was getting sick, she could increase her level of observation (e.g., observe whether the animal is eating, drinking, and/or eliminating normally), increase or decrease certain activities (e.g., walks, etc.), and/or visit a veterinarian.

Similarly, veterinarians have very limited visibility into the health of their animal patients as most clinical encounters between a veterinarian and an animal patient are episodic in nature. As such, during normal checkups veterinarians may not always perform or rely on certain readings such as, e.g., blood pressure, respiration rate/variability, or core temperature (sticking a thermometer in the animal's rectum) because such readings may stress the animal further, may be difficult to perform (blood pressure), and/or are unreliable in a stressful clinical setting (animals may exhibit elevated readings in a veterinarian's office with other animals around sometimes referred to as "white coat hypertension" or "white coat syndrome").

Accordingly, some past solutions have attempted to remotely monitor an animal in order to provide an animal owner with data relating to the animal's health status while providing veterinarians further data to assist in diagnosing animal health conditions. However, each of these past solutions suffers drawbacks in that they do not provide a comprehensive view of the animal's health and do not provide an owner and/or a veterinarian with adequate information to determine the animal's health status.

Accordingly, there remains a need to provide a pet owner and/or a veterinarian with comprehensive information regarding a pet or other animal's current status such that the pet owner and/or veterinarian may better understand the wellness of a pet through non-invasive remote monitoring in a stable home environment to pick up subtle vital signs indicators that could be precursors to developing health conditions.

SUMMARY

One or more aspects of the present disclosure relate to monitoring a pet or other animal's health and wellness using two or more sensors in order to provide a pet owner, veterinarian, or other party with content useful in monitoring the pet's overall condition. Also, inferences based on analyses of different signals from different sensors monitoring an animal's vital signs, physiological signs, or environmental factors may also be provided. Some aspects of the disclosure provide a wearable device with embedded sensors whose operation may be governed by various operating modes and/or profiles in addition to the signals from other sensors.

A system and method for monitoring the health of an animal using multiple sensors is described. The wearable device may include one or more sensors whose resultant signal levels may be analyzed in the wearable device or uploaded to a data management server for additional analysis. In one example, paired thermometers are used to estimate a core temperature of the animal, with one of the thermometers facing inward toward the animal and the other thermometer facing away from the animal.

The various aspects summarized previously may be embodied in various forms. The following description shows by way of illustration of various combinations and configurations in which the aspects may be practiced. It is understood that the described aspects and/or embodiments are merely examples, and that other aspects and/or embodiments may be utilized and structural and functional modifications may be made, without departing from the scope of the present disclosure.

BRIEF DESCRIPTION OF THE DRAWINGS

A more complete understanding of the present invention and the advantages thereof may be acquired by referring to the following description in consideration of the accompanying drawings, in which like reference numbers indicate like features.

FIG. 12 is a flowchart illustrating using readings from sensors from the wearable device and another sensor apart from the wearable device according to some aspects of the disclosure.

FIG. 13 shows a table with sensors and their related information in accordance with one or more aspects of the disclosure.

FIG. 14 is a table with potential master/slave relationships of various sensors identified in FIG. 13 in accordance with one or more embodiments of the disclosure.

FIGS. 16A-16G are illustrative examples of various sensors and how their threshold or thresholds, frequency of operation, and granularity may be modified based on different profiles in accordance with one or more aspects of the disclosure.

FIG. 17 shows an example of how various sensor profiles may be modified based on breed information of the animal to which the monitoring devices attached in accordance with one or more aspects of the disclosure.

FIGS. 19A-19B show the order in which operation modes take precedence over profiles based on the embodiment of FIG. 18 in accordance with one or more aspects of the disclosure.

DETAILED DESCRIPTION

Figure 1:
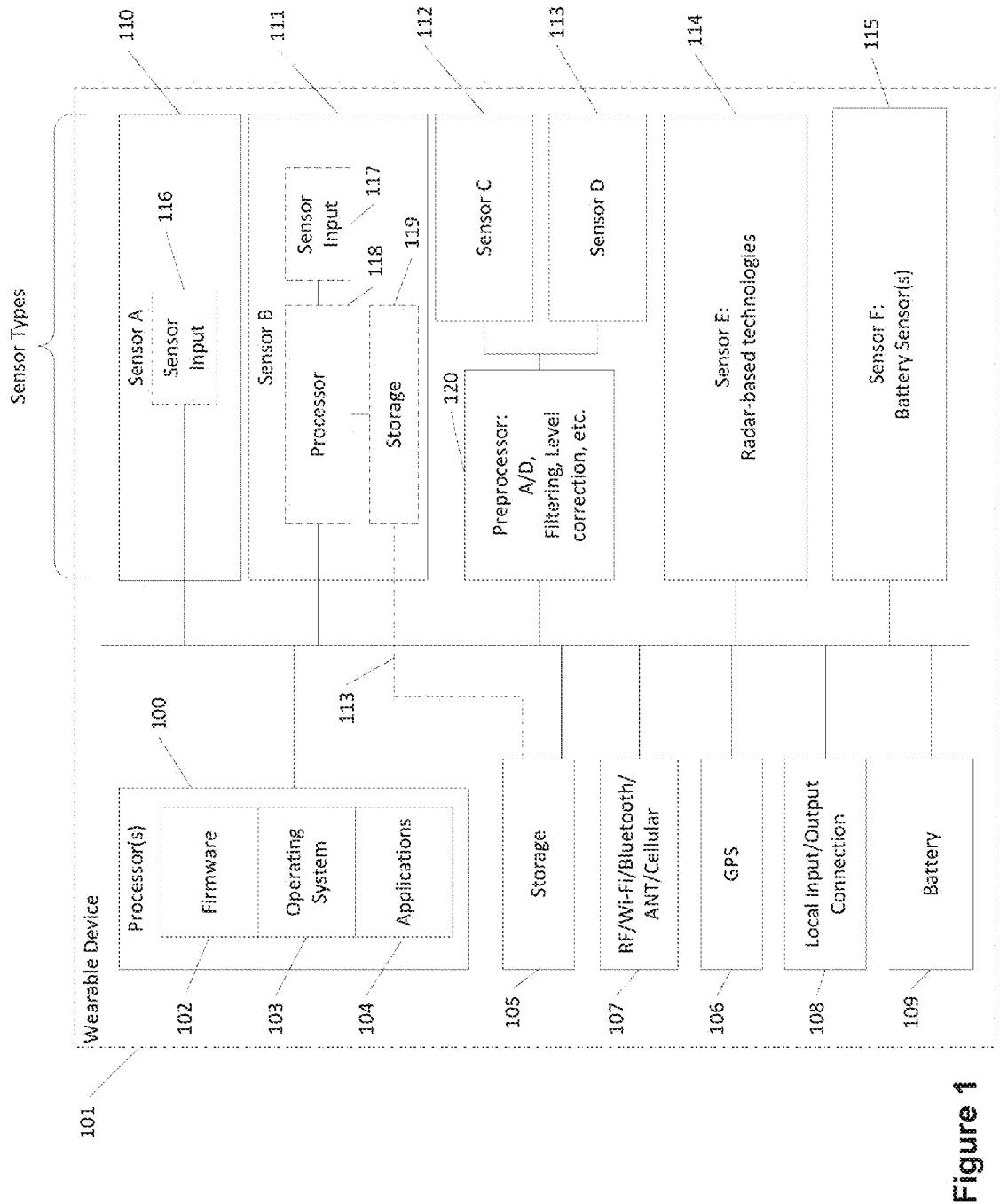
FIG. 1 is a schematic diagram of a wearable device for a pet and its components according to some aspects of the disclosure.

In the following description of the various embodiments, reference is made to the accompanying drawings, which form a part hereof, and in which is shown by way of illustration various embodiments in which the invention may be practiced. It is to be understood that other embodiments may be utilized and structural and functional modifications may be made without departing from the scope of the present invention.

General Overview

Aspects of the present disclosure are directed to a device worn by an animal including one or more sensors for monitoring one or more conditions of the animal and/or its environment. In some embodiments, the device may be a collar, harness, or other device placed on an animal by a human (e.g., a pet's owner). The wearable device may include a plurality of components including, e.g., one or more sensors and one or more components used to transmit data as described herein. For example, in some embodiments, the wearable device may include a plurality of contact, semi-contact, and non-contact sensors for obtaining information about the animal, its location, and its environment.

Additional aspects of the present disclosure are directed to analysis of the different sensors. For the purpose of this application, at least two locations at which the sensors are analyzed are described herein. First, the wearable device may analyze the sensor data. Second, a remote, data management system (referred to herein as "DMS") may process the information from the sensors. In addition, the DMS may process the information from the sensors in conjunction with additional information from sources other than the wearable device including information from ancillary sensors proximate to the wearable device (including stand-alone sensors and sensors attached to other devices, e.g., sensors attached to or part of smartphones). Further, the DMS may receive information from owners who have entered specific information based upon their observations of the animal. In addition, the DMS may receive information from third-parties including RSS feeds regarding ambient weather conditions local to the wearable device as well as data from third-party veterinarians or other service providers. It is appreciated that, in some implementations, the sensors may be analyzed only at one location or analyzed at three or more locations. The health-monitoring system may further use the owner observations of the animal collected through, e.g., companion web/mobile based applications, telephone call center activity/teleprompts, and the like. The owner observations may corroborate measured events (e.g., events measured by wearable device 101 and/or one or more external sensors) to assist in lowering the ongoing rate of false positives and false negatives. For example, in some embodiments, the health-monitoring system may include a mobile weight/size mobile device application which instructs the owner to wave a mobile camera integral to the mobile device across an animal with a pre-identified marker in the field of view. Pre-processed data derived from this action may then be uplifted to the DMS where conclusions can be derived as to the animal's weight and size. Such data is then appended to the animal's record. Other important owner recorded observations may include observable items such as caloric intake, blood in urine, black stools, smelly breath, excessive thirst, white skin patches around the face, recording the disposition of the animal, and the like. For instance, the caloric intake may be monitored by an owner through an application running on a computer or smartphone in which the owner identifies what food and how much is being consumed over what interval.

Further, while described herein as being located remote from the wearable device, the DMS may be located on the owner's smartphone or located on the wearable device based on the respective processing power of smartphone and wearable device. In these alternative embodiments, the "DMS" is identified by its ability to receive content from sources other than the sensors of the wearable device and process that additionally received content for forwarding to the owner and/or veterinarian of the specific animal. These alternative embodiments of the DMS are considered within the scope of the "data management system" unless specifically excluded herein. For instance, if the wearable device is considered the DMS, the wearable device would receive data from its own sensors as well as information from either sensors not located on the wearable device and/or additional content provided by the owner, veterinarian, or third party.

Further, the veterinarian may provide information to the DMS 301 including breed, age, weight, existing medical conditions, suspected medical conditions, appointment compliance and/or scheduling, current and past medications, and the like.

For the purposes of this disclosure, some sensors are described as a specific type of sensor in contrast to a more generic description of other sensors. For instance, while the specification describes the use of a GPS unit providing location information, other location identifying systems are considered equally useable including GLONASS, Beidou, Galileo, and satellite-based navigation systems. Similarly, while the specification describes the use of a GSM transceiver using GSM frequencies, other cellular chipsets may be readily used in place of or in addition to the GSM transceiver. For example, other types of transceivers may include UMTS, CDMA, AMPS, GPRS, CDMA (and its variants), DECT, iDEN, and other cellular technologies.

Also, for the purposes of this disclosure, various sensors and combination of sensors are described as being co-located on the wearable device. However, in various situations, one or more sensors may never be used in a specific version of the wearable device. For instance, GPS-related sensors may not be useful for a version of the wearable device that is only to be used post-surgery in a recovery ward of an animal hospital. Because precise location information is not needed when a veterinarian already knows the location of the animal (or even not useable when in doors), a version of the wearable device with the GPS sensor disabled or not even included may be used. Similarly, other sensors may be disabled in (or never included in) this version of the wearable device where those sensors are not expected to be used. For instance, an RF signal sensor (one that determines if a beacon signal from a base station is above a predetermined threshold) may not be provided in a version of the wearable device where that version of the wearable device is never expected to be used with a base station emitting a beacon signal.

As used in this disclosure, the term "content" is intended to cover both raw data and derived events. For instance, one example of the wearable device as described herein includes a profile/operation mode in which raw data from various sensors are uploaded to a data management on a continuous basis. Another example of the wearable device pre-processes information from various sensors and derives event information from the combination of signals (or lack thereof) from two or more sensors. These derived events are referred to as "device-derived events" as their derived in the wearable device. Similarly, the data management system may also derive events (referred to herein as "DMS-derived events") from content from the wearable device using only the raw data from the wearable device, the device-derived events, or a combination of both. Further, the DMS may further take into account content from ancillary or third-party sensors to corroborate and/or further enhance the DMS-derived events. For instance, data from ancillary or third-party sensors may include audio files, image files, video files, RFID information, and other types of information. To help correlate the data from ancillary or third-party sensors with data/device-derived events from the wearable device, the data from the ancillary or third-party sensors may include timestamps. These timestamps permit the data management system to use the data from the ancillary or third-party sensors as if that data was part of the data/device-derived events from the wearable device. Further, the information exchanged between the wearable device and the DMS and with third-parties and (as well as with third-party devices) may be performed with industry-standard security, authentication and encryption techniques.

The Wearable Device

FIG. 1 is an overview of wearable device 101 and its components according to some aspects of the disclosure. Wearable device 101 may include several internal components, such as, e.g., ultra-wideband transceiver (UWB) and other sensors described herein at least in FIGS. 13-17. The sensors are represented in FIG. 1 as classifiable into various sensor types shown as Sensor Types A-F 110, 111, 112/113, 114, and 115. Although not shown separately in FIG. 1, the sensors are referred to at times herein as N1 to Nm, with "m" being the total number of sensors included in wearable device 101.

As shown in FIG. 1, wearable device 101 includes a processor 100 (or multiple processors as known in the art) with firmware 102, an operating system 103, and applications 104. The wearable device 101 may also include a storage 105 (e.g., a solid-state memory, Flash memory, hard disk drive, etc.). The wearable device may further include one or more an RF radio, a Wi-Fi radio, a Bluetooth radio, and/or a cellular radio transceiver 107. The wearable device 101 may further include a local input/output connection (e.g., USB, optical, inductive, Ethernet, Lightening, Fireire, status light or display etc.) 108, and a battery 109. For purposes herein, local input/output connection 108 and the radio transceiver(s) 107 are generally considered "outputs" though which information may be communicated to an owner or veterinarian directly (through sound emitter/status light/display 604 of FIG. 6), directly to a smartphone (via cellular, Bluetooth, or Wi-Fi or other communication pathways) or though the DMS.

With respect to sensor types A-F, sensor type A 110 refers to the types of sensors that have a sensor input 116 and no other internal components (e.g., simplistic photodiode). Sensor type B 111 refers to a sensor with a sensor input 117 and a processor 118 and storage 119 contained within the sensor type B. Here, sensor type B 111 may store data (at least temporarily) from sensor input 117 and process the data to provide a more meaningful result to processor 100. For instance, sensor B 111 may be a UWB device for monitoring cardiac activity and the like based on movement of a dielectric material (e.g., a heart muscle or other muscle). Processor 118 may control the operation of the UWB and interpret the results. In addition to monitoring cardiopulmonary activity, the UWB componentry may be used for core temperature determinations and as a communication transceiver for communication with a network as known in the art for short distance, high bandwidth communications.

Further, as shown by dotted line 113, storage 119 may optionally be associated with storage 105 to the point that processor 118 writes directly and/or reads directly from storage 105 (as being shared between processor 100 and processor 118). Raw data from sensor types C 112 and sensor types D 113 are processed by preprocessor 120 before the data being sent to processor 100. Preprocessor 120 may be any type of known processor that corrects/adjusts/enhances data. For instance, preprocessor 120 may be an analog to digital converter, an analog or digital filter, a level correction circuit, and the like. Sensor type E 114 includes any sensors not specifically identified above that provide results from radar-based signaling (including RF signal strength sensors, Wi-Fi IP address loggers, and the like).

Finally, sensor type F 115 includes battery sensors that provide data regarding the charge level and temperature of the battery 109.

Inputs to the Wearable Device

Processor 100 may be any known processor in the art that performs the general functions of obtaining content from various sources in forwarding it through communication interfaces. The processor 100 may also perform specific functions as described herein. The communication interfaces may include one or more of microwave antennas, an RF antenna, and RFID antenna a cellular radio transceiver, and known hardware interfaces (for instance, USB). For example, processor 100 may direct the transmission on demand of data collected from one or more sensors due to an episodic event or may direct the transmission according to a predetermined schedule or when eventually connected to the DMS where the data is collected in an off-line mode.

With respect to the off-line mode of operation, processor 100 receives raw data from the various sensor types A-F 110-115. Next, depending on the sensor and its current profile and/or operating mode, processor 100 stores content relating to readings from the sensors. In a first example, processor 100 merely stores all raw data from the sensors. In a second example, processor 100 only stores indications that a sensor has provided a reading outside of a normal range. The normal range may be set by the current profile and/or operating mode and may include one or more thresholds for each sensor signal. For instance, an ambient temperature sensor may have upper and lower thresholds of 28° C. and 15° C., respectively. If a reading from the ambient temperature sensor passes one of these thresholds, that event is stored by processor 100 and storage 105 identifying that the ambient temperature exceeded the identified temperature range. In this example, either a binary indication that the temperature range has been exceeded or the actual temperature may be stored in storage 105. Further, to assist with subsequent analyses by the wearable device 101 or analyses performed by the DMS or third parties, processor 100 also timestamps the indication that the temperature has left the identified temperature range. In a third example, processor 100 may store in storage 105 both the raw data from the sensor leaving and identified range as well as the indication that the identified range has been exceeded. For instance, the indication may be one or more flags stored in storage 105 is associated with the sensor reading, the timestamp, and that the range has been exceeded.

In a further example, processor 100 may operate in a low-power mode when, for example, sensor F (the battery sensors 115) identify that the battery is too hot and/or the battery is running low on available power. In this example, sensors that require significant power may be disabled or activated less frequently until the power level has been restored or battery recharged.

Further, processor 100 may accept new software updates and change sensor thresholds, settings, etc., per instructions received from the data management system DMS. The DMS is described below with reference to FIG. 3. In addition, the owner may modify the thresholds to minimize when he is alerted to various sensor readings from the wearable device. This may be permitted or restricted as minimizing some sensitivity may endanger the animal when the owner should be alerted.

In some embodiments, wearable device 101 may be associated with a base station (not shown). The base station may be capable of charging the battery 115 of the wearable device 101. Further, the base station may emit a steady beacon signal to wearable device 101 (but optional does not receive communications back from the wearable device 101). In some embodiments, the base station may be paired to a plurality of wearable devices 101 (e.g., each worn by each one of a common pet owner's animals). In such embodiments, as known in the art with pairing of wireless devices, each wearable device 101 may be paired to the base station at the time of activation through a unique signal signature. Additionally, in some embodiments, each wearable device 101 may be paired to multiple base stations. One of the benefits of using multiple base stations is that, by comparing the relative strengths of signals from the different they stations, the wearable device 101 may be able to generally identify its location relative to the base stations (e.g., via triangulation).

Optional Location Determination

In some embodiments, wearable device 101 may include a GPS receiver 106 as one example of a sensor. The GPS receiver 106 may turn on once a beacon or other RF signal drops below a threshold level, in response to a sensed episodic event, on demand, or according to a predetermined time schedule. Accordingly, the GPS receiver 106 may not be "always on" (and thus may not, e.g., consume power when GPS readings will not be helpful). By way of an example, if the signal strength of a beacon from base station is high, then the wearable device 101 (and accordingly an animal wearing wearable device 101) may be assumed to be located near the base station and thus the GPS coordinates of the animal may not be beneficial to, e.g., the animal's owner. Accordingly, the GPS receiver 106 may remain in an "off" state (e.g., powered down state) until, e.g., processor 100 instructs GPS receiver 106 to turn "on" (e.g., when the signal strength from the base station becomes weak or nonexistent).

The GPS receiver 106 may provide any useful information regarding the status of an animal wearing wearable device 101 including location coordinates of the animal, elevation of the animal, specific satellite acquisition status, and the orientation of satellites. Some or all of this information may be used in sensor logic calculations and reduce GPS thrashing (continuous attempts to acquire signals and thereby draining the battery).

The processor 100 may use location information from the GPS receiver 106 to identify a geo-zone (also refer to as a geo-fence) and determine when the wearable device 101 has left that identified area. For example, when an animal wearing the wearable device 101 is playing off leash in a park, the animal's owner (using, e.g., a personal mobile device), the DMS, or other may prompt the GPS receiver 106 to create an instant geo-zone around the location of the animal wearing wearable device 101. Accordingly, if the pet wanders too far (e.g., outside of that geo-zone), the owner (via, e.g., a signal sent from cellular radio transceiver 107 to a personal mobile device), the DMS, or other may be notified that the pet has traveled outside of the geo-zone.

In embodiments where wearable device 101 is associated with a base station, processor 100 may determine when, e.g., an RF beacon signal, Wi-Fi signal, Bluetooth signal, or other RF technology signal emitted from the base station drops below a threshold level and, in response, may obtain the location of the device from a GPS receiver 106 and record and/or transmit the location of the wearable device 101 via a cellular radio transceiver 107, Wi-Fi, Bluetooth, or other technology to a pet owner or veterinarian. Thus, according to one aspect of the disclosure, a location of an animal wearing the wearable device 101 may be easily determined when the animal strays too far from the stationary base station. For non-cellular based radios, if the signal strength falls below a certain threshold or is non-existent, processor 100 may change the transmitting profile of the different modems to make them easier to either locate or connect to various available networks or by a mobile device based application being used as directional finder.

In embodiments which include a base station, the health-monitoring system may further interpret readings coming from base station as described herein. For example, signal strength of a beacon coming from the base station and received at wearable device 101 may be compared to a set of thresholds that have been set by the user or defaults provided/derived by the DMS during setup based on high, medium, and low settings. In some embodiments, during activation of the device and after the owner has set up the base station inside their premises, the user may use a companion application (e.g., smartphone application) and walk around her property holding the wearable device and geo-tag important features of her enclosure/yard/field, etc. At each location the GPS coordinates and beacon signal may be logged and uploaded to the DMS to assist in deriving the optimal safe proximity and geo-zones. The owner may also acquire several other base stations that can be placed in other locations that the animal frequents (e.g. weekend properties, pet sitter, etc.) or placed in several locations of a large and evenly shaped property to create proximity zones of unique shapes.

Wireless Communications

The cellular radio transceiver 107 may be used as one means of transmitting and receiving data at the wearable device 101. In some embodiments, the cellular radio transceiver 107 may provide presence information on a cellular network and/or signal strength readings to assist in the wearable device's 101 logic calculations to prevent thrashing (continuous attempts to acquire signals). Further, the cellular radio transceiver 107 may provide real-time clock adjustments, and may be used for cellular triangulation by the DMS when GPS signals are not available or are at or below a usable threshold.

Inputs to the Wearable Device

Figure 2:
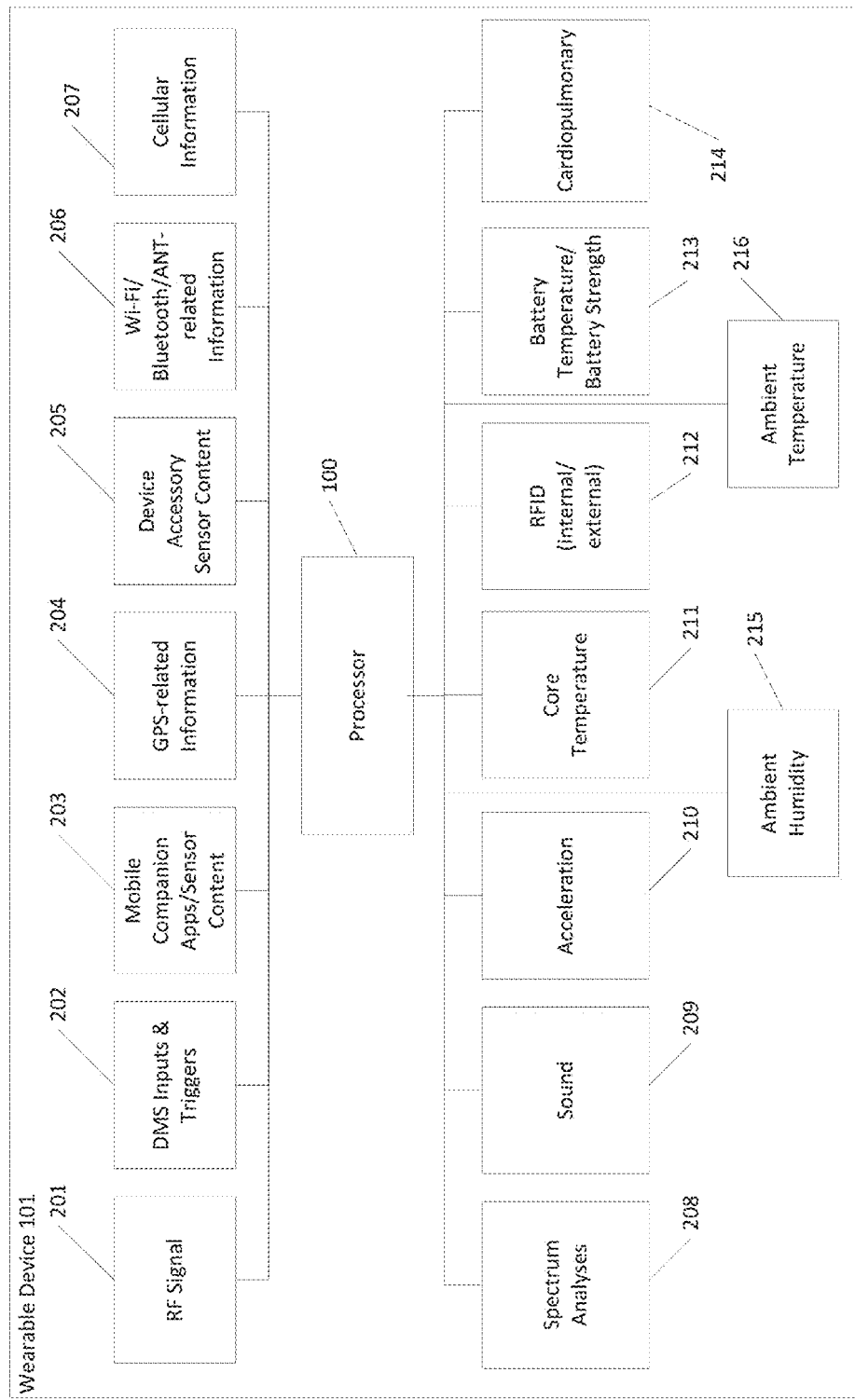
FIG. 2 is a functional block diagram illustrating the various types of information received by the wearable device of FIG. 1.

FIG. 2 shows an illustrative example of various inputs usable by the wearable device 101. FIG. 2 shows RF signal 201, DMS inputs & triggers 202, content from mobile companion apps/sensors 203, GPS-related information 204, device accessory content 205, Wi-Fi/Bluetooth/ANT-related information 206, cellular information 207, spectrum analyses 208, sound levels or actual recordings of sound 209, acceleration 210, core temperature 211, RFID (relating to internal/external RFID-radios) 212, battery temperature/battery strength 213, cardiopulmonary 214, ambient humidity 215, and ambient temperature 216.

The RF signal 201 may receive signals including adjustable settings and options for, e.g., geo-tagging the boundaries of a pet owner's property, etc. as described above with respect to the beacon signal. In addition or instead of RF antenna 109, wearable device 101 may include Wi-Fi, Bluetooth, and/or other RF technologies 206. The Wi-Fi/Bluetooth/ANT-related component 107 is intended to cover local, radio-based communication systems from body-worn to body-wide area networks.

Each may be used in conjunction with a GPS receiver 106 and/or cellular radio transceiver 107 or as a replacement to provide two-way data transmission through paired access points as well as provide presence, proximity, and retrieve time of day information identifying the general location of the wearable device 101.

Wearable device 101 may further accelerometer providing the acceleration signal 210. The accelerometer may be used to report levels of specific activities of an animal. For example, readings from the accelerometer may be interpreted as the animal being currently engaged in walking, running, sleeping, drinking, barking, scratching, shaking, etc. The accelerometer may also be used to report the possibility of a high impact event as well as corroborate and/or augment other sensor readings. In some embodiments, the accelerometer may be used to control other sensors (e.g., turn on, turn off, leave a breadcrumb, ignore a reading, etc.). Further, the accelerometer may be used to determine which of a plurality of animals is actually wearing the wearable device 101. For example, if a pet owner uses a wearable device 101 interchangeably among more than one of her pets, a set of specific attributes pertaining to one of the animals may be created and stored in storage 105 for each pet. Some of the stored attributes may be accelerometer data, such as a particular animal's gait, and other attributes such as bark sound signatures. These stored attributes may then be used to determine which pet is wearing a wearable device 101 by comparing currently sensed attributes to stored attributes.

Another sensor usable with the wearable device 101 is a light meter. The light meter provides the spectrum analyses 208 input of FIG. 2. In a simplistic example, the light meter may be tied solely to presence or absence of a threshold of visible light. In a more sophisticated example, the light meter may be frequency-specific in its readings such that it can separately detect levels of infrared light, visible light, and ultraviolet light. Both of these examples of light meters of varying sophistication are known in the art. In this environment, the processor 100 uses signals from the light meter (or light meters) to determine if the wearable device 100 is located inside or outside. For instance, while a visible light level of a given intensity may indicate that the wearable device 100 is located under a bright light source (e.g., in a sunny area), processor 100 may compare the current infrared and/or ultraviolet light levels against the visible light levels. Accordingly, if the visible light level is high and the infrared and/or ultraviolet light levels are also high, then processor 100 determines that there is a likelihood that wearable device 101 is located outside in the sun. Alternatively, if the visible light level is high while the infrared and/or ultraviolet light levels are low, then processor 100 determines that there is a likelihood that wearable device 101 is located indoors (albeit in a sunny spot).

Further, the light meter may also be used to interpret light levels in determining a current state of an animal to confirm or corroborate a current state of an animal. For example, in some embodiments extremely bright light incidences may be indicative of the animal wearing wearable device 101 being caught in a car's headlights, or being around gunfire, explosions, etc. as based on the sudden change in received light levels 208. Identification of being caught in a car's headlights may be based on a sudden spike in ambient light at night while the accelerometer indicates minimal movement before and after the spike in visible light. Further, a location determination (for instance, from a GPS receiver) may be used in place of or in addition to the accelerometer signal as augmenting the determination of whether the animal has been illuminated by oncoming headlights. Similar spikes in audio signals occurring within a short time of visible light spikes may be interpreted as being around the gunfire, explosions, etc.

More advanced uses of spectrum analysis include the ability to detect trace chemical signatures present in the animal's environment, emanating from their skin/fur, orifices, and/or present in their breath. For example, readings could indicate dangerous environmental conditions (e.g. high readings of chorine), skin related issues (e.g. yeast), and internal related conditions (e.g. ketones in the animal's breath that may be exhibited before other symptoms are evident). Further, the spectrum analysis sensor may also be sniffing for chemical signatures. Combining the detection of sulfur with light and sound spikes helps corroborate the determination that the animal has recently been located near gunshots or other explosions.

An ambient temperature sensor providing the ambient temperature 216 may also be provided as another example of a sensor. The ambient temperature sensor may be used to determine a location of an animal wearing wearable device 101 (e.g., indoor versus outdoor). In some embodiments, the processor 100 tracks ambient temperature 216 over time and determines a current rate of change. If that current rate of change is greater than a predetermined rate as existing for a period of time, processor 100 identifies the rate of change is a prediction that the animal wearing wearable device 101 will be overheating or freezing in the near future. Further, in some embodiments an ambient temperature sensor may be used to corroborate or control other sensors.

The wearable device 101 may also include a humidity sensor providing the ambient humidity input 215. In some embodiments, the humidity sensor may be used to adjust sensed temperatures to wet bulb settings. These wet bulb settings may be important in calculating animal heat loss/gain and may be used in roughly identifying a location of the animal (e.g., inside or outside). Further, the excessive humidity or dryness identified as signal 215 from the humidity sensor may be combined with a temperature reading to determine the heat index or wind chill.

Further, a microphone or peak noise detector sensor may provide sound input 209. The microphone/peak noise sensor may be used to, e.g., measure specific sound events (barking, etc.) and may be used to corroborate other sensor readings. For example, in embodiments where a light meter indicates, e.g., an animal wearing wearable device 101 may be caught in a vehicle's headlights; a microphone sensing a load noise may be interpreted as, e.g., an impact event (getting hit by the vehicle). A specific method of determining an impact event is described herein.

Another example of a sensor may be an internal battery strength and/or battery temperature sensor 213 providing information regarding the strength and/or temperature of the battery. The internal battery strength and/or temperature sensor may be used to either modulate certain other sensing activities and/or as an input source to other sensing activities. For example, in response to sensing the internal battery is running low, GPS acquisition duty cycles and/or cellular transmissions may be reduced to conserve power to extend the operation of the wearable device 101.

A core temperature sensor providing core temperature 211 may be provided as another example of sensor. The core temperature sensor may be used to non-invasively measure the core temperature of an animal, and thus provide data relating both to a real-time core temperature of an animal and an animal's change in core temperature over time.

The wearable device may also include one or more antennas as tied to one or more of the internal radios/sensors. One of the internal components attached to the antennas may be a UWB device. As known in the art, UWB device is used to monitor various conditions (e.g., used in fetal monitoring, cardiopulmonary monitoring, and the like). Here, the UWB device may be used to monitor a variety of different conditions. For example, in some embodiments, the UWB device may be used to transmit and receive UWB signals to non-invasively monitor operations of an animal's heart. Signals from that monitoring operation are then processed by processor 100 to determine if an episodic event has occurred (e.g., an abnormally high heart rate), if a more complex event has occurred (e.g., heat exhaustion after excessive running) and if the cardiopulmonary system of the animal is trending toward an undesirable condition (e.g., an increasing average heart rate). Here, in addition to an average heart rate, a statistical deviation may also be provided. In this regard, statistical deviations may accompany other average rates as forwarded to veterinarians and possibly owners.

Specifically, the UWB device may be used to measure stroke volume and a relative change in blood pressure of an animal wearing wearable device 101. For purposes herein, stroke volume readings from the UWB are useful in addition to vital sign readings. In other embodiments, the UWB device may be used to determine if the wearable device is actually on the animal. In some embodiments, a profile (e.g., stored characteristics) of an animal may be available for more than one animal which wears the wearable device 101. In such embodiments, the UWB device may be used to determine to which animal the wearable device 101 is currently attached. For example, readings at the UWB device may be compared to stored cardiopulmonary profiles to determine which of a plurality of animals is currently wearing the wearable device 101. Further, the UWB device may be used to interpret changes in the neck tissue as indicative of an animal eating, drinking, and/or vomiting. Further, the UWB device may be used to interpret signals in the abdomen area to investigate the possibility of obstructions in the digestive track.

Any other desirable sensor may be provided as a component of wearable device 101 in order to measure one or more attribute of an animal and/or its environment. Those skilled in the art, given the benefit of this disclosure, will recognize numerous other sensors which may be incorporated into wearable device 101 without departing from the scope of this disclosure. Further, the components and/or sensors contained within wearable device 101 may share some common circuitry such as power supply, power conditioners, low pass filters, antennas, etc., as well as share sensing data with each other to derive more meaning from combined data sources.

According to some aspects of the disclosure, the wearable device 101 (and associated base station(s), if any) and the DMS may form part of a health-monitoring system used to collect data about and/or monitor specific health attributes of one or more animals. Further, in some embodiments, one of more of sensors may have the capability of activating, deactivating, controlling, rejecting, accepting, or throttling another sensor's activities as described herein. In addition, the health-monitoring system may include both passive and active sensors and multiple antennas that generate and receive a wide variety of electromechanical energy whereas the normal output of one or more components may enhance the capability of another component in a derived fashion.

The health-monitoring system according to some aspects of the disclosure may further include external sensors (e.g., sensors external to the wearable device 101) which interact with or otherwise supplement the sensors of the wearable device 101. In some embodiments, these external sensors may include detachable analog/digital items such as a stethoscope, ultrasound sensor, infrared temperature sensor, pulse oximeter, blood pressure monitoring tool, glucose meter, blood analyzer, breath analyzer, urine analyzer, brain scanner (all which may include additional application software and/or be controlled by the device software), and filters/attachments to enhance/collaborate the existing set of sensors and readings. The individual operations of these separable sensors are known in the art. Here, wearable device 101 provides a platform to which these additional sensors may be connected and their data or analyzed content being stored in storage 105 for relaying to an owner or DMS (or even third parties) as described herein.

In some embodiments, these external sensors may be integrally provided with or associated with other well-known devices. For example, the health-monitoring system may collect data from a camera (with or without lens/filter attachments), microphone, speaker, GPS, and other items that may be plugged into or utilized by the wearable device 101 and/or the health-monitoring system. In some embodiments, these sensors may be part of a personal mobile device (e.g., a smartphone or the like). Each of these external sensors and/or mobile browser applications/installed applications may act independently, in conjunction with the wearable device 101, may be triggered by the wearable device 101, or may be triggered by the DMS on a demand, episodic, or a scheduled basis to provide additional and/or collaborative sensing information that will provide important episodic, derived, or trending information to support the animals safety, wellbeing and health. In addition, all of the above described activities may be triggered by a mobile device and a companion applications and attachments/accessories to provide time stamped correlation of sensor data as described herein.

Further examples of external sensors used in conjunction with the described health-monitoring system may include RFID proximity sensors that communicate with RFID proximity tags and provide RFID content 212. For example, RFID proximity tags may be placed at an animal's bed, at its food bowl, at its water bowl, outside a door frame, outside a gate post, near garbage cans, etc. Thus, when an animal wearing a wearable device 101 is near any of the above items, the wearable device (receiving a signal via the RFID sensor) may interpret that the animal is sleeping, eating, drinking, outside, out of the yard, getting into garbage, etc.

The health-monitoring system may further use owner observations of an animal collected through, e.g., companion web/mobile based applications, telephone call center activity/teleprompts, and the like. The owner observations may corroborate measured events (e.g., events measured by wearable device 101 and/or one or more external sensors) to assist in lowering the ongoing rate of false positives and false negatives. For example, in some embodiments, the health-monitoring system may include a mobile weight/size mobile device application which instructs the owner to wave a mobile camera integral to the mobile device across an animal with a pre-identified marker in the field of view. Pre-processed data derived from this action may then be uploaded to the DMS where conclusions can be derived as to the animal's weight and size. Such data is then appended to the animal's record. Other important owner recorded observations may include observable items such as caloric intake, blood in urine, black stools, smelly breath, excessive thirst, white skin patches around the face, recording the disposition of the animal, and the like. For instance, the caloric intake may be monitored by an owner through an application running on a computer or smartphone in which the owner identifies what food and how much is being consumed over what interval.

Further, the health-monitoring system may include sensors placed internally within an animal (for instance, invasive but unobtrusive sensors). For example, microchips or the like embedded within an animal may provide data relating to, e.g., blood oximetry, glucose monitoring, ECG, EEG, etc.

Data Management System

Figure 3:
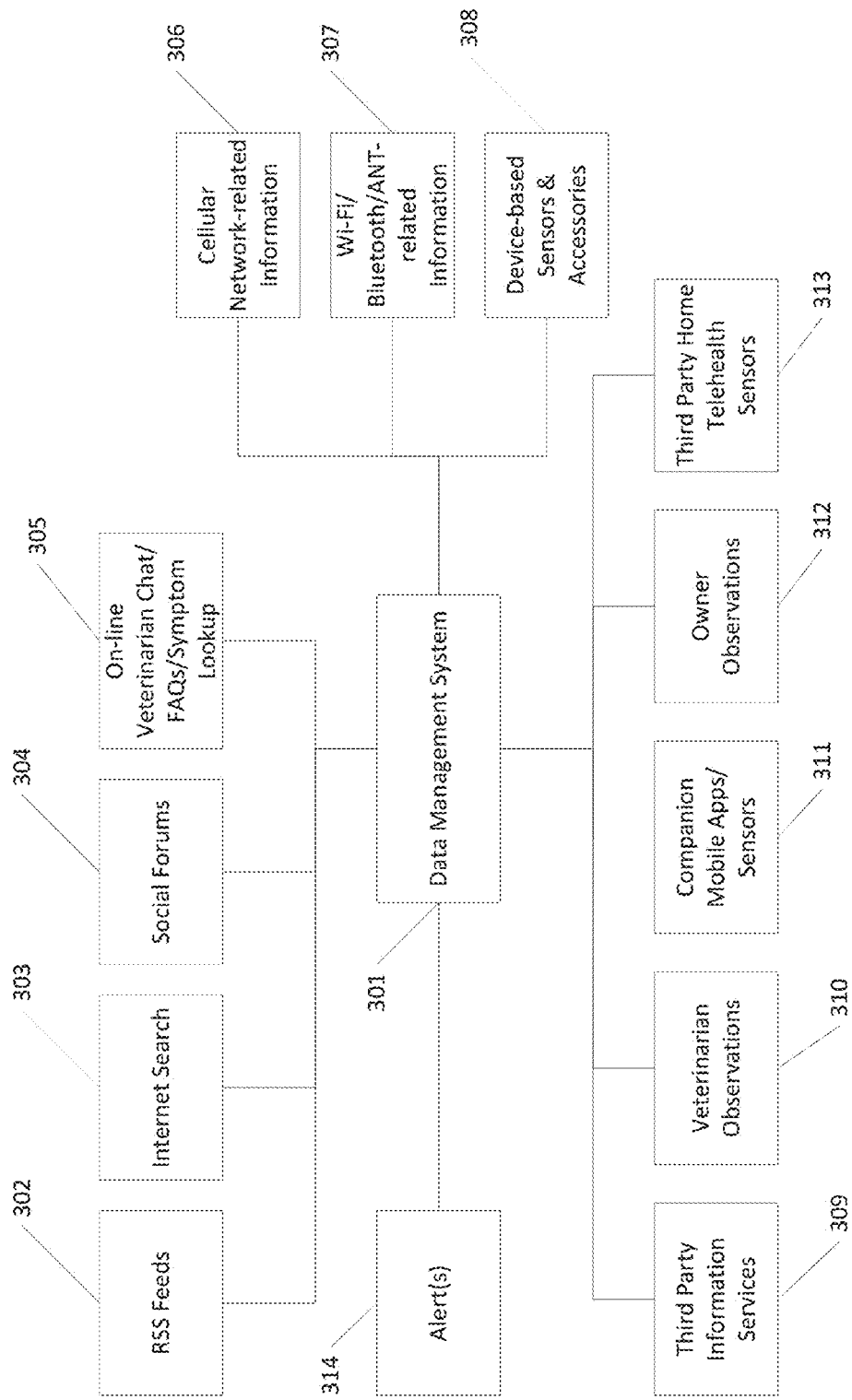
FIG. 3 is a schematic diagram of a data management system and the various inputs thereto used in conjunction with the wearable device of FIG. 1 according to some aspects of the disclosure.

FIG. 3 shows an example of a data management system 301 receiving inputs from a variety of sources. Those inputs may be specific to an individual animal or generally relate to related animals (related by one or more characteristics including breed, age, health condition, and the like). FIG. 3 shows data management system 301 receiving RSS feeds 302, Internet search content 303, social form content 304, content from chats with veterinarians, symptom lookups and the like 305, cellular network-related information 306, Wi-Fi/Bluetooth/ANT-related information 307, wearable device 101-based sensors and accessories 308, third-party electronic services 309, veterinarian observations 310, content from companion mobile apps/sensors 311, owner observations 312, and third-party home tele-health sensors 313.

DMS 301 is a data receiving and processing system that receives data and/or wearable device-derived events from the wearable device 101 and analyzes that content directly, or in conjunction with older data or past analyses of older data from the wearable device, or in conjunction with data from other sources, or any combination thereof. The DMS 301 includes one or more processors, storage, operation software, input/output pathways, and the like as similar to that of the processor 100 and storage 105 of wearable device 101 shown in FIG. 1. Further, the DMS may be a cloud-based computing platform in which communications via the Internet are received in the DMS at a server or other hardware device and processed in accordance with computer-executable instructions and workflows. In this example, the DMS may have industry standard Internet connections, routers, servers, that connect DMS 301 to the various content sources 302-313. Alerts as sent to an owner compared to a veterinarian may be different. Further, even if the sensors are operating as tied to a specific profile, the DMS may continue to separate and forward alerts based on predefined settings at the DMS.

In some embodiments of the disclosure, the health-monitoring system may further collect data using external rich site summary (RSS) feeds 302. For example, the system may receive data about the weather, environment, daily pet health tips, published research data, etc., via the RSS feed 302. According to some aspects, this received data may be used to corroborate, supplement, and enhance data collected from the wearable device 101, other external sources, and the like as discussed herein.

Some embodiments of the health-monitoring system may further receive data from, e.g., non-invasive home telematics solutions 313. For example, the system may receive data from smart mats, smart motion/IF detectors, and other devices prevalent in the marketplace. Pets and animals inside a home may thus trigger these devices and thus record sensor artifacts such as presence, weight, physiological signs, and vital signs. These recordings (which may normally be discarded by the human home monitoring systems) may provide valuable data collection/corroboration points for the system, for example in the DMS (as described herein). Several techniques may be employed to upload this data to the DMS (e.g. companion mobile device application, user-entered readings, Bluetooth, Wi-Fi, other RF technologies, etc.).

When used as part of a health-monitoring system in FIG. 2 and as described herein, the wearable device 101 may be the prime source of sensor collected data (through, e.g., sensors and others described above). All sensors and their inputs may be available to be intelligently combined through data fusion to create meaningful standalone alerts and as an input into the DMS to develop and extract even more meaning from the data.

In some embodiments, the health-monitoring system as described herein may include a DMS 301 remote to the wearable sensor 101 as schematically depicted in FIG. 3. In some embodiments, DMS 301 may receive information from wearable device 101 and/or other sensors. Further, DMS 301 may transmit information to, e.g., a pet owner (via, e.g., a computer, smartphone, tablet, land line, display of wearable device 101, status light/display/sound indicator 604 of FIGS. 6A and 6B, etc.) and/or a veterinarian (via, e.g., a web-based dashboard, facsimile, land line, mobile alerts, etc.). In some embodiments, DMS 301 may transmit data according to predefined criteria. For example, according to some aspects, DMS 301 may transmit information periodically on a scheduled basis. In other embodiments, DMS 301 may transmit information when that information exceeds a threshold value. In still other embodiments, DMS 301 may transmit data on-demand (e.g., requested by a pet owner, veterinarian, or the like).

In some embodiments, DMS 301 may be the data repository of all inputs regardless of the source to derive meaningful/actionable information related to the animal's safety, wellness, and health for owners and veterinarians. In some situations, information specific to the animal wearing the device 101 (e.g., the third-party information service data 309 and the third-party veterinary chat service data 311) may be forwarded from the DMS 301 to the third-party prior to receiving data (307, 311) from the third parties to assist with the third-parties' analysis. The DMS may analyze received data and determine the meaning of the data as DMS-derived events. Next, based on those events, the DMS may obtain recommendations on file from a storage tied to those derived events, compile those recommendations, and provide the compiled recommendations to the owner and/or veterinarian as actionable information. For instance, if the meaningful information is that the animal has gained 5 lbs. in the past week and has exhibited a lower than normal activity rate, the DMS 301 may look up recommendations on file from a storage tied to weight gain and the amount of weight gain and the identified recommendation or recommendations. Next, the results are compiled and forwarded to the owner/veterinarian as actionable information.

In general, the following lists typical inferences that may be reported to owners: the animal is outside of designated safe zones; there is a potential situation where the animal may be overheating or freezing; the animal may have been in an accident (high impact event of various levels of severity); the animal's activity level has been decreasing even after applied filters for owner and pet lifestyle profiles; the animal is limping (based on a change in gait); the animal appears to be in potentially dangerous environment based on extreme noise and light indicators; the animal is very listless during sleep (as an indication of pain, digestive issues, respiration issues, or past physiological trauma); the animal's heart rate variability is abnormal; the animal's respiration rate and quality is abnormal; the animal appears to be in distress/pain (yelps when there is large gross movement); and the wearable device is not on the animal that it was initially assigned to by means of examining its gate profile versus the one on file or other vital sign indicators that are part of their electronic profile.

Typical suggested actions may include to: increase the owner's personal observations of the animal to confirm or dismiss specific developing items of concern; increase/decrease thresholds for items in the animal's sensor profile so they more closely align with the owner's and the specific pet's daily life patterns, age, breed, size, and know medical conditions; increase/decrease the animal's activity; monitor the animal's diet (record caloric intake); remove the animal from a potential developing overheating/freezing situation; monitor the animal for specific coughing sounds; refer the owner to specific related articles/links/videos etc.; consult an optional online "ask-a-vet" services; and to see their veterinarian as soon as possible based on a life-threatening situation.

The following are illustrative examples of triggers that result in reporting issues to the owner: an episodic issue based on a sensor or a group of sensors confirming an event comparing readings to preset thresholds; a time-based analysis (a.k.a a longitudinally-based) on analysis at the device 101 level or the DMS 301 level based on trending positive or negative readings for a particular suspected condition; on the demand of the owner or the veterinarian; periodically to provide a snapshot of the condition of the animal based on the owner or veterinarian's safety, wellness and health goals.

The veterinarian may receive a fewer number of inferences/suggestions and more empirical data based on wellness issues and vital signs that could lead to serious health issues, the monitoring of specific known health conditions, and the monitoring of the effectiveness of prescribed therapies. The veterinarian may receive vital signs and other physiological information that suggests the animal is trending positively or negatively. Items that may act as triggers for the veterinarian to be sent information include an episodic vital sign(s) reading or physiological reading has passed its threshold or a derived vital sign(s) or physiological sign or signs as trended over time have passed thresholds set by the veterinarian.

Also, the veterinarian may be interested in the following current possible vital, environmental, or physiological signs: core temperature; ambient temperature & humidity; and core temperature. The veterinarian may be interested in the following pulmonary information: detected lung motion & measured respiratory rate and rhythm; measured respiration and exhalation times (ti/te); detected asymmetrical respiration (inflammation, obstructions, asphyxiation); measured chest compression rate, depth, and chest recoil; and measured and ongoing monitoring of chronic bronchitis. The veterinarian may be interested in the following cardiac information: detected cardiac motion & measured cardiac rate and rhythm; measured changes in cardiac stroke volume and cardiac output; a comparison of blood pressure to a threshold; signs of developing congestive heart failure; signs of bradycardia and tachycardia; signs of hemo/pneumothorax. Further, the veterinarian may be interested in the following other information: signs of a seizure; uterine contraction rate and intensity; identification of possible sleep problems such as sleep apnea; signs of a foreign body in the animal; long-term sensor data; average and statistical deviation of cardiac activity, respiration activity, and core temperature; activity level; estimated weight; estimated hydration levels; and average daytime/nighttime ambient temperatures. The following are sample inferences that may be derived by the DMS 301 and identified to the owner or veterinarian for diagnosis: heartworm; vomiting & diarrhea; obesity; infectious diseases; kennel cough & other developing respiratory conditions; lower urinary tract infection; dental disease; skin allergies; damaged bones & soft tissue; cancer (for instance, by ketone level changes in the animal's breath); developing heart conditions; distress/pain; and cognitive dysfunction. The following are sample symptoms/ inferences made from a combination of sensor data and veterinarian-supplied data: impact of specific prescribed therapies; recovery status of an animal who has just undergone surgery; and trending of vital signs against a base line determined by the veterinarian.

In such capacities, the DMS 301 may be receiving raw data, pre-processed data at the wearable device 101 level. For example, the accelerometer {x,y,z} g values may be averaged over a fixed window (for instance, a one second window), a deviation of magnitude computed, and a high, medium, or low activity designation may be assigned based on the activity of the animal. Sound files from a separate device, RSS feeds, and other unlike data types need to be catalogued, time stamped, sorted and prepared for analysis. Because the DMS receives these divergent types of data, the DMS 301 may perform these correlations. For instance, the DMS 301 may receive high ambient temperature readings from the wearable device 101 and compare it against expected local temperatures (obtained by RSS feed 302 or Internet search 303) for the current or last identified location of the wearable device 101. If the ambient temperature is high (for instance, over 45° C.) while the predicted high temperature for the location is only 20° C.), then the DMS 301 may derive that the animal is locked inside a car with its windows shut. Based on this derived event, the DMS may attempt to alert the owner as alert 314. The alert 314 may be in the form of one or more emails, SMS or other text messaging systems, social messaging systems (like Twitter and Facebook, etc.) or by calling the owner directly. It is appreciated that the frequency and thresholds for alerts may be fixed or may be configurable by the user.

DMS 301 may also include information about past events, current events, or predictions of possible future events. DMS 301 may also act as the communications hub between the wearable device 101 and third party services, the vet, and/or a pet owner through various communications channels and devices. For example, in some embodiments a pet owner may use her personal mobile device as an input device to record her own observations through free form text or drop down menus (effectively becoming one sensor of the sensory platform) and thus DMS 301 receives these inputs from the owner via the personal mobile device. Each data element stored in the DMS 301 may be meta-tagged so that each stands alone without having to go back to, e.g., an owner/pet profile. Such meta-tags may include a time stamp, geographical data, breed, age, etc., that may facilitate large scale anonymous data analysis.

Neck Placement of Wearable Device 101

Figure 4:
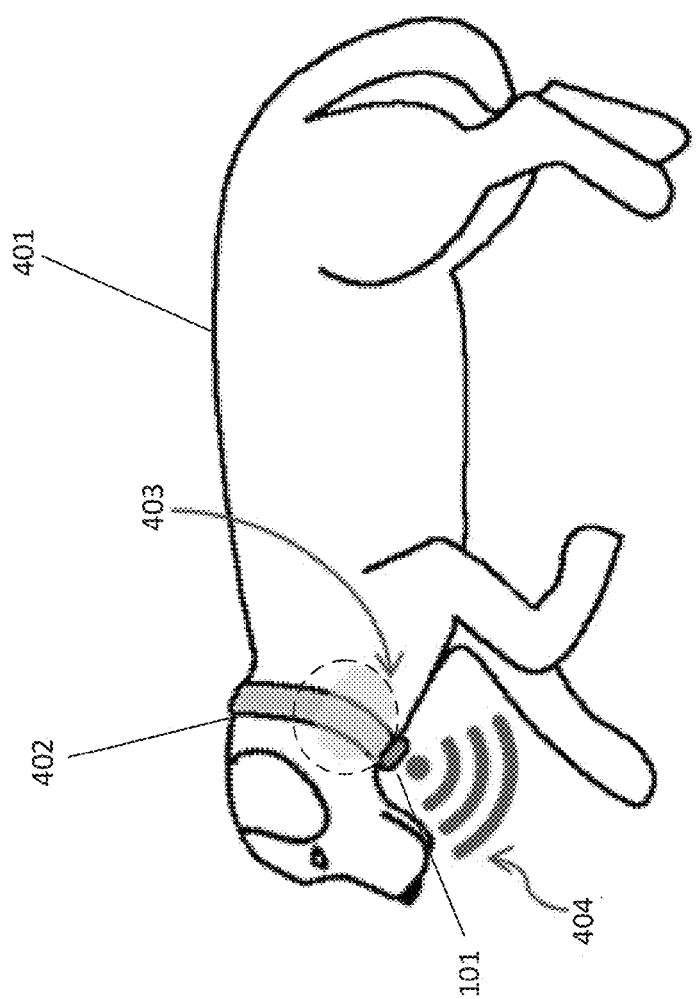
FIG. 4 illustrates a collar incorporating the wearable device of FIG. 1.

FIG. 4 illustrates a collar 402 including wearable device 101 according to one aspect of the disclosure. As depicted in FIG. 4, collar 402 may include wearable device 101 such that the wearable device 101 is positioned near the neck of animal 401. Accordingly, in such an embodiment, sensors receive data near the neck of animal 401 at sensing location 402. Further, wearable device 101 receives and transmits data at transceiving location 404.

Figure 5:
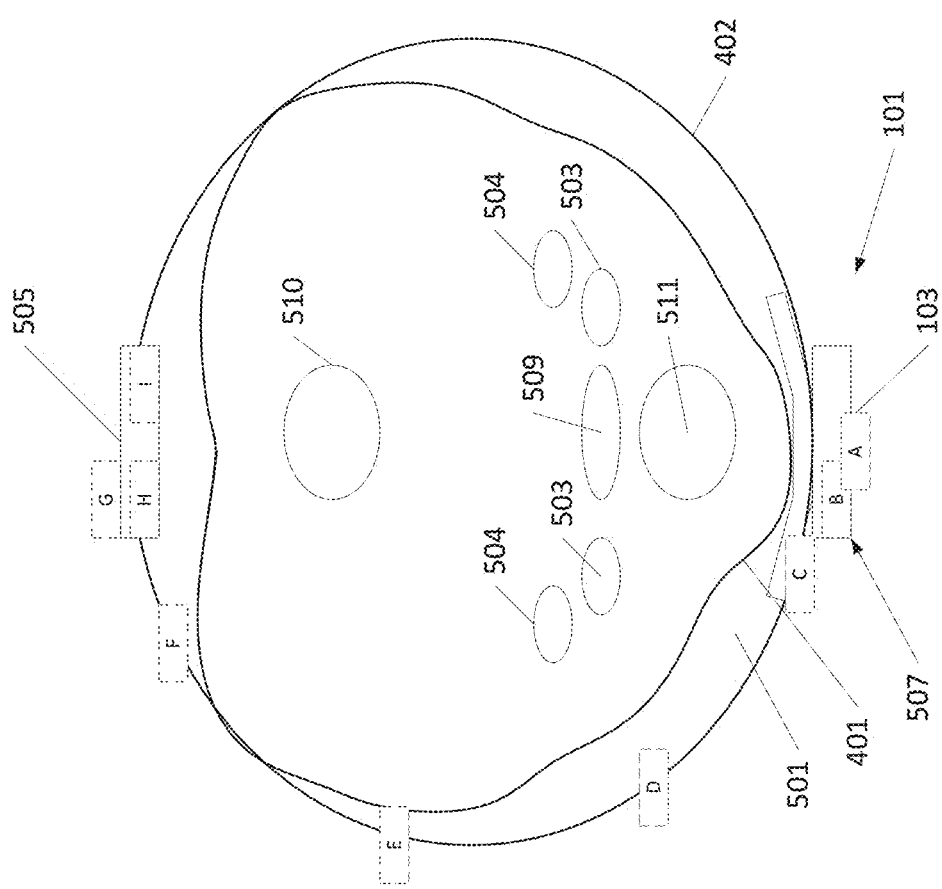
FIG. 5 illustrates a cross-sectional view of an animal's neck wearing the collar depicted in FIG. 4.

FIG. 5 illustrates a cross-sectional view of animal's neck wearing collar 402 including wearable device 101. As depicted, collar 402 may include a clasp 505 that, when clasped, positions wearable device 101 adjacent to fur 501 on the lower side of animal's neck. FIG. 5 depicts approximate locations of the structures within the animal's neck. Specifically, FIG. 5 shows carotid arteries 503, jugular veins 504, esophagus 509, trachea 511, and spinal column 510 in relation to the wearable device 101. In such a configuration, antennas of the cardiopulmonary (e.g., UWB device) and other inward-looking components (e.g., ECG and ultrasound probes) contained in wearable device 101 are placed on the inside of collar 402 while processor 100, other sensors, and other components (e.g., RF antennas 109, RFID antennas 111, etc.) are located on the other side of collar 402 (for instance, at location 507). Further, the outward looking antennas may be located at any of locations A-I to help minimize interference with the inward-looking antennas. Alternatively, sensors located at locations A-I may have improved readings by separating them from interference with contact with the animal. For instance, if the ambient temperature sensor was placed at location A, there is a potential for errant readings when the animal is laying on its chest and wearable device 101 is resting on the animal's paw. Locating the ambient temperature sensor at an alternative location, for instance, D-I, may improve the reading from the sensor as it would be spaced from the animal's paw when the animal is laying in this position. Further, in an alternative example, various sensors may be replicated around the collar 402 and their readings averaged or the highest and lowest readings dropped to reduce the influence of aberrant readings.

As shown in FIG. 5, wearable device 101 is able to receive and transmit information on the outside of collar 402, while keeping inward-looking antennas near animal's skin on the inside of collar 402 such that accurate readings from, e.g., the animal's carotid arteries 503 and/or esophagus 509 may be obtained. Alternatively, readings may be obtained from jugular veins 504 instead of or in conjunction with carotid arteries 503. Other tissue movement may also be of interest including muscle movement surrounding the trachea (as the trachea's cartilage may not be reflective of some dielectric signals and not detectable directly).

Figure 6A:
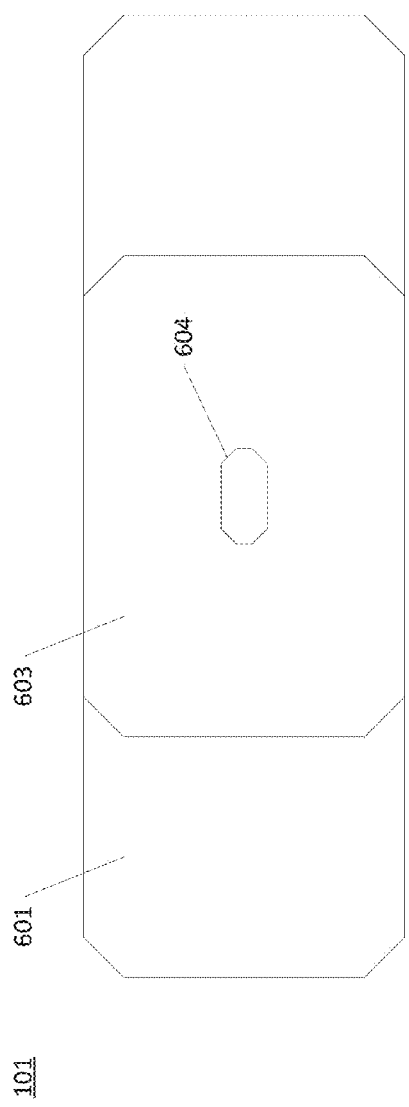
FIGS. 6A and 6B illustrate top and side views of an embodiment of the wearable device of FIG. 1.
Figure 6B:
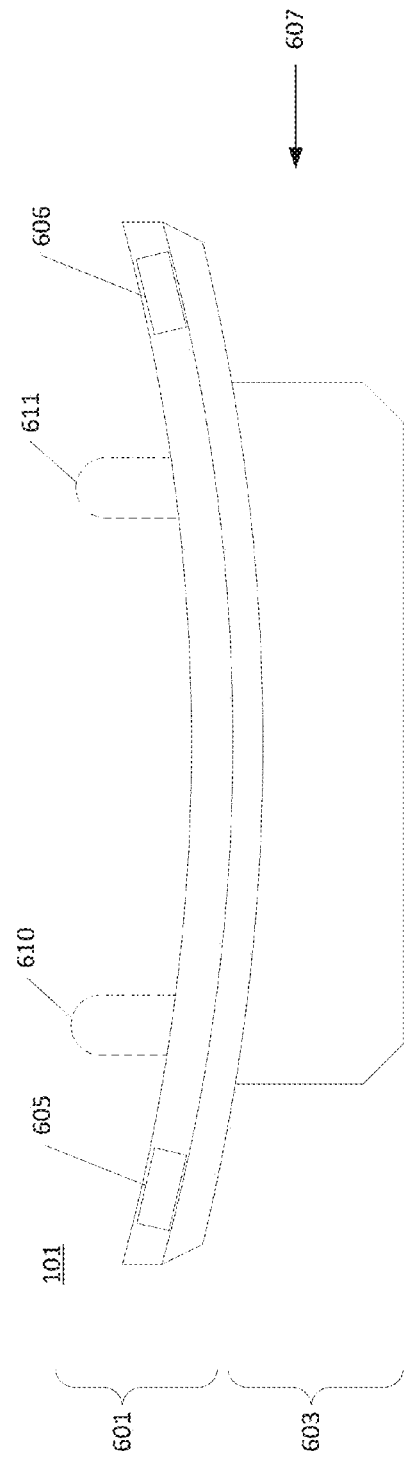

The configuration of wearable device 101 according to some embodiments of this disclosure may be more readily understood with reference to FIGS. 6A and 6B. FIG. 6A illustrates a top view and FIG. 6B illustrates a side view of an embodiment of wearable device 101. In the embodiment of FIGS. 6A and 6B, wearable device 101 may include two portions: an inside portion 601 and an outside portion 603. Inside portion 601 may include the inward-looking antennas such as the UWB antennas, microwave antennas, or ultrasound antennas. For instance, the antennas may be located at locations 605 and 606. Outside portion 603 may include other components such as processor 100 and the other components of FIG. 1 including outward-looking antennas. In one example, the inward-looking antennas of portion 601 may be shielded from the outward-looking antennas of portion 603 by a metal or metallized layer or other known antenna isolation material to minimize interference between the different sets of antennas. Further, status information including on/off status may be provided to the owner via status light 604. Status light 604 may be a simple LED or may include a display screen and touch interface configured to display content to an owner as opposed to (or in addition to) sending the information to the DMS to then be forwarded to the owner's smartphone. In addition, 604 may be a sound generator that responds to setting changes.

When wearable device 101 is placed on an animal, such as shown in FIG. 5, the inward-looking antennas will be located near the animal 401 (e.g., inside of collar 402) and thus provide accurate sensing, while other components, including some components used to transmit and receive data, may be placed away from animal 401 (e.g., outside of collar 402) such that transceiving capabilities of the outward-looking antennas are not degraded by the operation of the other antennas.

Further, metal or metallized probes 610 and 611 may be used to establish probe-to-skin contact for sensors that may be improved with direct skin contact. These types of sensors may include skin temperature sensors, heart rate sensors, and ECG sensors. With respect to temperature sensors, these probes may be attached to one or more heat-sensing components (or may include those heat-sensing components. The heat sensing components may include thermistors, thermocouples, and the like and combinations thereof.

Chest Placement of Wearable Device 101

Figure 7:
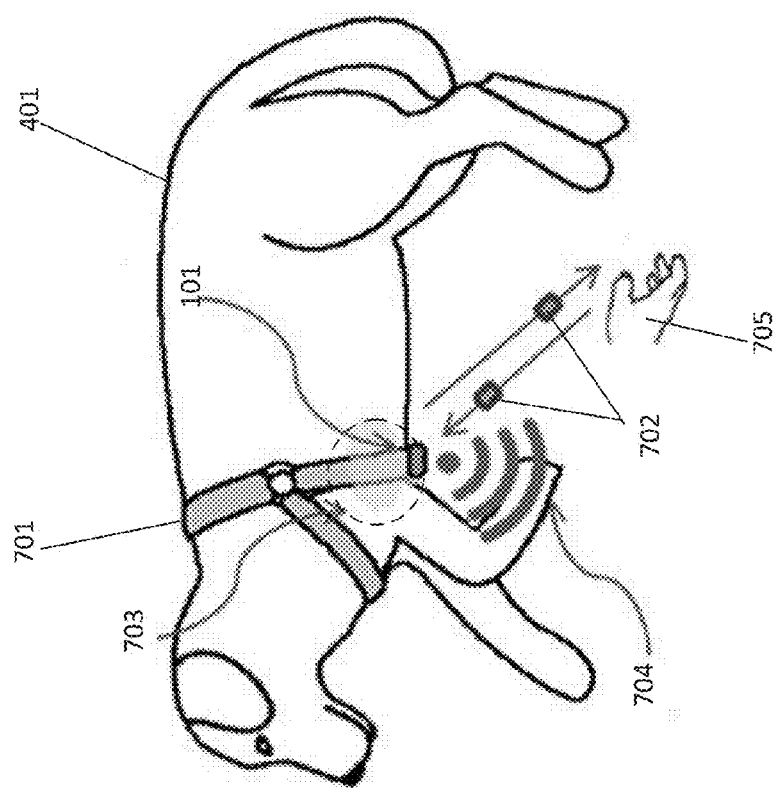
FIG. 7 shows a harness incorporating the wearable device of FIG. 1.

In other embodiments, wearable device 101 may not be worn around a neck of an animal 401, but rather may be worn at any suitable location for receiving information by the sensors. For example, and as illustrated in FIG. 7, wearable device may be provided as part of a harness 701 worn around animal chest. In such an embodiment, sensing location 703 and transceiving location 704 will be near animal's chest rather than near animal's neck (as depicted in FIG. 4). Regardless of the particular location of wearable device 101 (at the neck location or chest location, batteries 115 and other detachable components may be removable and replaceable by a pet owner 705.

Operation of Sensors

FIGS. 8-12 and 22 relate to flowcharts showing processing of the wearable device 101 and/or DMS 301. These flowcharts are used to explain various aspects of analyzing signals from one or more sensors. It is appreciated that other types of analyses based on the sensor information are possible in place of threshold comparison. Other known techniques include Bayesian inference analysis, neural networks, regression analysis, and the like and their use to analyze the signal inputs are encompassed within the scope of this disclosure.

Figure 8:
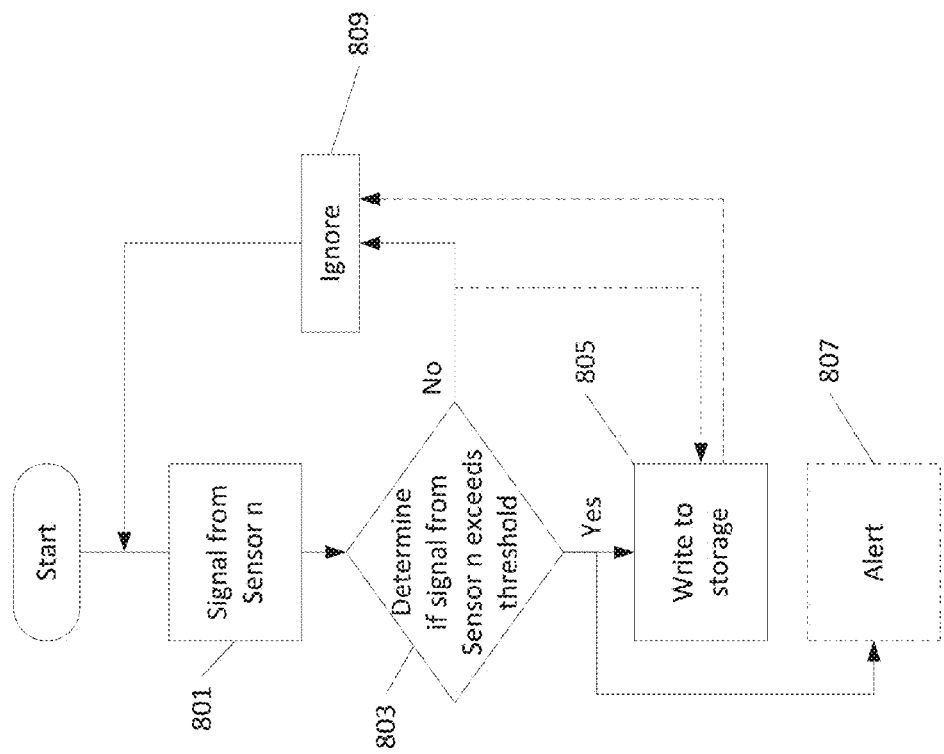
FIG. 8 is a flowchart depicting basic sensor processing according to some aspects of the disclosure.

Turning now to FIG. 8, a flowchart representing basic sensor processing (e.g., processing of one or more internal sensors, external sensors, internal sensors, and/or other sensors) is depicted. A sensor processed as shown in FIG. 8 may be one that is either on all of the time, interrupt driven, or triggered on demand. At step 801, sensor data is received from sensor n. Again, this sensor data may be continuously received (e.g., always on), may be triggered by another sensor's reading (e.g., interrupt driven), or may be received in response to a pet owner, veterinarian, or the like requesting sensor data (e.g. on demand). At step 803, the sensor data is compared to a threshold value. At step 803, the relationship of the compared data to the threshold value may be such that nothing of interest is happening. In such a situation, the data may be ignored as indicated by step 809, and the method will return step 801 to receive additional data. However, if the compared data exceeds the threshold, this occurrence is written to storage in step 805. Optionally or in addition to step 805, an alert may be provided to a pet owner or sent to the DMS as shown in step 807. The alert may be local (e.g., an audible alarm on the wearable device 101) and/or may be remote (e.g., on a pet owner's personal mobile device, within a veterinary dashboard, etc.). In a further modification, the fact that the signal from sensor n did not exceed the threshold may also be stored as shown in broken lines from the NO output of determination step 803 to the ignore step 809 as a positive indication that the reading was within the threshold. Further, the series of store ratings provide a breadcrumb data set of incremental changes that may be usable by the DMS.

Figure 9:
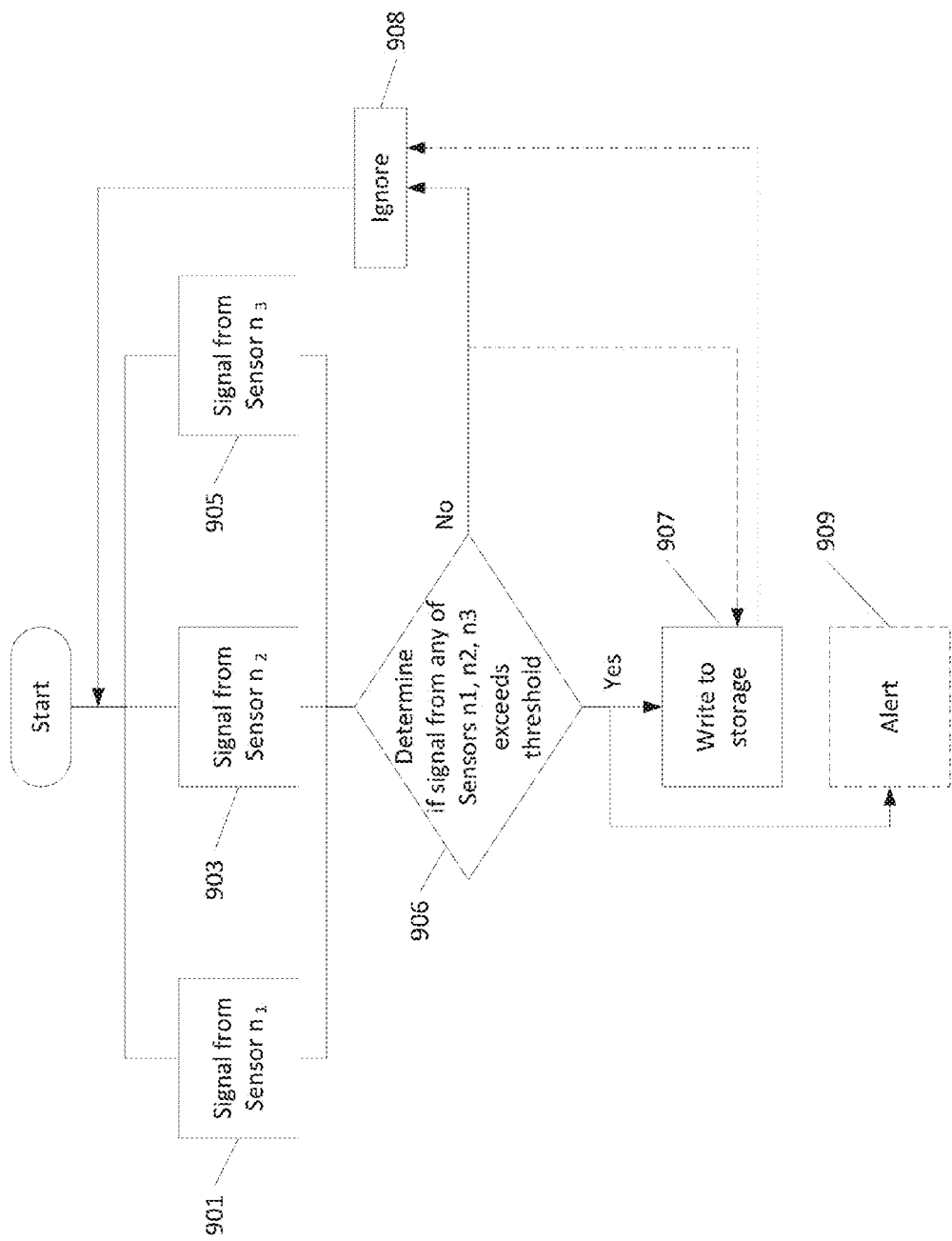
FIG. 9 is a flowchart depicting processing of more than one sensor according to some aspects of the disclosure.

FIG. 9 depicts an embodiment where readings from multiple sensors {n1, n2, and n3} may be used to determine a status of an animal. Again, each of the sensors in the diagram may be constantly on, interrupt drive, or triggered on demand. At steps 901, 903, and 905, data is collected from each sensor n1 through n3. As discussed, the sensors may be located in wearable device 101 and/or external devices (e.g., smartphone, RSS feed, etc.). Any one of sensors n1, n2, and n3 may individually trigger an alert condition in step 906, and written to storage in step 907 and (optionally) the alert provided to the owner or DMS in step 909. Otherwise, the determination is ignored in step 908. Similar to the process of FIG. 8, data may be breadcrumbed despite the sensor readings not exceeding a threshold as shown in the broken lines from step 906 to step 907 and then back to step 908.

Alternatively, step 906 may require a consensus of all three readings a weighted basis is needed to either confirm an alert condition or ignore the sensed the data. For example, at step 907, in response to one or more of sensors n1, n2, and/or n3 triggering an alert condition at steps 901, 903, and/or 905, respectively, a combination of the sensed data from each sensor is compared to one or more thresholds to determine if, e.g., an alert condition is present. Further, at step 907 the sensed readings may be compared to past readings that are either stored locally (e.g., within wearable device 101) or stored, e.g., in the DMS 301. Thus, using the sensed data from multiple sensors (in the depicted embodiment, n1 through n3), inferences regarding animal and pet safety, wellness, and health may be formed at step 907 based on analysis of the sensor's readings and/or, e.g., breadcrumbs (time-stamped recordings). If the combination of the sensor data triggers an alert (e.g., if the combination of data confirms an alert condition), the alert may be returned at step 909 (to, e.g., a pet owner and/or veterinarian, etc.). However, if the combination of sensor data does not trigger an alert after being compared to one or more thresholds, the data is ignored at step 908 and the method returns to steps 901/903/905 to receive further data. In any event (e.g., alert or ignore) the readings and results may be written to local storage at step 907 for subsequent upload to the DMS 301.

The analysis of the sensor data at step 803 or the multiple sensor data at step 907 may be performed in any suitable location within the system. In some embodiments the analysis may be performed in the wearable device 101. In such embodiments, wearable device 101 may perform episodic data analysis (e.g., independent intelligent decisions) as well as longitudinal data analysis. For the latter, the wearable device may monitor a number of recorded breadcrumbs of various events over time. For example, the wearable device 101 may monitor the animal's temperature over time in order to monitor the animal's condition in compliance with FAA regulations on pets stored in cargo holds. In other embodiments, the wearable device 101 may monitor the animal's barking over time to ensure the animal 401 is complying with local by-laws or to interpret continued barking as a potential stress indicator.

In other embodiments, the analysis of the sensor data may be performed in DMS 301. Again, DMS 301 may perform both episodic data analysis as well as longitudinal data analysis. For the latter, DMS 301 may look at individual events, combined events, and derived events (e.g., calorie intake versus activity levels). By looking at such events in the DMS 301, patterns of animal's 301 health and wellness may be determined. For example, the DMS 301 may determine patterns of improvement (or lack thereof) of an animal following a drug or therapy treatment of animal 401 after it has left the veterinarian. Further, the wearable device 101 data may be combined with sensors from other sources (e.g., RSS feeds 302, owner observations 312, etc.) in performing the analysis. For example, an RSS feed 302 including the number of degree days may be compared to a number of high temperature alerts at a wearable device 101 to determine if, e.g., animal 401 is overheated or if, rather, it is just an abnormally warm month. As another example, owner's observations 312 (e.g., observations of staggering after exertion, unusual fatigue, abnormal coughing, pale gums, etc.) may lead the DMS 301 to modify the profile or operation mode of the wearable device to employ profiles with finer granularity and sensing more often and with more sensitive thresholds for cardiopulmonary algorithms at the wearable device 101 level.

Figure 10:
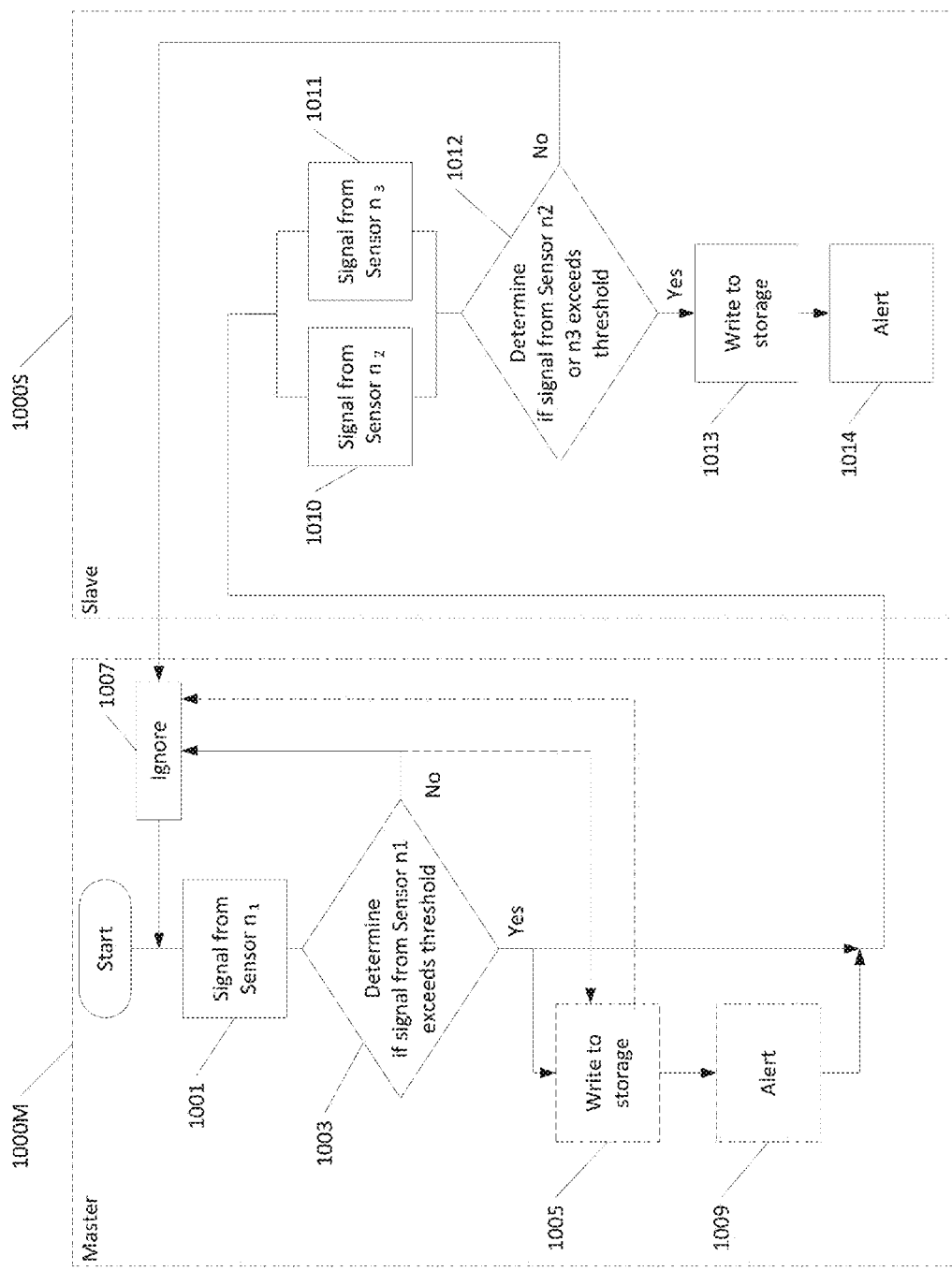
FIG. 10 is a flowchart depicting a sensor triggering other sensors according to some aspects of the disclosure.

As presented in FIGS. 8 and 9, an analysis of an animal's health and wellness may be performed by analyzing data from an individual sensor (e.g., FIG. 8) or from the combination of two or more sensors reading at the same time (e.g., FIG. 9). In other embodiments, analysis of an animal's health and wellness may be performed by one or more sensors triggering one or more additional sensors in order to corroborate the data of the first sensor. This may be more readily understood with reference to FIG. 10. As shown in FIG. 10, data is received from one sensor (in the depicted embodiment, n1) at step 1001. This data is compared to one or more thresholds at step 1003 as described with respect to FIGS. 8 and 9. If the sensor reading does not exceed a threshold (e.g., is not interesting) then the data is ignored at step 1007 and the method returns to step 1001 to obtain additional data. Alternatively, the data may always be stored/written locally at step 1005 for later upload to DMS 301.

If the data from sensor n1 obtained at step 1001 does exceed one or more thresholds at step 1003, then signals from additional sensors may be checked to confirm or corroborate the received data from step 1001. That is, in some embodiments, one or more sensors (in the depicted embodiment, n1) may act as a "master" sensor after it has sensed a threshold level, and then subsequently control additional "slave" sensors. Here, steps 1001-1009 are related to the operation of the master sensor n1, collectively identified by the dashed box 1000M. Similarly, steps 1010-1014 are related to the operation of the slave sensors n2 and n3, collectively identified by the dashed box 1000S. In the depicted embodiment, once data collected at step 1001 exceeds a threshold at step 1005, additional slave sensors are triggered to collect data at step 1010 (n2) and step 1011 (n3) or their previously collected data checked. At step 1012, analysis of the received data (e.g., data received at steps 1001, 1010, and/or 1011) may be performed, and an inference may be made regarding animal's health and wellness. Further, the data received from each sensor (n1, n2, and n3) may optionally be weighted or otherwise adjusted to determine an inference regarding an animal's health and/or wellness as described herein. If, at step 1012, the combined data does not exceed a threshold level (e.g., the further data collected at steps 1010 and/or 1011 does not confirm and/or rather negates an inference made at step 1003), then the data may be ignored at step 1007 and the method thus returns to step 1001 to collect new data and thus continually monitor animal 401. However, if the data collected at steps 1010 and/or 1011 confirms or supplements the inference made from the data collected at step 1001, then this determination is recorded in step 1013 by writing this determination into storage 105. Further, an alert may be returned to the animal's owner and/or a veterinarian at step 1014. Again, regardless of the inference made (e.g., ignore versus alert) the data may be written/stored locally at step 1013 for future upload to the DMS 301.

The methods described in FIGS. 8-10 (e.g., inferences made from a single sensor or a combination of sensors) may be used arrive at specific inferences of an animal's health or wellness. For example, the analysis of one or more sensors Nm may allow episodic and/or longitudinal inferences to be made regarding animal's health and wellness. As an example episodic inference that may be made using one or more sensors, in one embodiment a GPS geo-zone alert may be confirmed or canceled using, e.g., GPS sensor (as one example of the sensor provided on wearable device 101). Specifically, a geo-zone alert may be prone to false positives due to, e.g., temporary loss of communication with one or more satellites (which may thus be interpreted as movement of animal 401). However, in some embodiments, a GPS geo-zone alert may be compared with an accelerometer reading to corroborate/confirm the alert. Specifically, if the animal 401 is not moving (as determined from data received from the accelerometer) the geo-zone alert may be canceled.

Similarly, in some embodiments signal strength of, e.g., an RF signal may be compared to GPS position of animal 401 to confirm, e.g., a breach of a geo-zone. Specifically, a reading from the GPS may be indicative that the animal 401 has moved outside a geo-zone. However, if signal strength of an RF signal from a base station (received at RF antenna) is still rather strong, the GPS readings may be interpreted as a false positive (e.g., the result of losing communication with one or more satellites) and thus the alert may be canceled.

As another example episodic inference that may be made using one or more sensors, a reading of high acceleration (from, e.g., an accelerometer) may trigger additional sensors and/or otherwise be compared with data from additional sensors to determine if animal 401 was involved in an impact event (e.g., being hit by a vehicle). For example, a reading of high acceleration from the accelerometer may be supplemented with a reading from, e.g., a light meter and or a microphone on wearable device 101 (as two examples of internal sensors). If, in addition to the high acceleration reading, the wearable device received a high light incidence reading (e.g., headlights) and/or a high noise reading (e.g., impact) then an alert of a possible impact event may be returned.

As another example episodic inference that may be made using one or more sensors, a breach of a perimeter fence (as determined by RF antenna 109, Wi-Fi, Bluetooth, or other RF technology) may be compared to readings from an ambient light, sound, temperature, and/or humidity sensor on wearable device 101 (as examples of internal sensors) to determine if animal 401 has in fact, e.g., left a house. If the sensed humidity, temperature, light, etc., is indicative of the animal 401 being outside, then the perimeter fence alert may be returned. However, if each reading is indicative of the animal 401 being inside, the breach of perimeter fence alert may be interpreted as a false positive and thus canceled.

As another example episodic inference that may be made using one or more sensors, data from, e.g., a microphone (as one example of a sensor) may be compared with reading from an accelerometer (as another example of a sensor) to determine if animal 401 has been, e.g., barking longer than a threshold period of time. For example, a reading from a microphone may be indicative of animal 401 barking, or may be due to some other event (e.g., thunder). However, data received from the accelerometer may confirm/negate that the animal has been barking according to whether or not a signature head movement or vibration of a barking event was sensed or not.

Further, sensed data from an inward looking antenna (e.g., a UWB antenna) may be compared with a microphone to form many inferences related to respiration quality and the like. For example, UWB antenna may be used to form an inference of animal's respiration quality by monitoring movement of muscles in the neck area (e.g., the muscles surrounding the animal's trachea 511). Further, the sensed UWB data may be corroborated with a microphone located on wearable device 101 and/or an external microphone (e.g., a microphone located on an owner's personal mobile device such as a smartphone, etc.) to make an inference regarding whether the animal 401 has kennel cough, bronchitis, etc.

As another example episodic inference that may be made using one or more sensors, noninvasive cardio output may be determined by measuring both heart rate (beats per minute), quality (fluctuations over the minute), and stroke volume to provide cardiac output using UWB technology on either an episodic or trending basis. Other derived conclusions from these measurements may also include a change in blood pressure over time and whether the animal is losing blood volume due external or internal bleeding. These sensors may be placed on the animal's chest near the sternum, at the front of the neck near the wind pipe and carotid arteries, or on other parts of the animal to pick up specific signals of interest.

As another example episodic inference that may be made using one or more sensors, noninvasive core temperature may be measured and/or derived from several internal and ambient thermistors. Further, microwave radiometry/thermometry (using a microwave antenna) along with other techniques may be used to determine fluctuations in core temperature which may be indications of hypothermia, hyperthermia, bacterial or viral infections, inflammation, on set of disease, immune-mediated or neoplastic diseases, extreme exercise, or ovulation.

As another example of an episodic inference that may be made using one or more sensors, noninvasive measurement of blockages in the digestive track can be accomplished by moving the wearable device 101 to the area of concern to allow readings and an upload of data from this activity using the UWB technology.

As another example episodic inference that may be made using one or more sensors, noninvasive measurement of the animal's drinking and eating habits may be measured independently or corroborated with other sensors using UWB technology by examining signals from the neck area including the esophagus and surrounding tissues.

In some embodiments, a base line measurement of animal 401 may be determined and then compared to subsequent data collection to determine, e.g., one or more of the inferences discussed herein. In some embodiments, data received from two or more sensors may be used to determine, e.g., that it is an appropriate time to collect this baseline data. For example, in some embodiments, a clock or other component (e.g., light meter, etc.) may be accessed to determine, e.g., that it is night time. Further, data from the accelerometer may be referenced to confirm that, e.g., animal 401 is sleeping (as indicated by no or little acceleration). In such embodiments, a baseline measurement of one or more vital signs and/or physiological signs may be taken in response to the one or more sensors indicating that animal 401 is sleeping.

The above methods of determining episodic inferences from one or more sensors may be more readily understood with reference to a specific example. In one embodiment, wearable device 101 may include an accelerometer, a microphone (as examples of internal sensors) and/or cardiopulmonary sensors (e.g., UWB device). In such an embodiment, the accelerometer may measure a high acceleration event, and the wearable device 101/DMS 301 may interpret the acceleration as indicative of a possible impact event (e.g., the animal 401 was hit by a vehicle). The wearable device 101/DMS 301 may then corroborate or confirm this interpretation by referencing other sensors, e.g., microphone. For example, if the microphone sensed a loud noise at the moment of the high acceleration, the inference of an impact event may be confirmed. This may then trigger other sensors, such as cardiopulmonary sensors (e.g., UWB device). For example, the cardiopulmonary sensors may check animal 401 for anomalies, which may include, e.g., checking animal 401 for loss of blood volume (indicative of, e.g., internal or external bleeding).

Figure 11:
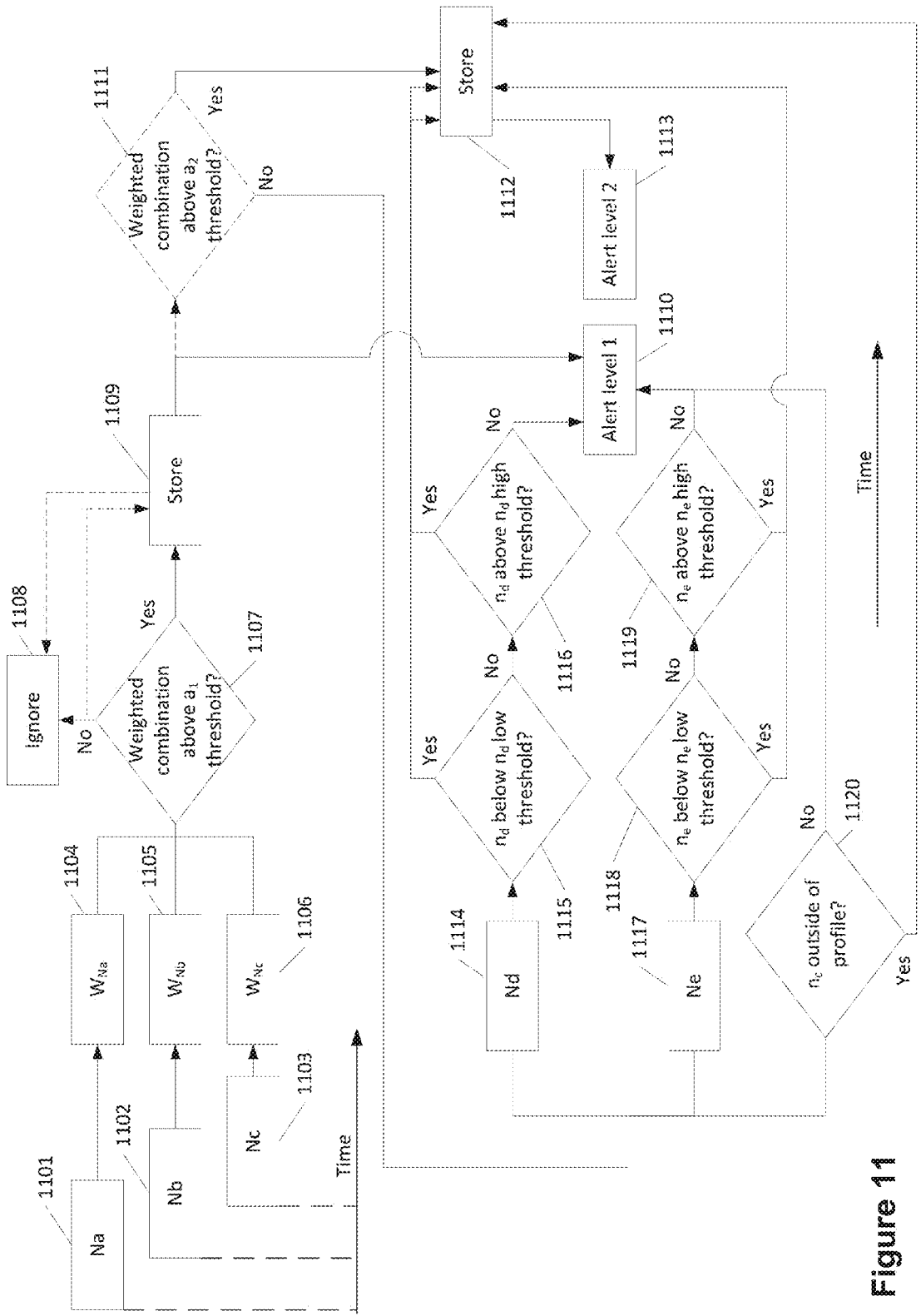
FIG. 11 is a flowchart depicting an illustrative example of how an inference may be formed using readings from different sensors according to some aspects of the disclosure.

The example of an episodic inference of an impact event made by the wearable device 101 and/or DMS 301 is illustrated in FIG. 11. FIG. 11 illustrates how readings of one or more sensors may be interpreted as indicating that an event has occurred. As it shown in FIG. 11, signals from five sensors are used with the sensors identified as Na, Nb, Nc, Nd, and Ne, respectively. The readings from sensors Na 1101, Nb 1102, and Nc 1103 are weighted independently by weighting factors $W_{Na}$ 1104, $W_{Nb}$ 1105, and $W_{Nc}$ 1106, respectively. Next, in step 1107, it is determined if the weighted combination of the readings of these three sensors is above a threshold a1. If no, then the system ignores the sensor readings in step 1108 and returns to monitoring the animal. If yes, then this determination is stored in step 1109 and the alert provided as alert level 1 in step 1110.

FIG. 11 also includes the ability for determination of a second alert level (alert level 2). For instance, the system knows after step 1107 that alert level 1 has been reached. The system may additionally check in step 1111 the weighted combination or perform an additional weighting and compare the weighted combination against a second alert level threshold, here, the a2 threshold. If yes from step 1111, that is second alert level a2 is stored in step 1112 and alert level 2 is identified to the owner/DMS in step 1113.

If no from step 1111 as having not found a second alert level based on the initial weighted sensor readings from sensors Na, Nb, and Nc, there may be additional sensor inputs that allow a determination that the second alert level has been reached. For instance, sensor readings from sensors Nd 1114 and Ne 1115 may be obtained. For the sensor reading from sensor Nd, the system determines in step 1115 if the sensor reading is below a low threshold for sensor Nd. If yes, then this determination is stored in step 1112 and the alert level 2 is provided in step 1113. If no from step 1115, the system determines in step 1116 if the sensor reading is above a high threshold for sensor Nd. If yes, then this determination is stored in step 1112 and the alert level 2 is provided in step 1113. If no from step 1116, then the system continues to provide the alert level 1 in step 1110.

A similar determination may be made for reading from sensor Ne. For the sensor reading from sensor Ne, the system determines in step 1118 if the sensor reading is below a low threshold for sensor Ne. If yes, then this determination is stored in step 1112 and the alert level 2 is provided in step 1113. If no from step 1118, the system determines in step 1119 if the sensor reading is above a high threshold for sensor Ne. If yes, then this determination is stored in step 1112 and the alert level 2 is provided in step 1113. If no from step 1119, then the system continues to provide the alert level 1 in step 1110.

Finally, one of the original sensor levels may be reviewed to determine if it is outside of a profile for that sensor. For instance, in step 1120, the sensor readings of sensor Nc are compared against a profile for that sensor. If the readings are outside of that profile, then this determination is stored in step 1112 and the alert level 2 is provided in step 1113. If no from step 1120, then the system continues to provide the alert level 1 in step 1110.

The following explains how FIG. 11 may be applied to specific sensor readings to determine if an event has occurred. The following example explains how a determination is made that a high impact event has occurred. Here, sensors Na, Nb, Nc, Nd, and Ne are represented by a light meter sensor n1, a microphone/peak sound sensor n2, an accelerometer n3, a GPS receiver n4, and a cardiopulmonary sensor n5, respectively.

At step 1103, accelerometer (n3) senses a high acceleration event (e.g., 10+G's) potentially indicative of a high-impact event. In this embodiment, the accelerometer (n3) acts as a "master" sensor such that when it has sensed this episodic condition at step 1103 (e.g., high accelerations possibly indicative of an impact event), it may control the sensing and/or data reporting of other sensors to confirm/corroborate the event. Specifically, processor 101 may use the high signal on accelerometer n3 to look back for recent readings from light meter n1 and microphone n2. Those recent readings may have been stored in storage 105 or in storage 119, depending on the sensor. The effect is that accelerometer sensor n3 is, for this instance, a master sensor and the light meter n1 and microphone n2 are the slave sensors.

The previous readings from the slave sensors are reviewed to look for episodic threshold events to create a more accurate picture as to what has transpired over the previous time interval and possibly confirm a possible high impact event from accelerometer n3. Thus, at step 1105 processor 100 retrieves stored data from the microphone/peak sound sensor (n2) for a time period immediately preceding and overlapping with the high acceleration reading, and at step 1107 processor 100 retrieves stored data from the light meter n1 for a time period immediately preceding and overlapping with the high acceleration reading.

At steps 1104-1106, the data received from each sensor may be weighted and combined into a single result to determine in step 1107 if the constructed profile meets a high degree of probability that an event of interest (e.g., impact) has occurred. For example, if the light meter (n1) sensed a high incidence of light (potentially indicative of headlights), and/or if the microphone/peak sound sensor (n2) sensed a loud noise (potentially indicative of a being impacted by a vehicle), then the method may determine at step 1107 that an impact has in fact occurred. If the other readings do not confirm the possible impact event, then the data may be ignored at step 1108. Regardless, the data received may be written and/or stored locally at step 1109 for subsequent upload to the DMS 301.

If the combined and corroborated data meets certain conditions (e.g., each is indicative of an impact event) in step 1107, the master sensor (in the depicted embodiment, accelerometer n3) may trigger and/or change states other sensors (including itself) in order to, e.g., take individual spot readings, schedule-based readings, or change each sensor's sensing configurations. If the readings are inconclusive, the sensors are instructed to continue reading.

For example, in the depicted embodiment, at step 1109, the accelerometer (n3) changes (as being controlled by processor 100) from being in an interrupt mode (e.g., looking for episodic events) to a real-time monitoring of motion activities. This real-time monitoring may be compared to a profile to determine if the animal's gait has changed dramatically as determined in step 1120. At step 1117, the GPS sensor (n4) is instructed (i.e., controlled by processor 100) to determine location, speed, and/or direction of the animal 401. If the animal 401 is moving in a sustained fashion, this reading would have a lower risk ratio assigned to it. Further, at step 1107, the cardiopulmonary sensor (n5) may be triggered to check on heart rate, respiration rate, stroke volume, and/or a change in blood pressure. The cardiopulmonary sensor (n5) may thus look for anomalies (e.g., loss of blood) and assign a risk ratio to the readings. Or, in other words, the processor 100 may look for anomalous readings from the cardiopulmonary sensor n5 and assign a risk ratio to those readings.

At steps 1115, 1116, 1118, and 1119, the processor in the wearable device 101 and/or DMS 301 may compare the data from one or more of the above sensors to determine, e.g., an alert level following the determined episode (e.g., impact event). For example, after considering all of the above weighted data points, the processor may determine that the event recorded merits various levels of alerts (at steps 1110 and 1113) to be sent to the owner and/or the veterinarian based on the reliability of the sensor readings. Further, the wearable device 101 may be instructed to continue reading at steps 1110 and 1113 in order to continually monitor the animal's progress following the impact event.

The following equations describe the weighting of the values of the sensors and the comparison against the alert level thresholds. Equation (1) below describes how a sensor reading from sensor Nc is checked against the threshold for sensor Nc:

$$\text{If } (n_c > n_{c\ threshold}), \text{ then alert for } n_c \text{ exceeding } n_c \text{ threshold} \quad (1)$$

Equation (2) below describes how a sensor reading from sensor Nc is checked against the threshold for sensor Nc and, if the threshold is exceeded, then determining if a weighted combination of sensor readings Na and Nb and Nc exceed the alert level 1 threshold:

$$\text{If } (n_c > n_{c\ threshold}), \quad (2)$$

$$\text{if } \frac{(n_a \text{max over time } T1)}{n_{a\ threshold}} \times w_a + \frac{(n_b \text{max over time } T2)}{n_{b\ threshold}} \times w_b + \frac{(n_c \text{max over time } T3)}{n_{c\ threshold}} \times w_c \geq a_1,$$

then alert for alert 1 where:
$a_1$ is the alert level 1 threshold such that a value above $a_1$ results in alert level 1 while a value below $a_1$ does not result in an alert;
Times T1, T2, and T3 are the time intervals in which the previous readings for sensors Na, Nb, and Nc are reviewed; and
Wa, Wb, and Wc are the weighting values for each of the Na, Nb, and Nc sensor readings.

Notably, equation (2) normalizes the values of each sensor by dividing the max value of the sensor during a time window (or min as appropriate) by the threshold. This permits the individual units of each sensor to cancel out. Next, the weighting factors scale each normalized sensor reading such that they can be added and compared against the threshold for alert level 1 (a1).

Equation (3) below describes a similar analysis as that of equation (2) but sets the alert level threshold at the alert level 2 a2 threshold:

$$\text{If } (n_c > n_{c\ threshold}), \quad (3)$$

$$\text{if } \frac{(n_a\text{max over time } T1)}{n_{a\ threshold}} \times w_a +$$

$$\frac{(n_b\text{max over time } T2)}{n_{b\ threshold}} \times w_b + \frac{(n_c\text{max over time } T3)}{n_{c\ threshold}} \times w_c \geq a_2,$$

then alert for alert 2 where:
  $a_2$ is the alert level 2 threshold such that a value above $a_2$ results in alert level 2 while a value below $a_2$ does not result in an alert;
  Times T1, T2, and T3 are the time intervals in which the previous readings for sensors Na, Nb, and Nc are reviewed; and
  Wa, Wb, and We are the weighting values for each of the Na, Nb, and Nc sensor readings.
Equation (4a) and (4b) relate to equation (2) but also includes the slave sensor analyses of FIG. 11:

$$\text{If } (\text{master})(n_a > n_{a\ threshold}) \text{ and} \quad (4a)$$

$$\frac{(n_a\text{max over time } T1)}{n_{a\ threshold}} \times w_a +$$

$$\frac{(n_b\text{max over time } T2)}{n_{b\ threshold}} \times w_b + \frac{(n_c\text{max over time } T3)}{n_{c\ threshold}} \times w_c \geq a_1$$

then activate slave (4b)

If $(((n_d < n_{d\ low\ threshold}) \text{ or } (n_d > n_{d\ high\ threshold}))$ or $((n_e < n_{e\ low\ threshold}) \text{ or } (n_e > n_{e\ high\ threshold}))$ or $((n_a \neq \text{preexisting profile for } n_a))$, (4b)

then alert level 2, otherwise alert level 1.
where:
  $a_1$ is the alert level 1 threshold such that a value above $a_1$ results in alert level 1 while a value below $a_1$ does not result in an alert;
  Times T1, T2, and T3 are the time intervals in which the previous readings for sensors Na, Nb, and Nc are reviewed;
  Wa, Wb, and We are the weighting values for each of the Na, Nb, and Nc sensor readings; and
  "preexisting profile for $n_a$" is a profile for expected values of $n_a$ over a time interval.

Here, alert level 2 is defined by being activated by both master and slave reaching predefined levels. Alert level 1 is defined by being activated by only the master reaching its predefined level but the slave not reaching its predefined level.

The equations above also permit the sensors to be located on other devices based on the time T being evaluated for each sensor reading. So, once a common time is determined (for instance, the time T(Nc) at which the reading from sensor Nc exceeded the Nc threshold), the other sensor readings are time normalized from that time T(Nc) and evaluated.

Sensors Located on Different Devices

As described above, all of the sensors may be located on wearable device 101 or some located on the wearable device 101 and others located on a separate device. A separate device may be a user's smartphone (e.g. the microphone on the smartphone). In short, data may be captured and compared from sensors located on more than one device (e.g., wearable device 101 and a user's mobile device) and compared to determine, e.g., an episodic inference about the animal's health and wellness. For example, FIG. 12 illustrates one example method for capturing sensor data from more than one device which can then be forwarded to the DMS 301 and analyzed to determine an inference regarding animal's health and wellness (in the depicted example, respiration inferences). As with FIG. 11, the timeline 12011 of FIG. 12 indicates a relative time that each step is performed relative to one another. In FIG. 12, at step 1201 a user opens a mobile device application. For example, the health-monitoring system as described herein may include a companion mobile application that can be downloaded to an animal 401 owner's smartphone, tablet, computer, etc., which may capable of triggering sensors on demand. A user may be the animal's owner or a veterinarian, etc. In step 1202, the user may select a function they wish to collect data about. The specific sensors selected for capturing and returning data may vary depending on what particular inference, etc., the user triggers. In the embodiment depicted in FIG. 12, the user selects respiration analysis. At step 1203, commands may be sent to the sensors to collect and/or forward data related to this respiration analysis. For example, because the user selected "respiration analysis," a command may be sent to a cardiopulmonary sensor (n5) and to an accelerometer (n3), both located on wearable device 101, and to a microphone (n14) located on the user's mobile device. At steps 1204, 1205, and 1206, each respective device may collect data and/or retrieve previously collected data. These sensors could be placed on standby and triggered based on the start of an event (as, for instance, a coughing fit).

In the following three examples, the following scenarios are explained: no triggering between the mobile device and the wearable device (only being synced by the DMS), triggering of the mobile device to start recording by the wearable device, and triggering of the wearable device to start recording by the mobile device. In the first example, an application executing on the user's mobile device may be executing and recording audio files with time stamping. The DMS may correlate the audio file with readings from accelerometers based on time-stamps of data obtained from the accelerometers. In the second example, the mobile device or the wearable device may trigger the other based on sensed levels exceeding a threshold. For instance, the mobile device may be waiting for the wearable device to indicate that the wearable device's accelerometer has started sensing the coughing fit at which point the wearable device alerts the mobile device. In response to the alert, the mobile device may start recording an audio file with time stamps. In this example, the excess, uninteresting audio file recorded before the dog started coughing is not recorded. In the third example, the mobile device informs the wearable device that the microphone on the mobile device has picked up the sounds of the coughing fit and that the wearable device is to monitor the animal. In the following three examples, the following scenarios are explained:

Each piece of collected data at steps 1204-1206 may be time-stamped such that, when analyzed, each may be lined up in order or otherwise synchronized to correctly aggregate and consider each piece of data with the others. At step 1207, the data collected on wearable device 101 is uploaded to the DMS 301, and at step 1208, the data collected at the user's mobile device is uploaded to DMS 301. At step 1209, the uploaded data are correlated against each other based on synchronizing the timestamps to determine when a relevant. Of coughing has begun. Next, in step 1210 the data are analyzed at the DMS 301 to determine appropriate inferences regarding the animal's health and wellness (in the depicted example, respiration quality).

For example, the combined data may lead to an inference that the animal 401 is suffering from kennel cough or bronchitis. Further, because in some embodiments the data will be time-stamped, an inference may be readily determined even though the sensor readings are coming from disparate sources (here, wearable device 101 and a mobile device). Although as described the analysis step 1210 is performed at the DMS 301, in other embodiments the analysis may be performed at the user's mobile device and/or the wearable device 101.

In addition to episodic inferences made using the methods depicted in FIGS. 8-12, longitudinal inferences (e.g., trending inferences) may be made using the above described methods. That is, because collected data may be stored locally in the wearable device (at, e.g., steps 805, 907, 1005/1013, and/or 1109/1112) and/or uploaded to the DMS 301 for storage, changes or fluctuations, etc., in data over time may be monitored, and according longitudinal (trending) inferences may be made regarding animal's health and wellness.

By way of example, in some embodiments animal's long-term weight fluctuations may be monitored and inferences may be made about the animal 401 accordingly. For example, monitoring long-term weight fluctuations are important as a lean pet has a 15% increase in lifespan (+2 years) and may also be a precursor to other developing conditions. On the other end of the scale, rapid weight loss may be indicative of a digestive track blockage or cachexia where the body is breaking down protein and fat due to the onset of diabetes. Thus, by monitoring and comparing an animal's weight overtime, an inference as to the animal's health and wellness may be determined.

As another example of a longitudinal inference that may be determined using one or more sensors, an activity level of an animal may be monitored (using, e.g., an accelerometer, GPS, etc.). Further, the measured activity levels may be adjusted by the DMS 301 for weekends and weekday lifestyle profiles of the animal 401 and/or the animal's owner. For instance, if the owner takes the animal for walks at 3 am, this may be identified by the owner to the DMS and the DMS refrain from alerting the owner that the animal has left the owner's house at night. Inferences made from the monitored activity levels may indicate that the animal is not being provided with enough exercise opportunity or that conditions such arthritis are slowing the animal down during times of self-initiated activity.

As another example of a longitudinal inference that may be determined using one or more sensors, the animal's eating and hydration habits may be monitored over time. Hydration and eating fluctuations may be important indicators of developing polyphagia and polydipsia conditions related to diabetes.

As another example of a longitudinal inference that may be determined using one or more sensors, sleep patterns of an animal may be monitored to form inferences regarding animal's health and wellness. Sleep patterns may be important indicators of underlying issues with pets such as osteoarthritis. Some owners may assume that an animal sleeping more is just a result of old age, whereas, in reality, it may be an indicator of developing medical conditions. For example, an animal may not limp or whine when excited during play and act like a younger dog but will pay for it later. This may manifest itself in longer rests, stiffness on rising, and resistance to go on their regular walks. Other reasons for longer sleep periods could be caused by thyroid, kidney, or liver disease. Animals may also have sleep disruption caused by obsessive-compulsive behavior disorders. In some embodiments, sleep patterns may be derived by the DMS 301 and collaborated with owner personal observations 312.

According to other aspects of the disclosure, longitudinal inferences may be determined using the provided UWB technology of the wearable device (e.g., using UWB device). For example, in one embodiment respiration monitoring may uncover abnormal signs such as panting while resting, using more abdominal muscles to breath, labored breathing, asymmetrical breathing, increased or decreased breathing rates, wheezing, coughing, and choking.

As another example of a longitudinal inference that may be determined using UWB technology, animal's heart rate may be monitored over time by UWB device. Heart rate monitoring may uncover increased or decreased heart rate and/or abnormal rhythms, which may include the heart speeding up and slowing down or missing beats. In additional embodiments, stroke volume measured overtime may be used to derive the overall fitness level of the animal 401 and/or indicate that the animal 401 is developing conditions that would cause it to be lower.

As another example of a longitudinal inference that may be determined using UWB technology, an animal's blood pressure changes (both increased and decreased blood pressure) may be monitored. Blood pressure changes from a base line (which may be measured, e.g., when animal 401 is sleeping or otherwise in a state of low activity as discussed) may be an indicator of hypertension developing which may lead to other severe medical conditions.

Also, using a pair of thermometers, changes in an animal's core temperature (both increased and decreased) may be monitored. Core temperature changes from a base line core temperature, which may be determined at the outset of monitoring (and adjusted as needed as discussed later), may be an indicator of the overall health of animal 401. Deviations from an expected core temperature range may be indicators of developing health problems or changes in overall animal status, such as pregnancy or being present in an inhospitable environment (e.g., hyperthermia or hypothermia).

In any of the above embodiments, collected data may be time-stamped in order determine time-dependent inferences. That is, time stamping the various sensing activities and the ability to look backward in time allows for a root-cause analysis to determine an adverse event (e.g. the animal was walking fine, but then played fetch and is now limping). Further, in some embodiments, time-stamping may also allow for the analysis of the rate of change which in turn can be used to predict a possible outcome (e.g. the animal is running at an increasing rate of speed towards the outer area of the geo-zone and thus is likely to breach that zone).

FIG. 13 presents a table 1301 summarizing illustrative attributes of some sensors that may be located on wearable device 101 or located external to wearable device 101 and used in conjunction with the health-monitoring system described herein according to some aspects of the disclosure.

Specifically, 1301 contains column 1303 denoting a number of each sensor (denoted as Nm), column 1305 indicating the type of each sensor, column 1306 describing the location of the sensor relative to the wearable device, column 1307 indicating a primary purpose of each sensor, column 1308 describing a general category of sensor, column 1309 indicating whether each sensor may act as a master or a slave sensor (as described herein with respect to FIG. 14), column 1311 indicating a secondary purpose (if any) of each sensor.

By way of example, in this embodiment N1 refers to a light meter and/or spectrometer located on wearable device 101. As denoted in column 1307, the light meter's primary purpose may be to monitor light levels surrounding wearable device 101 (and thus animal 401). Further, as indicated in column 1309, the light meter may only act as a slave sensor and thus, in this embodiment, may not control other sensors. As indicated in column 1311, the light meter may also have a secondary purpose, here serving as an indoor/outdoor indicator (by, e.g., sensing UV levels) or analyzing nearby chemical signatures in the air.

Figure 14:
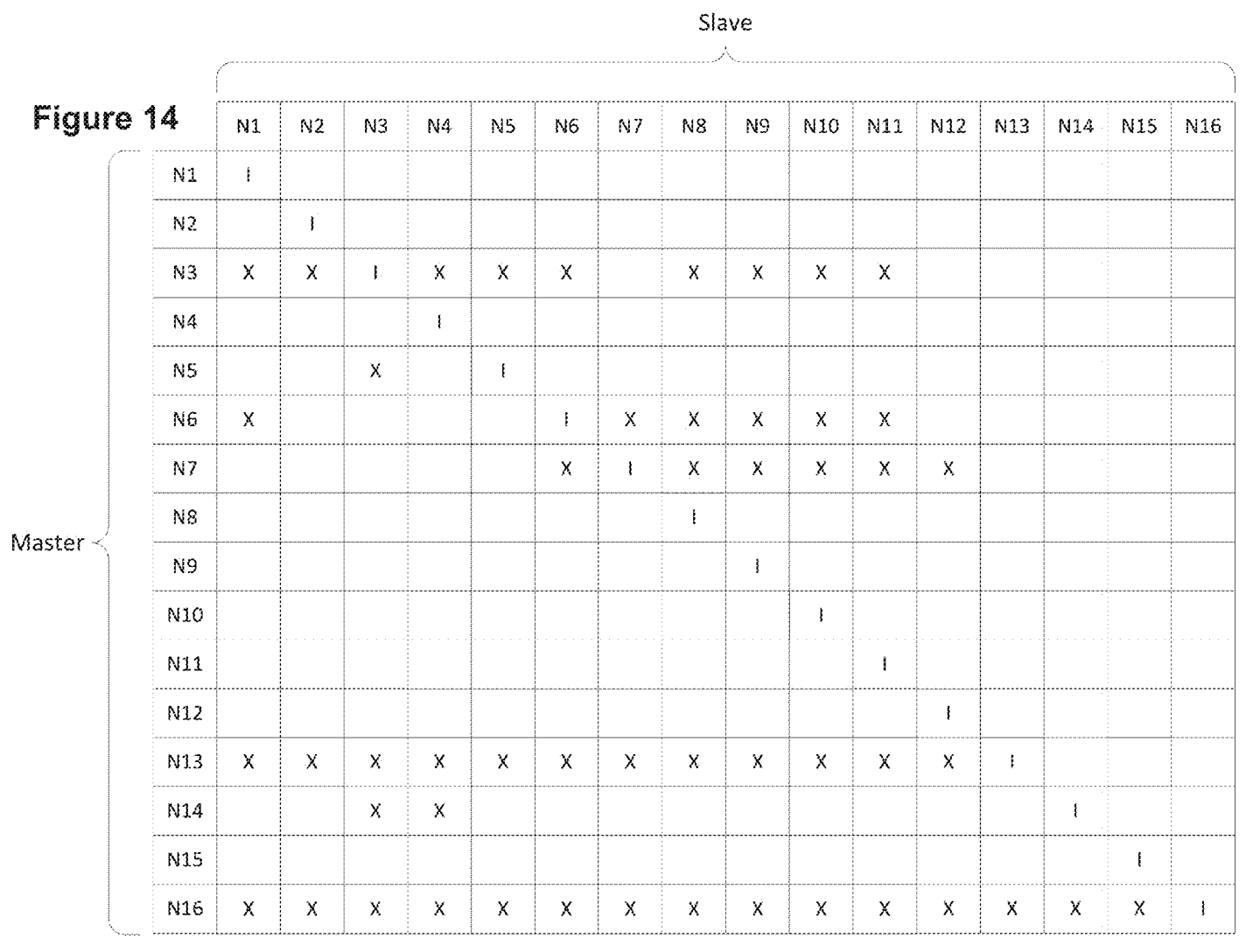

FIG. 14 presents a table indicating illustrative master/slave relationships of each sensor presented in FIG. 13 according to or more embodiments of the disclosure. Specifically, FIG. 14 includes rows identifying each sensor as well as columns identifying each sensor. The values in each cell identify the relationship as a row sensor is a master sensor in contrast to the slave identified in the column sensor where the intersecting cell includes an "X". At the intersection of the same sensor in the row and column title, the cell value is identified by "I" to indicate if the identical sensor. Interestingly, in some implementations, each sensor may act as a master to itself (e.g., control further collection of data by itself in response to a sensed reading). An example of this is shown in step 1120 of FIG. 11 identifying whether the readings from sensor Nc are outside of an expected profile.

By way of example, as indicated by each "X" or darkened cell in the row following "N3" listed, in some embodiments accelerometer (N3) may act as a master to slave sensors N1 (light meter), N2 (peak sound), N3 (itself, accelerometer), N4 (GPS), N5 (cardiopulmonary), N6 (temperature), N8 (Wi-Fi), N9 (Bluetooth), N10 (RF), and N11 (GSM). Further, as indicated by each "X" or darkened cell in the column below "N3", in some embodiments accelerometer (N3) may serve as a slave to other master sensors, namely N3 (itself, accelerometer), N5 (cardiopulmonary), N13 (battery strength), and N14 (mobile microphone).

Figure 15:
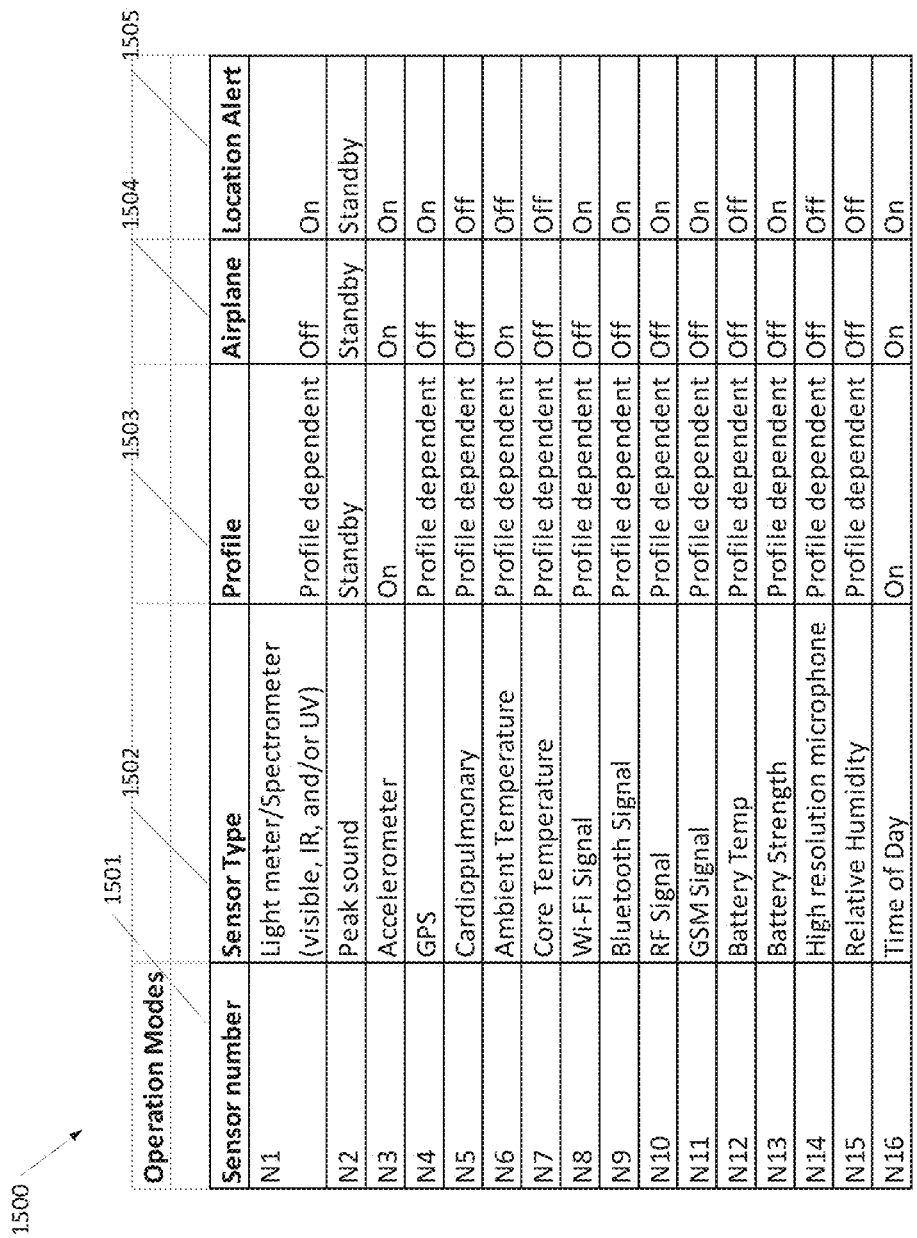
FIG. 15 shows an illustrative example of how the activation of the sensors of FIG. 13 may be modified in different operation modes in accordance with one or more aspects of the disclosure.

FIG. 15 relates to various operation modes and how each sensor may operate in the various operation modes. Column 1501 identifies the sensor by number. Column 1502 identifies a sensor type. Column 1503 identifies how each sensor operates in a profile operation mode. Column 1504 identifies how each sensor operates in an airplane (no RF radios operative) operation mode. Column 1505 identifies how each sensor operates in a location alert operation mode.

For instance, FIG. 15 identifies the peak sound sensor, the accelerometer, and the time of day sensor (e.g., an internal clock) are not affected by the specific profile settings when in the profile mode as shown in column 1503. The remaining sensors may have different operations based on the profile.

In the airplane operation mode 1504, most of the sensors are off while peak sound is in a standby state the accelerometer, the ambient temperature sensor, and the time of day sensor are on. In other words, the operation of the sensors in the airplane mode identifies that all radios, sensors, and/or components that generate significant that generate significant electro-magnetic radiation are disabled.

In the location alert operation mode 1505, all sensors that may help determine the location of an animal are on, including light meter, accelerometer, GPS, WiFi signal detector, Bluetooth signal detector, RF signal detector, and GSM signal detector sensors. The remaining sensors may be turned off to help conserve power. The battery strength sensor may also be left on in the location alert mode 1505 to identify to the collar when it is running low on power. For example, the cardiopulmonary sensor n5 is disabled in favor of the GPS sensor/radio n4, the Wi-Fi sensor/radio n8, the Bluetooth sensor/radio n9, the RF sensor/radio, n10, and the GSM sensor/radio n11, depending on which of these sensors/radios are present.

FIGS. 16A-16G relate to different profiles usable by wearable device 101. In each of FIGS. 16A-16G, column 1601 identifies the sensor number and columns 1602 identifies the sensor type.

FIG. 16A describes a first profile, Profile 0, which relates to a normal monitoring profile set by the owner. The profile type identified in cell 1603A and its title identified in cell 1604A. Here, the range between the low threshold 1605A and the high threshold 1606A is set relatively large, the frequency of operation of each sensor is relatively infrequently, and granularity for the readings of various sensors is low. This profile is an example of a normal profile set by the owner. For instance, a processor operating under Profile 0 of FIG. 16A has a low granularity for accelerometer sensor n3. The low granularity may take the form of a low pass filter applied to a signal from the accelerometer sensor n3. The low pass filter may smooth any instantaneous accelerometer output level to eliminate and/or reduce the triggering of the accelerometer high threshold when the instantaneous output is above the high threshold but while the average output is low. Alternatively, the low pass filter may be replaced with a smoothing filter (e.g., a convolution filter with a longer time constant) to reduce any errant spikes in the signal from the accelerometer n3. Further, the above described filters may be part of the processor such that the processor ignores or is less sensitive to acceleration spikes with short duration FIG. 16B describes a second profile, Profile 1, which relates to an enhanced monitoring profile set by the owner. The profile type identified in cell 1603B and its title identified in cell 1604B. Here, the range between the low threshold 1605B and the high threshold 1606B is narrow compared to that of Profile 0 of FIG. 16A, the frequency of operation of each sensor is relatively more frequent, and granularity for the readings of various sensors is high. This profile is an example of an enhanced profile where the owner is concerned about the pet's current health and desires more information to be obtained by the collar. In contrast to the Profile 0 of FIG. 16A, this Profile 1 has enhanced sensitivity as shown in some of the trigger point for the low thresholds of column 1605B being higher and the trigger point for the high thresholds of column 1606B being lower. Also in some instances, the frequency of monitoring in column 1601B is more often. Similarly, the granularity as shown in column 1608B is also high. For instance, for accelerometer n3, the granularity is described in column 1608B as being high. With respect to the example of the low pass filter, the filter may be removed or modified to reduce the level of filtering of higher frequency signals. With respect to the example of the smoothing filter, the time constant (or window of time over which the smoothing takes place) is reduced to permit higher frequency acceleration signals to be analyzed by a processor. Also, as described with respect to FIG. 16A, the filters may be part of the processor such that the processor adjusts internally how sensitive it is to the outputs of various sensors based on a current profile.

FIG. 16C describes a third profile, Profile 2, which relates to a normal monitoring profile set by the veterinarian. The profile type identified in cell 1603C and its title identified in cell 1604C. Here, the range between the low threshold 1605C and the high threshold 1606C is set relatively large with even some sensors not being used as the veterinarian may not need the readings from the sensors, the frequency of operation of each sensor is relatively infrequently, and granularity for the readings of various sensors is low. This is an example of a profile where the vet may be monitoring the pet's current health to establish a baseline or as a function of general monitoring (for example, in preparation for a checkup).

FIG. 16D describes a fourth profile, Profile 3, which relates to an enhanced monitoring profile set by the veterinarian. The profile type identified in cell 1603D and its title identified in cell 1604D. Here, the range between the low threshold 1605D and the high threshold 1606D is set relatively narrow, the frequency of operation of each sensor is relatively frequent, and granularity for the readings of various sensors is high. Again here, some sensors are disabled as the veterinarian may have no need for the readings from those sensors. For instance, this profile may be used before surgery or a procedure (e.g., teeth cleaning with the animal being anesthetized) is performed on the animal to ensure no recent dramatic events have occurred to the animal prior to the surgery/procedure.

For instance, this profile may be used after surgery or after a procedure to monitor for possibility of complications arising from the surgery. Based on the level of need for monitoring the animal, the rate at which information is provided to the veterinarian may be further modified in accordance with the examples of FIG. 22 as relating to the following:

A. Identification of events by the wearable device and uploading those events to the veterinarian, B. Logging of raw data from the sensors and batch uploads of the logged data to the veterinarian, or C. Continuous uploads of raw data to the veterinarian.

Figure 22:
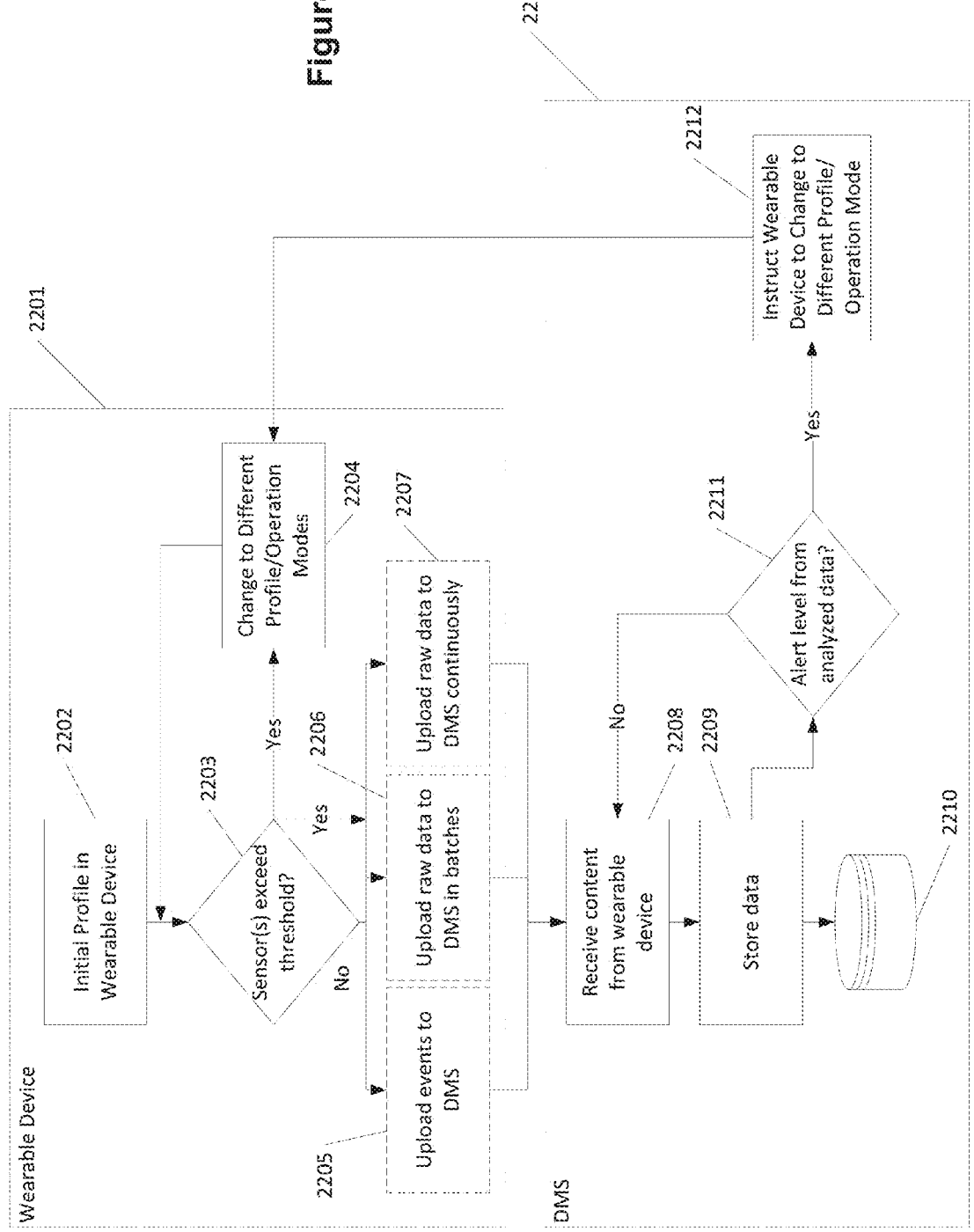
FIG. 22 shows an illustrative example of how profiles may be selected in the wearable device as well as in the DMS in accordance with one or more aspects of the disclosure.

With respect to the above description and the description of FIG. 22, the uploads of the identified events and/or raw data to the veterinarian may be a direct transfer from the wearable device to a remote device (for instance, to a computer on a same local Wi-Fi network as the wearable device) or may be an indirect transfer from the wearable device to the DMS which then forwards to the veterinarian (or makes available for the veterinarian to access) the identified events and/or raw data from the wearable device. Further, the DMS may further derived events from the raw data and possibly the device-derived events from the wearable device. These DMS-derived events may be further provided to the veterinarian or made available for viewing by the veterinarian as desired.

FIG. 16E describes a fifth profile, Profile 4, which relates to a monitoring profile for a first specific symptom type as set by the veterinarian. The profile type identified in cell 1603E and its title identified in cell 1604E. Here, the range between the low threshold 1605E and the high threshold 1606E is set relatively narrow, the frequency of operation of each sensor is relatively frequent, and granularity for the readings of various sensors is high for some sensors but low for others. In this profile, the veterinarian is concentrating on values from some sensors over other sensors. For instance, the veterinarian may be monitoring for gait-related issues based on the accelerometer frequency sampling being "always on" and the granularity being "high".

FIG. 16F describes a sixth profile, Profile 5, which relates to a monitoring profile for a second specific symptom type as set by the veterinarian. The profile type identified in cell 1603F and its title identified in cell 1604F. Here, the range between the low threshold 1605F and the high threshold 1606F is set relatively narrow, the frequency of operation of each sensor is relatively frequent, and granularity for the readings of various sensors is high for some sensors but low for others. In this profile in contrast to that of Profile 4, the veterinarian is concentrating on values from a difference of sensors then important sensors of Profile 4 of FIG. 16E. Here, the veterinarian may be monitoring for a cardiopulmonary-type symptoms or similar set of symptoms by the cardiopulmonary sensor n5 frequency being set to obtain a reading every minute with its granularity set to high.

FIG. 16G describes a seventh profile, Profile 6, which relates to an enhanced monitoring profile set by the veterinarian in which some sensors are operated continuously as opposed to their standard intermittent usage. The profile type identified in cell 1603G and its title identified in cell 1604G. Here, the range between the low threshold 1605A and the high threshold 1606A is set relatively arrow, the frequency of operation of each sensor depends on its importance. For those sensors that are not important, they are not operated and in contrast other sensors are operated continuously. For instance, this profile may be used when an animal is recovering from surgery and the veterinarian desires continuous readings of the vital signs/physiological signs of the animal without stressing the animal by having individual sensors for each vital sign/physiological sign being separately attached. Alternatively, this profile may be used when the animal is in critical condition and is in a constantly monitored state. In this profile, some items are not monitored as they are not relevant when staying in hospital. For instance, monitoring the ambient temperature via sensor n6 or monitoring for GPS signals with sensor n4 are not needed. This profile of FIG. 16G enables veterinarians to use the wearable device 101 in place of separately attached individual sensors that would normally be attached individually to the animal.

Figure 18:
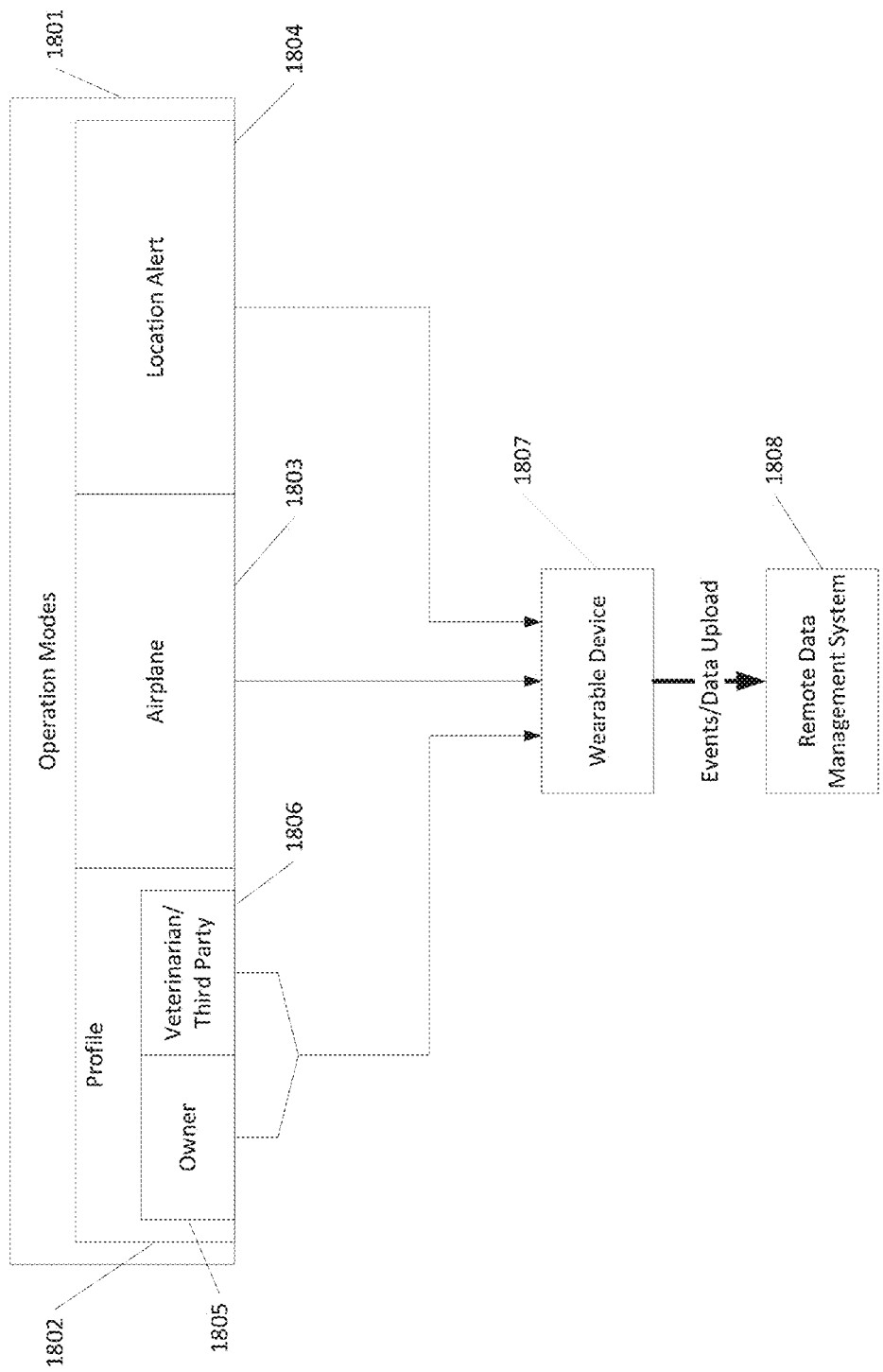
FIG. 18 shows an embodiment with different operation modes of the wearable device in accordance with one or more aspects of the disclosure.

FIG. 18 shows an example of how various sensor profiles may be modified based on breed information of the animal to which the monitoring devices attached in accordance with one or more aspects of the disclosure. Specifically, column 1801 identifies those sensors which may be modified or adjusted in sensitivity when processing based on the type of breed of animal. For instance, high and low thresholds for cardiopulmonary sensor n5 may be adjusted upwards for a breed that has a high average heart rate and downwards for a breed that has a low average heart rate.

FIG. 18 shows an embodiment with different operation modes of the wearable device in accordance with one or more aspects of the disclosure. In this embodiment, the wearable device operates in one of three operation modes: a profile mode 1802, an airplane mode 1803, and a location alert mode 1804. The collection of operation modes is shown as group 1801 and the collection of profiles are shown as group 1802. In this embodiment, two profiles may be implemented in the wearable device: owner profile 1805 and veterinarian/third-party profile 1806. Based on the selection of the operation mode, wearable device 1807 operates as designated by the particulars of the operation mode. Finally, based on the designation in the operation mode of what and when to upload content to the remote data management system, the wearable device 1807 uploads content in accordance with the operation mode.

For instance, in the profile operation mode 1802, this operation mode (and optionally the specific profile) identifies that content from the wearable device 1807 is to be uploaded to the remote data management system 1808 in batches. Next, in the airplane operation mode 1803, as all radio transmission functions are disabled while in the airplane operation mode 1803, the content collected while in operation mode 1803 is stored in wearable device 1807 and subsequently uploaded to remote data management system 1808 only when switched out of airplane mode 1803. Further, when operating in the location alert operation mode 1804, content information is uploaded to the remote data management system 1808. For instance, in one example where the owner is attempting to locate the animal as soon as possible, the location content may be uploaded on a continuous basis to the remote data management system 1808. The data uploaded from the wearable device may include location information from a GPS receiver sensor and/or triangulation information from received cell tower signal strengths and/or IP addresses of Wi-Fi access points, merely storing a list of time stamped IP addresses, or the like. The uploading of data may be real-time or may be batched. With respect to monitoring Wi-Fi access points, the wearable device 101 may keep track of the various access points encountered over time and upload a list of those access points so as to provide a list of locations (or approximate locations) visited throughout the day (or other interval) (thereby providing breadcrumb information of where the wearable device has been throughout the day).

FIGS. 19A-19B show the order in which operation modes take precedence over profiles based on the embodiment of FIG. 18 in accordance with one or more aspects of the disclosure. As used in FIGS. 19A-19B, the "switches" can be hardware switches, software switches or a combination of both. A hardware switch may be a switch located locally on the wearable device that permits selection of one of the operation modes described in FIG. 18. A software switch is a remotely operated command to the wearable device to shift into one of the operation modes of FIG. 18 and/or profiles. The software switch maybe operated by the owner, a veterinarian, and or a third party. For instance, airport personnel may be included in the group including the third-party where the airport personnel may be able to access the wearable device to set it into the airplane operation mode 1803. The combination of hardware and software switches permits a device to respond to either a hardware switch operation (actual switch or a double tap of the device sensed by the internal accelerometer) or a software switch operation. For instance, external hardware switches may be located at one or more locations on the wearable device 101 at, for instance, locations A-C on the wearable device 101 of FIG. 5 or as part of collar/harness 402. Here, the hardware switches may be respective parts of clasp 505 at locations H and I and operated by locking together the parts of clasp 505.

FIG. 19A shows a deprecated order in which an airplane mode switch 1901 has the highest level of precedence. Next, a location alert switch 1902 has the second-highest level precedence. Third, the lowest level of precedence is profiles in profile group 1903 including owner profile 1904 and veterinarian/third-party profile 1905.

FIG. 19B shows the different operation modes based on operation of the switches of FIG. 19A. First, if the airplane mode switch is on, then the wearable device operates in the airplane mode 1907. If the airplane mode switch is off 1906, then the wearable device looks to the state of the location alert switch. If the location alert switch is on, then the wearable device operates in the location alert operation mode 1909. If the location alert switch is off 1908, then the wearable device operates in one of the profile modes 1910 (for instance, in the owner profile 1911 or the veterinarian/third-party profile 1912).

Figure 20:
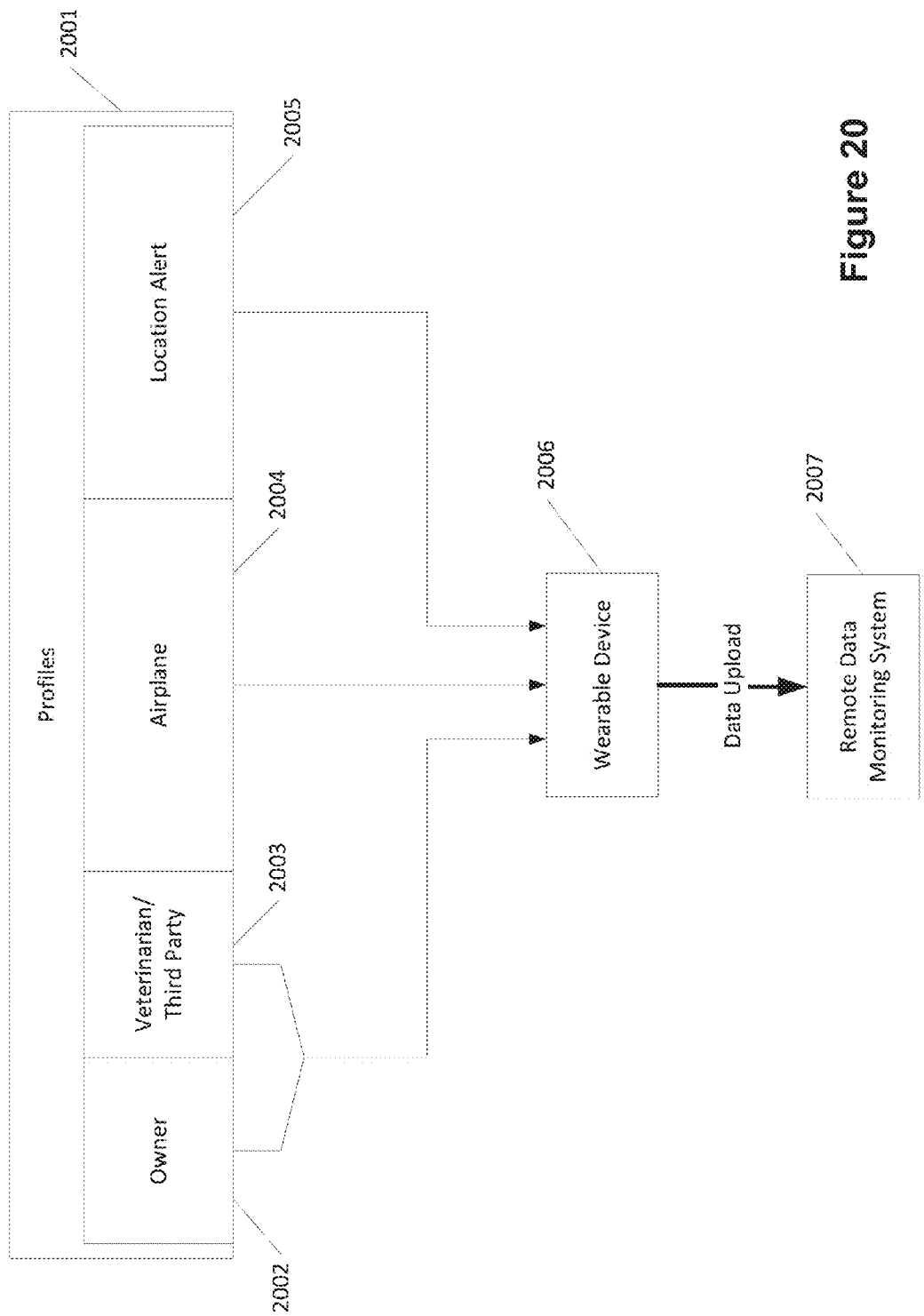
FIG. 20 shows an alternative embodiment with different profiles including profiles replacing the operation modes of the embodiment of FIG. 18 in accordance with one or more aspects of the disclosure.

FIG. 20 shows an alternative embodiment with different profiles including profiles replacing the operation modes of the embodiment of FIG. 18 in accordance with one or more aspects of the disclosure. Profiles 2001 include airplane profile 2004, location alert profile 2005, owner profile 2002, and veterinarian/third-party profile 2003. The selected profile from profiles 2001 dictate how wearable device 2006 operates and uploads data to the remote data monitoring system 2007 (similar to the operation mode/profiles of FIG. 18).

Figure 21:
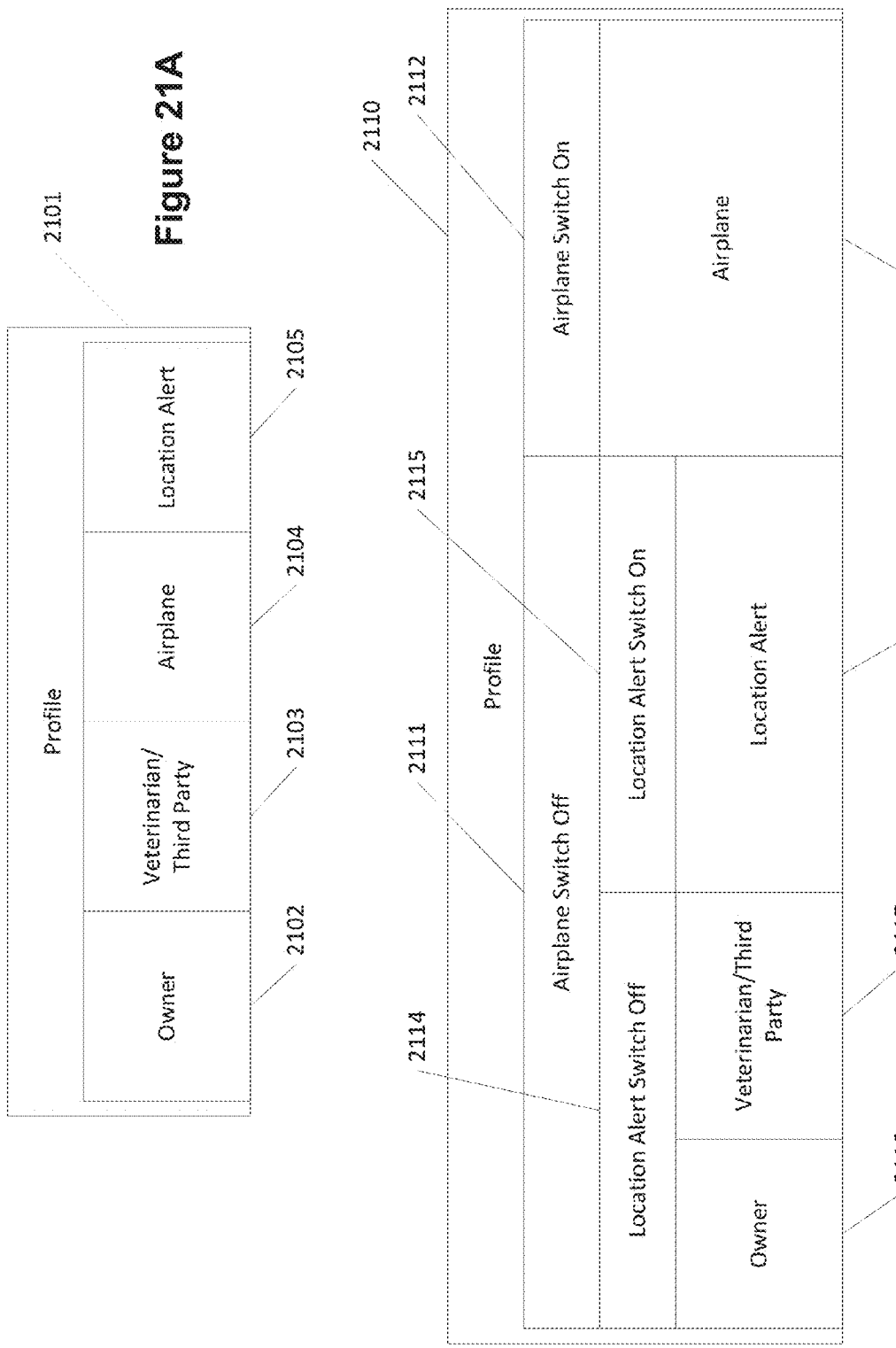
FIGS. 21A-21B show the combination of different profiles of the embodiment of FIG. 20 with options of profile selection by one or more switches in accordance with one or more aspects of the disclosure.

FIGS. 21A-21B show the combination of different profiles of the embodiment of FIG. 20 with options of profile selection by one or more switches in accordance with one or more aspects of the disclosure. FIGS. 21A-21B described profiles being designated by hardware/software/combination switches (the switches having been described with respect to FIGS. 19A-19B). In FIG. 21A, the collection of profiles 2101 includes owner profile 2102, veterinarian/third-party profile 2103, airplane mode profile 2104, and location alert profile 2105. FIG. 21B shows the collection of profiles 2110 with the airplane mode switch and the locations mode switch designating at least some of the profiles. For instance, when airplane mode switch 2112 is on, the wearable device operates in airplane mode profile 2113. When airplane mode switch is off 2111, the location alert switch status is checked. If the location alert switch is on 2115, the wearable device operates in the location alert profile 2118. If the location alert switch is off 2114, the wearable device operates in one of the owner profile 2116 or the veterinarian/third-party profile 2117 (as separately designated by the owner and/or veterinarian/third-party).

FIG. 22 shows an example of how profiles may be selected in the wearable device as well as in the DMS in accordance with one or more aspects of the disclosure. Wearable device 2201 shown relative to DMS 2213. At step 2202, an initial profile is set for the wearable device 2201. In step 2203, it is determined whether a sensor or combination of sensors has exceeded one or more thresholds as described herein. If yes, then the wearable device modifies its own profile to change to a different profile or operation mode as shown in step 2204. Also, as shown by the yes arrow extending down from step 2203, the derived events may be uploaded to the DMS in step 2205, raw data may be uploaded to the DMS in batches as shown in step 2206, or raw data may be continuously uploaded to the DMS in step 2207 depending on the new profile or new operation mode. If no from step 2203, the derived events may be uploaded to the DMS in step 2205, raw data may be uploaded to the DMS in batches as shown in step 2206, or raw data may be continuously uploaded to the DMS in step 2207 depending on the current profile or current operation mode.

Next, content from wearable device 2201 is received at the DMS 2213 at step 2208. In step 2209, the data is stored (for instance, in a database in one or more servers with dynamic or solid-state memory as shown by database 2210) and subsequently analyzed. If in step 2211, an alert has been triggered from the analyzed data, then DMS 2213 instructs wearable device 2201 to change to a different profile or operation mode in accordance with the alert level determined in step 2211. Alternatively, if no from step 2211, no alert has been determined and the DMS 2213 continues to monitor for content from wearable device 2201 in step 2208.

Figure 23:
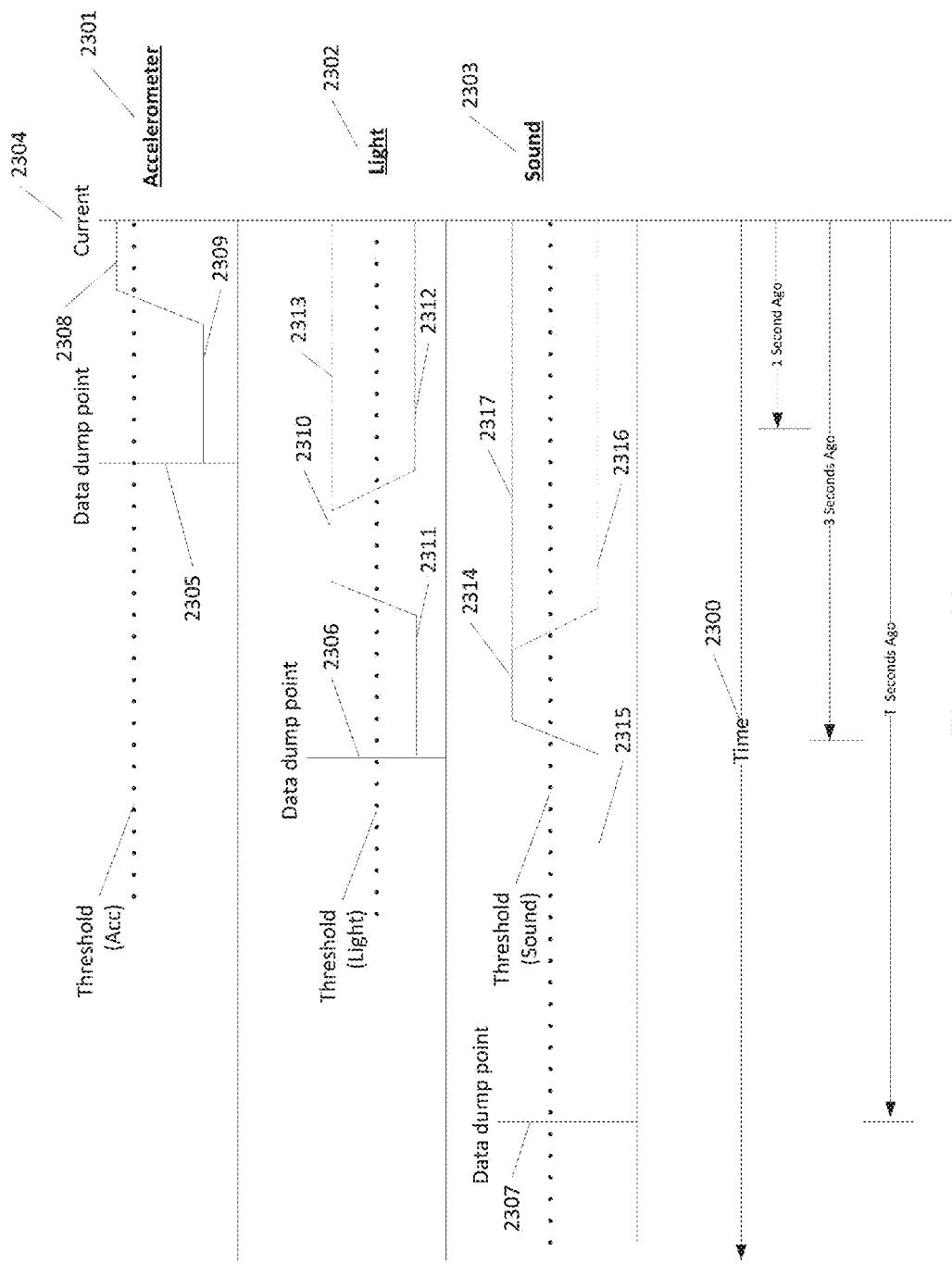
FIG. 23 shows an illustrative example of relevancy windows of readings of on sensor in relation to other sensors in accordance with one or more aspects of the disclosure.

FIG. 23 shows an example of how output from various sensors may be stored for an interval of time and then discarded in accordance with one or more aspects of the disclosure. FIG. 23 shows the past history for signals from accelerometer 2301, light sensor 2302, and sound sensor (microphone) 2303. In this example, older readings 2309 from accelerometer 2301 were below an accelerometer threshold level {Threshold(acc)}. However more recently, the signal from the accelerometer rose to level 2308, which is above {Threshold(acc)}.

As described above, processor 100 may then evaluate previous readings from other sensors. Previous values from light sensor 2302 are evaluated. Looking back in the recent history of the values from light sensor 2302, the readings were originally at level 2311, which is below the light threshold {Threshold(light)}. However, more recently, the light level rose to the level at 2310. As this level at 2310 is above the light threshold { Threshold(light)}, the values from the light sensor corroborate the event that may be have been detected by accelerometer 2301. With respect to sound level, older sound level readings were at level 2315, which were below the sound threshold { Threshold(sound)}. More recently, the sound level rose to level 2314, which is above the sound threshold{Threshold(sound)}. Here, the output from the sound sensor also corroborates event that may have been detected by accelerometer 2301.

With respect to both the light sensor 2302 and sound sensor 2303, an individual signal value different from a maximum value above a threshold having been reached during a time interval is less relevant than the signal having reached the threshold during the time window. Stated differently, once it has been determined that a light signal is above the light threshold {Threshold(light)} for sensor reading 2310, other readings between levels 2312 and 2313 are not considered for this threshold analysis. Similarly, variants between sound level 2316 and 2317 are less relevant than the sound level 2314 having passed the sound threshold level {Threshold(sound)} as the sound threshold has already been met.

Finally, FIG. 23 shows data dump points 2305, 2306, and 2307 after which insignificant signal readings are dumped from the memory of processor 100 and/or storage 105. Interestingly, the data dump points 2305, 2306, and 2307 do not have to be at the same time window from the present. Rather each may have its own separate window length during which signal levels are maintained.

Figure 24:
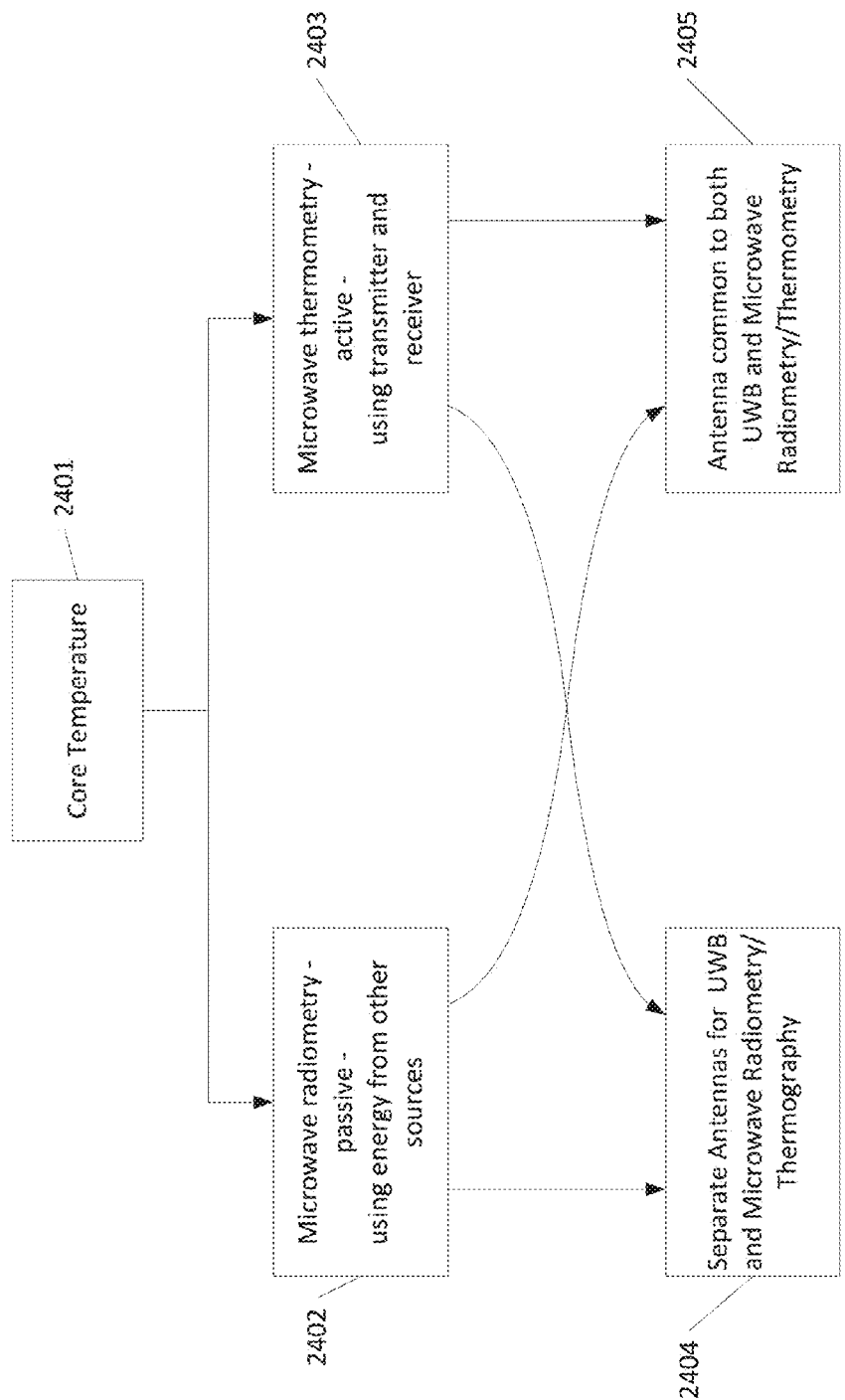
FIG. 24 shows an example of different techniques for monitoring core temperature including microwave radiometry and microwave thermometry in accordance with one or more aspects of the disclosure.

FIG. 24 shows an example of different techniques for monitoring core temperature including microwave radiometry and microwave thermometry in accordance with one or more aspects of the disclosure. For instance, core temperature 2401 may be determined through passive technologies including microwave radiometry 2402 in which energy from other sources is used to determine core temperature. Also, active techniques including microwave thermometry 2403 may be used to determine core temperature. For these two examples, separate antennas may be used for ultra-wideband device (UWB) and the microwave radiometry/thermography core temperature determination system as shown by state 2404. Alternatively, a single antenna may be shared between the UWB and the core temperature determination device. For example, one or more switches may be used to alternatively connect the shared antenna to the UWB in the microwave radiometry/thermography core temperature determination system as shown by state 2405.

Paired Thermometers and Core Temperature Estimation

Two digital thermometers may be used for determining presence of the band on a subject, relative positioning of the band on the subject, and estimating the core temperature of the subject.

One of the thermometers is located on the front of the unit's housing (outward-facing surface) and is designed to read the ambient temperature directly in front of the animal. The other thermometer sensor is located on the inside collar location (inward-facing surface). In the case of estimating core temperature for accurate trending, a preferred time is about two hours in the morning before the animal wakes from deep sleep. This is period of time is usually described as the nadir. Alternatively, a useful period of time is during a low activity, slow-wave sleep phase.

To insure that the animal is being measured at the right time, the user/animal's profile is checked. For instance, as some animals follow the sleep habits of their owners, taking temperature readings from an animal at 4 am whose owner works from midnight until 8 am would be less useful than when the owner is asleep and the animal is asleep as well.

Next, the accelerometer is checked to confirmed that the animal has been stationary for some time and has been exhibiting signs of deep sleep (e.g., slow-wave sleep). This may be done by checking the period of time the accelerometer has shown low activity and/or using other sensors that detect steady rhythmic breathing and/or panting (e.g., a microphone). It is also expected that animal, while in the prone (sternal recumbency) position, will fill out the collar once the skin and muscles are relaxed and in most cases the collar will be pushed up against the front of the neck.

Many dogs sleep on their chest (prone, sternal recumbency), allowing maximum contact between the body temperature sensor and the neck tissue. Once the collar-side temperature sensor reaches equilibrium, its reading is compared to the ambient temperature sensor's readings among other information (e.g., external RSS weather feeds for the local area).

The first calculation is based on the range of the ambient temperature. If it is falls within a temperate range of, for instance, 65 to 75 degrees Fahrenheit, an ambient temperature coefficient may generally not be required. The second calculation is based on the breed of the dog. If the breed is not known, then the profile would be consulted as to whether it is a short haired or long haired animal. This second coefficient would raise the reading from the inside collar thermometer up to the estimated core temperature of the animal.

In some cases, a sensor may not require repeated calibration (see, for instance, ADT7420 from Analog Devices, Inc.). The purpose of collecting this data is multi-fold. The most common means of collecting body temperature on a canine patient is via rectal thermometry. If one can estimate the body temperature of the canine patient without rectal thermometry in a home environment, and relay that information to the veterinarian and to the owner, one may be able to detect symptoms of disease (or other conditions including hypothermia or hypothermia) earlier. Some patients are not candidates for rectal thermometry (due to aggression, rectal disease, etc.). Obtaining a reliable core temperature from a non-invasive approach permits ready capture of this key vital sign.

Further, if the animal is in an inhospitable environment and its core temperature is changing quickly (such as ambient temperature of 20 degrees Fahrenheit and a core temperature reading of 85 degrees Fahrenheit), the owner may be alerted to the danger of hypothermia.

The techniques for monitoring core temperature usually result in data that will need to be adjusted for both the type and positioning of the sensor and the specific parameters of the animal. Adjustments for core temperature due to positioning of the sensor can preferably be accomplished in the initial time frame that the animal is wearing the device containing the sensor (for instance, the first 1, 5, 10, or 24 hours, etc.).

The following equation may be used for the core temperature determination:

$$\text{Core Temp} = ((A \times T_{external}) + B) \times ((C \times T_{internal}) + D) \quad \text{(Eq.1)}$$

where:
- $T_{external}$ is the temperature from the outward-facing thermometer
- $T_{internal}$ is the temperature from the inward-facing thermometer
- A is a scaling adjustment for the outward-facing thermometer
- B is an offset to the outward-facing thermometer
- C is a scaling adjustment for the inward-facing thermometer
- D is an offset for the inward-facing thermometer For typical room temperatures (for instance, 65-75° F.), no adjustment from the $T_{external}$ component may be needed (A may be the inverse of $T_{external}$ so that $A \times T_{external}$ is 1 and B=0). Next, the C adjustment may range in small values above and below 1 (for example, 0.90 through 1.10) to account for core temperature variations in breed, hair length, age, medical conditions of the animal, and other factors. The D offset may be used to account for an offset between the temperature $T_{internal}$ and the actual core temperature. So, for instance, if the animal's core temperature was 102.5° F. and the $T_{internal}$ (or $\{C \times T_{internal}\}$) was 95.5° F., offset D would be 7.0° F.

For temperatures below 65° F., an adjustment to $\{(C \times T_{internal}) + D\}$ may be needed to account for less heat being radiated through the animal's fur. In this case, $\{(C \times T_{internal}) + D\}$ may be increased linearly per drop in $T_{external}$. Alternatively, $\{(C \times T_{internal}) + D\}$ estimate may be increased at an exponential rate. So, for instance, at 60° F, the increase in the $(A \times T_{external})$ component may result in a 2% increase of $\{(C \times T_{internal}) + D\}$, at 50° F., the increase in the $(A \times T_{external})$ component may result in a 5% increase of $\{(C \times T_{internal}) + D\}$, and at 40° F., the increase in the $(A \times T_{external})$ component may be a 10% increase. Related decreasing adjustments to $\{(C \times T_{internal}) + D\}$ may be made based on ambient temperatures rising above 75° F.

With respect to the internal facing thermometer and temperature adjustments, core temperature adjustments for the positioning of the sensor are generally done to the breed average temperature of the animal being monitored and are due in part to the physical placement of the sensor from the animal in both the active and resting position. For example, the tightness of the device containing the sensor and its physical location on the animal (e.g., neck or torso) in both the animal's active and restive states may affect the core temperature data being received. In order to accurately monitor core temperatures, mathematical adjustment of the data received from the sensor may be necessary based on the physical location of the sensor. Alternatively, mathematical adjustment of the breed acceptable range of core temperatures can be utilized to correlate with the data being actually received from the sensor. Other equivalent mathematical adjustment of the sensor data or acceptable core temperature range can similarly be utilized in other aspects of the disclosure In addition to adjustment to sensor positioning, core temperature data may also need to be mathematically adjusted due to specific traits of the animal being monitored. For example, the particular traits of the individual animal may require an additional adjustment of the core temperature data received from the sensor. For example, these mathematical adjustments can be accomplished through the summation of the multiplicative result of a specific trait factor to the animal to a predetermined temperature offset D or part of adjustment C. Specific animal trait factors may include among others, breed, hair thickness, hair length, age, gender, pregnancy status, lactation, menstruation, and status of neutering. These specific trait factors can generally range from −5 to 5% based on the specific degree information also being utilized. For example, a 5 year, female, and pregnant Black Labrador may have the following specific animal trait factor adjustments: (1) Black Labrador+0.5% (2) pregnancy +0.2%; (3) age −0.4% thus yielding a total adjustment of +0.3%. Further, these adjustments may be applied as actual degree offsets as part of offset D as compared to a modification of adjustment C.

Alternatively, mathematical adjustment of the acceptable range of core temperature can be similarly utilized to correlate with the data actually received from the sensor. Other equivalent mathematical adjustment of the sensor data or acceptable core temperature range can similarly be utilized in other aspects of the disclosure.

For instance, equation 1 above may be cast as equation 2 below as the internal thermometer's reading adjusted by various factors as follows:

$$\text{Core Temp} = T_{internal} + X_{coarse} + Y_{fine} \quad \text{Eq. 2}$$

where:
- $T_{internal}$ is the temperature from the inward-facing thermometer
- $X_{coarse}$ is the coarse adjustment including an offset (corresponding to offset D above) and possible adjustments based on a reading from the external-facing thermometer
- $Y_{fine}$ is a fine adjustment relating to temperature adjusting conditions including, for instance, age (decreasing with age), breed (+ or −), hair length (increasing with hair length or density), sex, altered status (intact being warmer than neutered), menstruation, gestation, lactation, sickness/illness (generally higher, unless very sick, which will cause lower than normal temperatures).

Owner's User Interface

Figure 25:
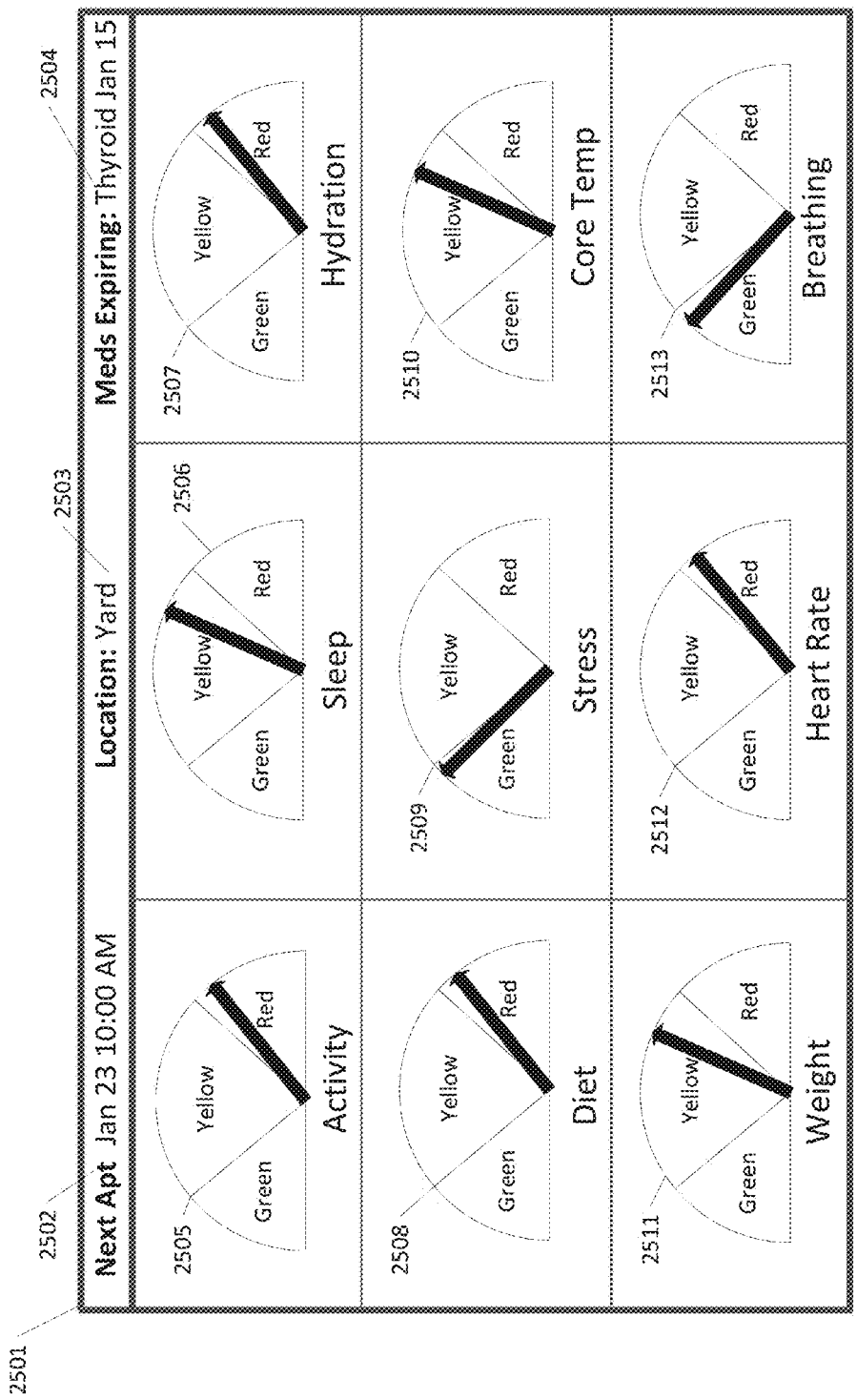
FIG. 25 shows a display of various conditions of a monitored animal in accordance with aspects of the disclosure.
Figure 26:
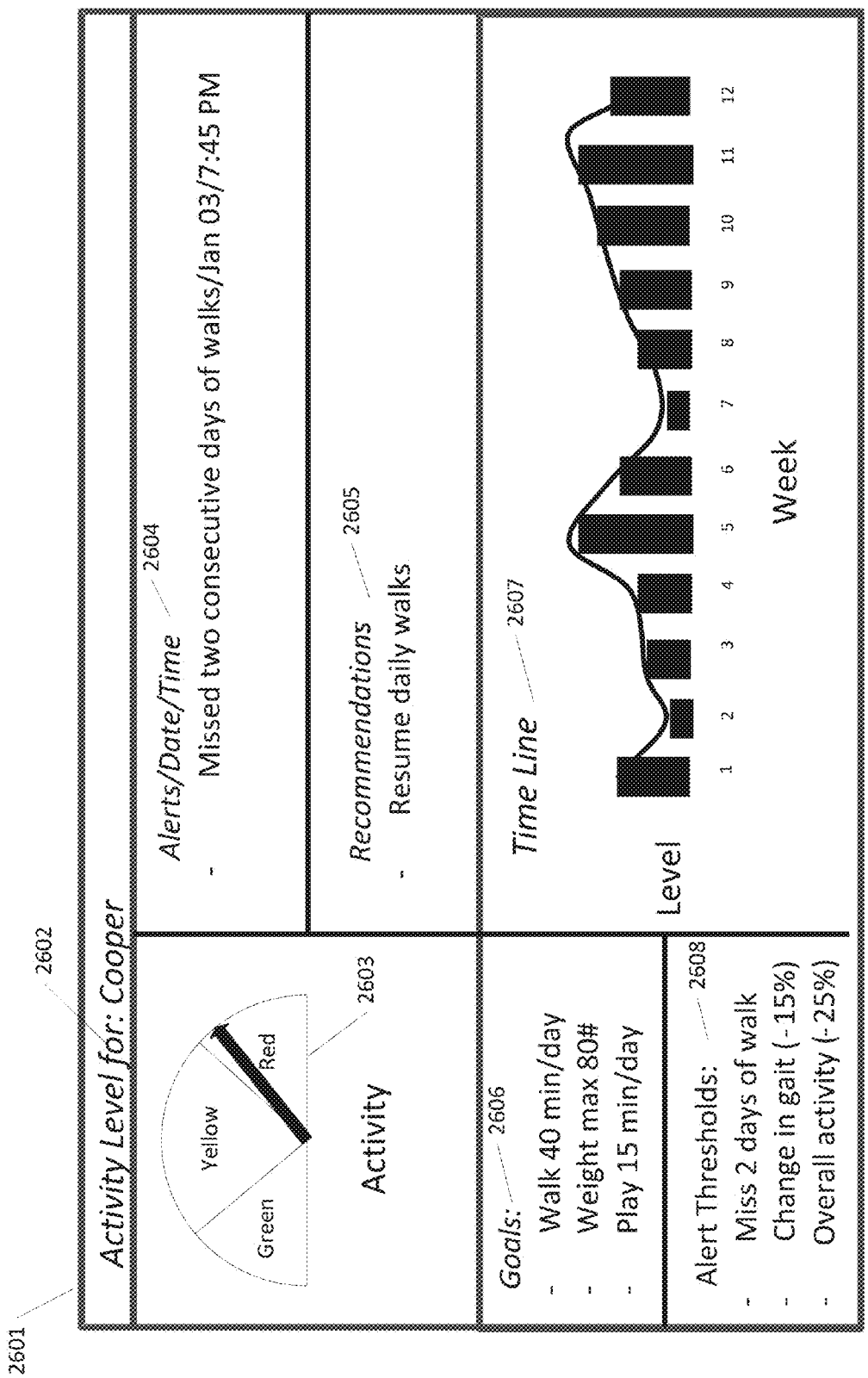
FIG. 26 shows a specific display relating to one of the monitored conditions of the animal of FIG. 25 in accordance with aspects of the disclosure.

FIGS. 25 and 26 show illustrative examples of an owner's user interface as displayable on a computer or smart phone. The Owner Health & Wellness Dashboard allows the owner to see in one place all trending information on the animal from sensor data and DMS derived data.

FIG. 25 shows a display 2501 of various information and conditions of a monitored animal in accordance with aspects of the disclosure. The display includes information drawn from both the wearable device 101 as well as from content from the veterinarian. For instance, information from the veterinarian includes the next scheduled appointment content 2502 and the identification of what medications are expiring next and the expiration dates. This information may help remind the user to keep the veterinarian appointment.

Next, the display 2501 includes content from the wearable device and/or the DMS in the form of instantaneous vital signs/physiological signs were overall trends relevant to the animal. For instance, display 2501 includes graphical indicators of activity 2505, sleep 2506, hydration 2507, diet 2508, stress 2509, core temperature 2510, weight 2511, heart rate 2512, and respiration rate 2513. The following items relate to instantaneous vital signs/physiological signs from the wearable device: core temperature 2510, heart rate 2512, and respiration rate 2513.

In contrast to the vital signs, the following items relate to wearable device-derived events or DMS-derived events such that they incorporate content from different sensors and may include tracking of health-related vital signs/physiological signs and/or activities over time: activity 2505, sleep 2506, hydration 2507, diet 2508, stress 2509, and weight 2511.

For purposes of illustration, each of the graphical displays of these items is shown as a dial with an arrow pivoting from one side of the dial to the other based on the state of the displayed item (e.g., a green area indicating no concern, a yellow area indicating caution, and a red area indicating concern for that individual item).

FIG. 26 shows activity level for that particular animal in accordance with aspects of the disclosure. The Owner Level Detail screen allows the owner to drill down on a specific item from the dashboard and review goals, alerts, recommendations, and more detailed, long term analyses information. For instance, the display 2601 of FIG. 26 includes an identification of the animal 2602, a current indicator 2603 for the detail screen (in this example, the activity of the animal), and an alert message box 2604 identifying an alert determined by the wearable device 101 and or the DMS 301 (in this example that the animal missed two consecutive days of walks with an identification of the date and time of when the walks were missed). Next, the display 2601 may further include recommendations in field 2605 to improve the health of the animal (for instance, to resume daily walks). The display 2601 may include one or more goals as set by the veterinarian, the owner, or the DMS 301. In this example, the goals are to walk 40 minutes per day, to keep the animal's weight below 80 pounds and to play 15 minutes. The display 2601 may further include an identification of the alert thresholds in field 2608. In this example, the alert thresholds are missing two days of a walk, a change in gait dropping 15%, and an overall drop in activity of 25%.

Finally, a timeline of the displayed item of detail may be shown as content 2607. Here, the timeline shows how the animal's activity level has changed over 12 weeks.

While the detailed screen 2601 of FIG. 26 relates to activity, it is appreciated that similar detail screens may be provided for other items identified in FIG. 25 with similar content including a graphical indication of the current status of that item, alerts, recommendations, goals, alert thresholds, and timelines.

Although example embodiments are described above, the various features and steps may be combined, divided, omitted, and/or augmented in any desired manner, depending on the specific secure process desired. This patent should not be limited to the example embodiments described, but rather should have its scope determined by the claims that follow.

We claim:

1. A wearable device for an animal comprising:
a housing having a first surface configured to be facing the animal and a second surface configured to be facing away from the animal;
a first thermometer located on the first surface comprising a first set of one or more sensors configured to be located at one or more first locations proximate to the animal and configured to output one or more first signals relating to a first temperature, wherein the first set of the one or more sensors comprises one or more non-skin contact sensors;
a second thermometer located on the second surface comprising a second set of one or more sensors configured to be located at one or more second locations proximate to the animal and configured to output one or more second signals relating to a second temperature; and
a processor configured to determine the first temperature and the second temperature based respectively on the one or more first signals and the one or more second signals, wherein the processor is configured to determine an adjustment based on the one or more first locations and the one or more second locations,
wherein the processor is configured to modify the first temperature based at least on the adjustment.

2. The wearable device according to claim 1,
wherein the adjustment includes a coarse adjustment and a fine adjustment.

3. The wearable device according to claim 2,
wherein the coarse adjustment is an offset based on the second temperature.

4. The wearable device according to claim 2,
wherein the fine adjustment is an offset based on one or more characteristics associated with the animal including at least one of: age, breed, hair length, sex, altered status, menstruation, gestation, lactation, and sickness or illness.

5. A method for determining a temperature of an animal comprising:
receiving at a processor a first set of one or more first signals from one or more first sensors of a first thermometer positioned in a housing worn by the animal, wherein the first thermometer is positioned to face the animal and the one or more first sensors comprise one or more non-skin contact sensors and are located at one or more first locations proximate to the animal;
receiving at the processor a second set of one or more second signals from one or more second sensors of a second thermometer positioned in the housing, wherein the second thermometer is positioned to face away from the animal and the one or more second sensors are located at one or more second locations proximate to the animal;
determining a first temperature value based on the first set of the one or more first signals and determining a second temperature based on the second set of the one or more second signals;
determining an adjustment based on the one or more first locations and the one or more second locations; and
modifying the first temperature value based on the adjustment.

6. The method according to claim 5,
wherein the adjustment includes a coarse adjustment and a fine adjustment.

7. The method according to claim 6,
wherein the coarse adjustment is an offset based on the second temperature.

8. The method according to claim 6,
wherein the fine adjustment is an offset based on one or more characteristics associated with the animal including at least one of: age, breed, hair length, sex, altered status, menstruation, gestation, lactation, and sickness or illness.

9. A wearable device for a non-human animal comprising:
a housing having a first surface configured to be facing the animal and a second surface configured to be facing away from the animal;
a first thermometer located on the first surface and configured to output a first signal;
a processor with an input configured to receive the first signal and to determine a first temperature value based on the first signal; and
a storage in which an adjustment is stored,
wherein the processor is configured to apply the adjustment from the storage to the first temperature value, and
wherein the adjustment is based at least on a non-human-breed-specific characteristic associated with the animal upon which the wearable device is placed.

10. The wearable device according to claim 9, wherein the adjustment is further based on one or more characteristics associated with the animal including at least one of: age, sex, altered status, menstruation, gestation, lactation, and sickness or illness.

11. A wearable device for an animal comprising:
a housing having a first surface and a second surface;
a first thermometer located on the first surface and configured to output a first signal relating to a first temperature relating to a temperature near the animal;
a second thermometer located on the second surface and configured to output a second signal relating to a second temperature relating to an ambient temperature;
a processor with an input configured to receive the first and second signals and to determine the first temperature and the second temperature respectively; and
a storage in which an adjustment is stored,
wherein the processor is configured to apply the adjustment from the storage to the first temperature and the adjustment is based at least on the second temperature and on a characteristic associated with hair associated with a breed associated with the animal.

12. The wearable device of claim 1, wherein the one or more first locations are different from the one or more second locations.

13. The wearable device of claim 1, wherein the one or more first locations or the one or more second locations are selected based on a posture associated with the animal.

14. The wearable device of claim 1, wherein the one or more first sensors comprise a plurality of sensors configured to output a plurality of first signals or the one or more second sensors comprise a plurality of sensors configured to output a plurality of second signals, wherein the processor is further configured to determine the adjustment based on a portion of the plurality of first signals or on a portion of the plurality of second signals.

15. The method of claim 5, wherein the one or more first locations are different from the one or more second locations.

16. The method of claim 5, wherein the one or more first locations or the one or more second locations are selected based on a posture associated with the animal.

17. The wearable device of claim 9, wherein the non-human-breed-specific characteristic associated with the animal upon which the wearable device is placed comprises a characteristic associated with fur associated with the breed.

18. The wearable device of claim 17, wherein the characteristic associated with the fur associated with the breed comprises fur length or fur density.

19. The wearable device of claim 11, wherein the characteristic associated with the hair associated with the breed associated with the animal comprises a characteristic associated with fur of a non-human animal breed.

20. The wearable device of claim 19, wherein the characteristic associated with the fur of the non-human animal breed comprises fur length or fur density.

* * * * *